US012582408B2

(12) United States Patent
Yuasa et al.

(10) Patent No.: US 12,582,408 B2
(45) Date of Patent: Mar. 24, 2026

(54) TISSUE CLOSURE METHOD, CLIP DEVICE, AND OPERATION METHOD OF CLIP DEVICE

(71) Applicant: OLYMPUS MEDICAL SYSTEMS CORP., Tokyo (JP)

(72) Inventors: Masaru Yuasa, Hachioji (JP); Motoi Satake, Kokubunji (JP); Toshinori Tamura, Hirosaki (JP); Shogo Shindo, Koganei (JP)

(73) Assignee: Olympus Medical Systems Corp., Tokyo (JP)

( * ) Notice: Subject to any disclaimer, the term of this patent is extended or adjusted under 35 U.S.C. 154(b) by 265 days.

(21) Appl. No.: 18/112,201

(22) Filed: Feb. 21, 2023

(65) Prior Publication Data

US 2023/0277193 A1     Sep. 7, 2023

Related U.S. Application Data

(60) Provisional application No. 63/314,558, filed on Feb. 28, 2022, provisional application No. 63/313,813,
(Continued)

(51) Int. Cl.
| | |
|---|---|
| *A61B 17/128* | (2006.01) |
| *A61B 17/08* | (2006.01) |
| *A61B 17/122* | (2006.01) |

(52) U.S. Cl.
CPC ...... *A61B 17/1285* (2013.01); *A61B 17/1227* (2013.01); *A61B 17/083* (2013.01)

(58) Field of Classification Search
CPC ... A61B 17/083; A61B 17/10; A61B 17/1227; A61B 17/128
See application file for complete search history.

(56) References Cited

U.S. PATENT DOCUMENTS

| | | | |
|---|---|---|---|
| 2003/0083677 A1* | 5/2003 | Damarati | A61B 17/122 606/151 |
| 2005/0080440 A1* | 4/2005 | Durgin | A61B 17/122 606/151 |

(Continued)

FOREIGN PATENT DOCUMENTS

| | | |
|---|---|---|
| CN | 104244844 A | 12/2014 |
| CN | 204364061 U | 6/2015 |

(Continued)

OTHER PUBLICATIONS

JP 2010178897 A English translation (Year: 2010).*
(Continued)

*Primary Examiner* — Katherine H Schwiker
*Assistant Examiner* — Zehra Jaffri
(74) *Attorney, Agent, or Firm* — Morgan, Lewis & Bockius LLP

(57) ABSTRACT

A tissue closure method comprises grasping a first portion of a tissue between a first arm and a central arm, restricting a sliding of a first slider while grasping the first portion, the first slider configured to open and close the first arm relative to the central arm, grasping a second portion of the tissue between a second arm and the central arm while restricting the sliding of the first slider, indwelling the first arm, the second arm, and the central arm in a body.

8 Claims, 45 Drawing Sheets

Related U.S. Application Data filed on Feb. 25, 2022, provisional application No. 63/313,310, filed on Feb. 24, 2022.

(56)                    References Cited

U.S. PATENT DOCUMENTS

| | | | | |
|---|---|---|---|---|
| 2008/0249354 A1* | 10/2008 | Muyari | ............... | A61B 18/1492 |
| | | | | 600/104 |
| 2012/0185032 A1* | 7/2012 | Lawrence-Brown | ...... | A61F 2/07 |
| | | | | 623/1.12 |
| 2015/0057704 A1* | 2/2015 | Takahashi | ........... | A61B 17/0057 |
| | | | | 606/221 |
| 2016/0157862 A1* | 6/2016 | Hernandez | ............ | A61B 17/083 |
| 2021/0259700 A1* | 8/2021 | Zhang | ................. | A61B 17/1222 |

FOREIGN PATENT DOCUMENTS

| | | | |
|---|---|---|---|
| CN | 111481304 A | | 8/2020 |
| CN | 112955082 A | | 6/2021 |
| EP | 3476332 A1 | | 5/2019 |
| JP | 2010178897 A | * | 8/2010 |

OTHER PUBLICATIONS

Office Action dated Sep. 26, 2025 (OA-1), issued in corresponding Chinese Patent Application No. 202310136844.8.
Office Action dated Oct. 1, 2025 (OA-2), issued in corresponding Chinese Patent Application No. 202310142545.5.
Office Action dated Jan. 2, 2026, issued in corresponding Chinese Patent Application No. 202310156556.9.

* cited by examiner

TISSUE CLOSURE METHOD, CLIP DEVICE, AND OPERATION METHOD OF CLIP DEVICE

The present disclosure claims priority on U.S. Provisional Application No. 63/313,310, filed Feb. 24, 2022, U.S. Provisional Application No. 63/313,813, filed Feb. 25, 2022, and U.S. Provisional Application No. 63/314,558, filed Feb. 28, 2022. The disclosure of each of the prior applications is hereby incorporated by reference herein in its entirety.

TECHNICAL FIELD

The present disclosure relates to a tissue closure method, a clip device, and an operation method of a clip device.

BACKGROUND

In endoscopic therapy, an endoscopic treatment device using a clip capable of performing the hemostasis by ligating a resection portion or the like after the treatment is used. The clip of the endoscopic treatment device is locked in a state of clamping the resection portion or the like and then indwelled in the luminal cavity.

The endoscopic treatment device described in Chinese Patent Application, Publication No. 111481304 includes a fixed arm having a clip on the distal-end side and two movable arms arranged on both sides of the fixed arm. Also, the endoscopic treatment device includes sliders capable of independently controlling the opening and closing of the two movable arms in two operation portion main bodies (handles) of an operation portion provided on the proximal-end side opposite to the distal-end side. At first, the surgeon brings the clip to approach the tissue in the vicinity of the resection portion after the treatment, operates one slider to open and close the movable arm corresponding to the one slider so as to grasp a part of the tissue. The surgeon locks the opening and closing of the movable arm in order to keep the movable arm that grasps the portion of the tissue in a closed state. Next, the surgeon operates the other slider to open and close the movable arm corresponding to the other slider to grasp and lock the tissue other than the already grasped part of the tissue in a state of grasping part of the tissue, and then ligate the resection portion. Thereafter, the surgeon indwells only the clip ligating the resection portion in the luminal cavity.

SUMMARY

A tissue closure method comprises grasping a first portion of a tissue between a first arm and a central arm, restricting a sliding of a first slider while grasping the first portion, the first slider configured to open and close the first arm relative to the central arm, grasping a second portion of the tissue between a second arm and the central arm while restricting the sliding of the first slider, indwelling the first arm, the second arm, and the central arm in a body.

A clip comprises a fixed arm including a distal-end portion, a first movable arm configured to open and close relative to the fixed arm and a second movable arm configured to open and close relative to the fixed arm. The first movable arm includes a first arm-claw bent toward the fixed arm. The second movable arm includes a second arm-claw bent toward the fixed arm. The first arm-claw and the second arm-claw are arranged distally relative to and apart from the distal-end portion of the fixed arm in a longitudinal direction of the fixed arm. The first arm-claw and the second arm-claw face the distal-end portion of the fixed arm when the first movable arm and the second movable arm are closed relative to the fixed arm.

A clip device comprises a clip and an applicator. The clip comprises a fixed arm including a distal-end portion, a first movable arm configured to open and close relative to the fixed arm, and a second movable arm configured to open and close relative to the fixed arm. The applicator including a connector connected to the clip, a wire, a sheath, and an operation portion. The first movable arm includes a first arm-claw bent toward the fixed arm. The second movable arm includes a second arm-claw bent toward the fixed arm. The first arm-claw and the second arm-claw are arranged distally relative to and apart from the distal-end portion of the fixed arm in a longitudinal direction of the fixed arm. The first arm-claw and the second arm-claw face the distal-end portion of the fixed arm when the first movable arm and the second movable arm are closed relative to the fixed arm.

DESCRIPTION OF DRAWINGS

FIG. 10 is a view showing the operation portion of the applicator of the clip device when viewed from an upper side (or a lower side) in an open-close direction (up-down direction).

FIG. 16 is a schematic view showing a state of opening the second movable arm and moving the treatment portion to approach a second portion of the tissue to be grasped while the first movable arm of the treatment portion of the clip device is grasping the first portion of the tissue and a state of the operation portion and the stopper at this time.

Figure 17:
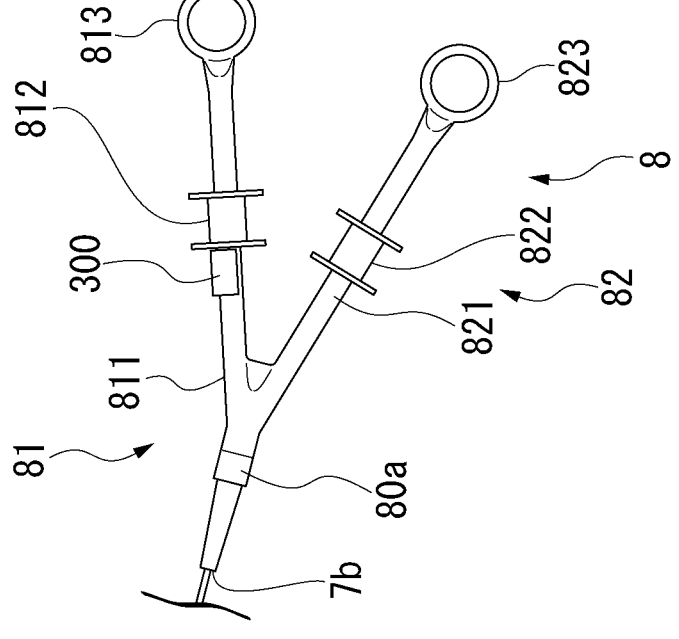
Figure 17:
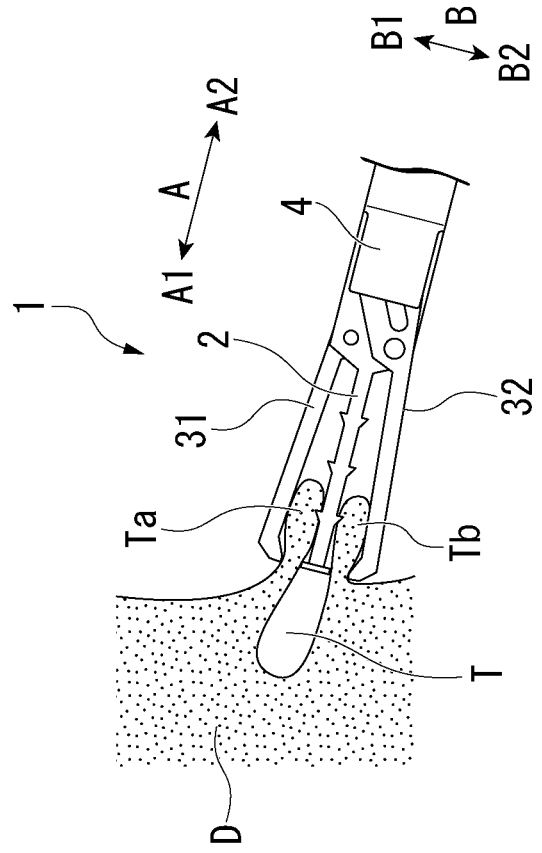

FIG. 17 is a schematic view showing a state of closing the second movable arm of the treatment portion of the clip device to grasp a second portion of the tissue and a state of the operation portion and the stopper at this time.

Figure 18:
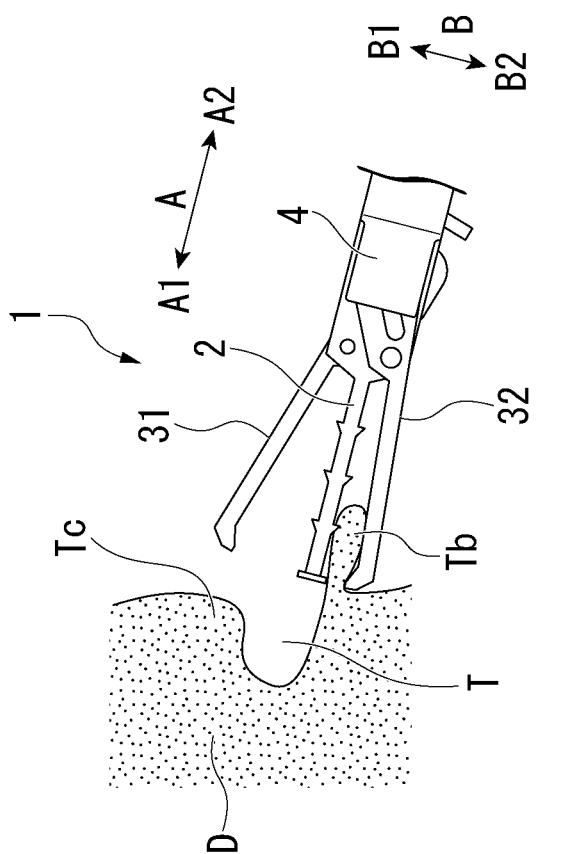

FIG. 18 is a schematic view showing a state of detaching the stopper attached to the first operation portion therefrom to open the first movable arm again and moving the treatment portion to approach a third portion of the tissue different from the first portion while the second movable arm of the clip device is grasping the second portion of the tissue and a state of the operation portion at this time.

Figure 19:
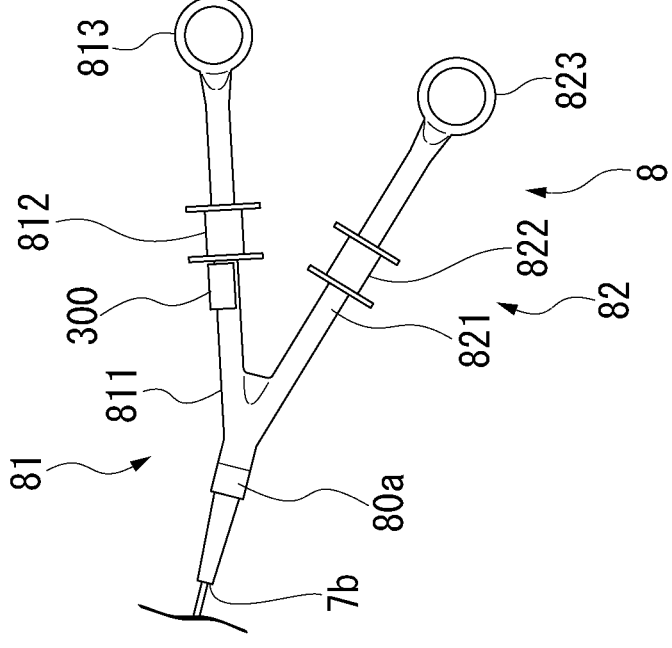
Figure 19:
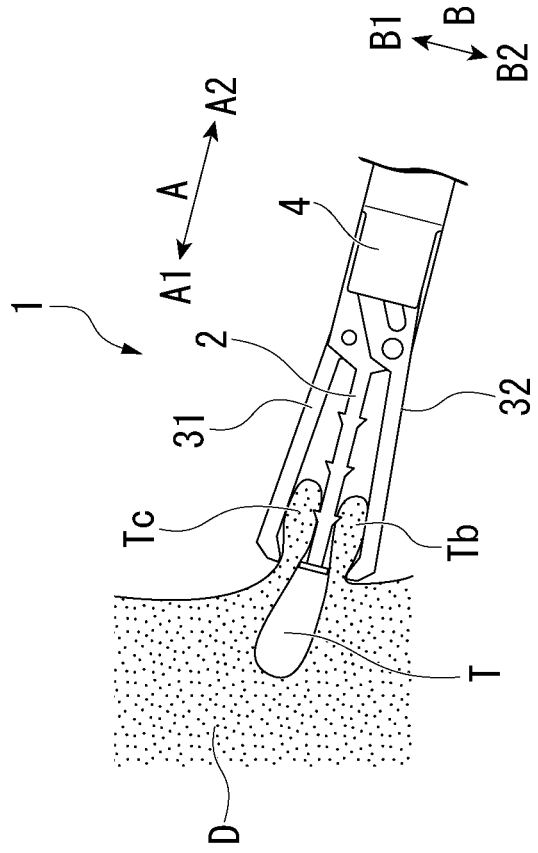

FIG. 19 is a schematic view showing a state of closing the first movable arm of the treatment portion of the clip device to grasp the third portion of the tissue and a state of attaching the stopper to the first operation portion at this time.

Figure 20:
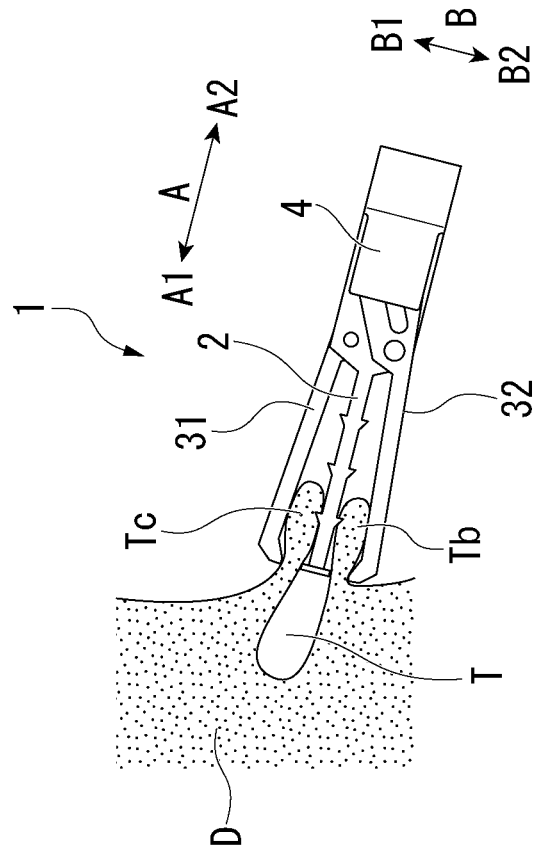

FIG. 20 is a schematic view showing a state of indwelling the treatment portion from the clip device in a state in which the treatment portion of the clip device grasps the tissue and the state of the operation portion and the stopper at this time.

Figure 21:
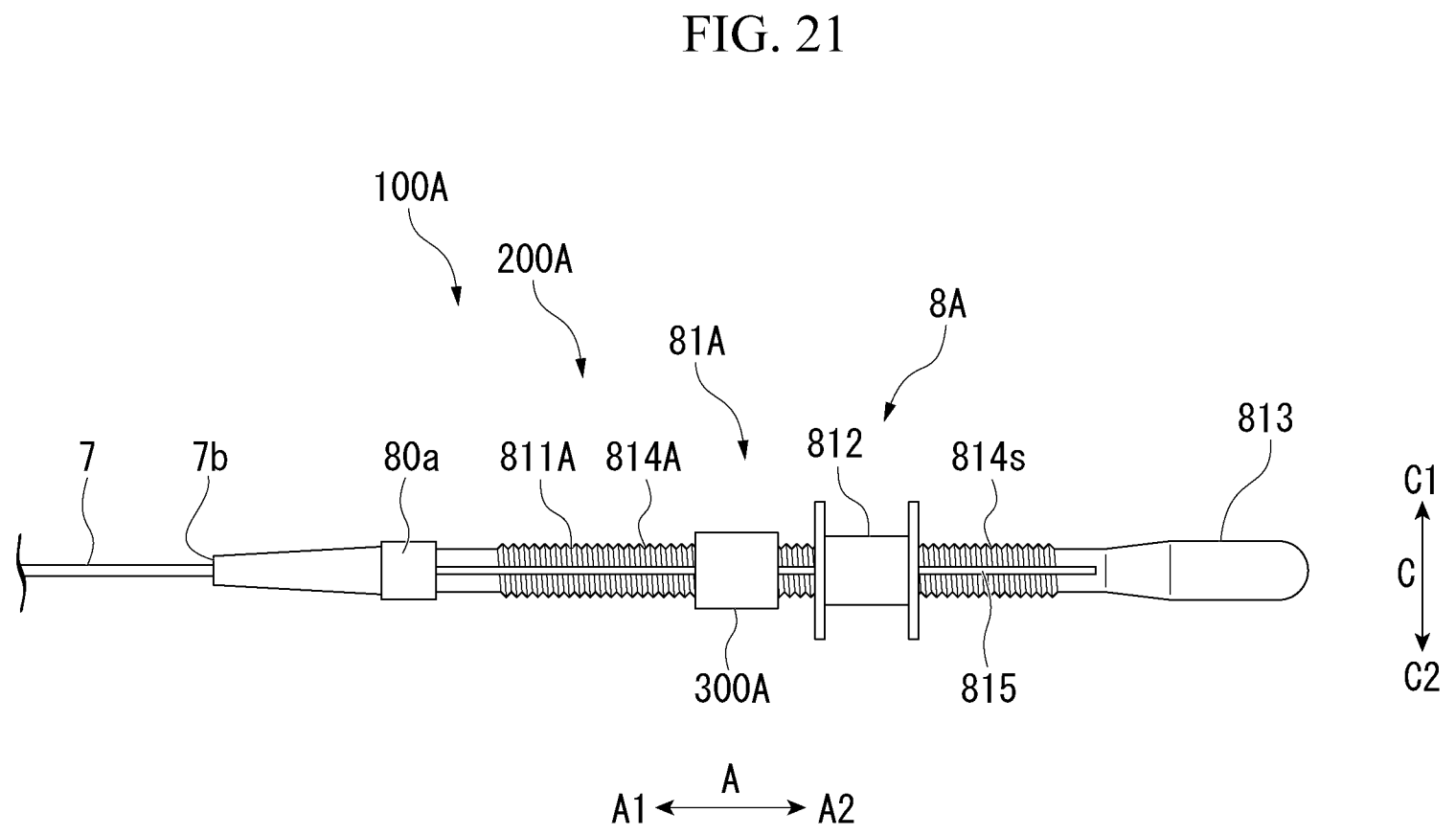

FIG. 21 is a view showing an operation portion of an applicator of a clip device according to a second embodiment of the present disclosure when viewed from an upper side in the open-close direction (up-down direction).

Figure 22:
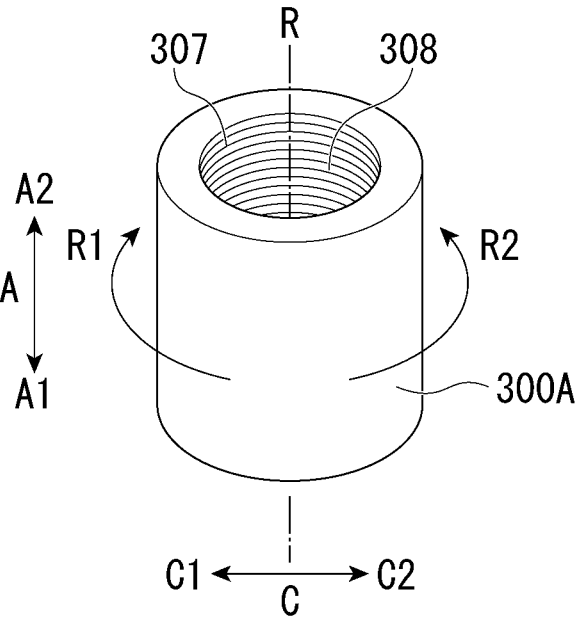

FIG. 22 is a perspective view showing the stopper of the clip device.

Figure 23:
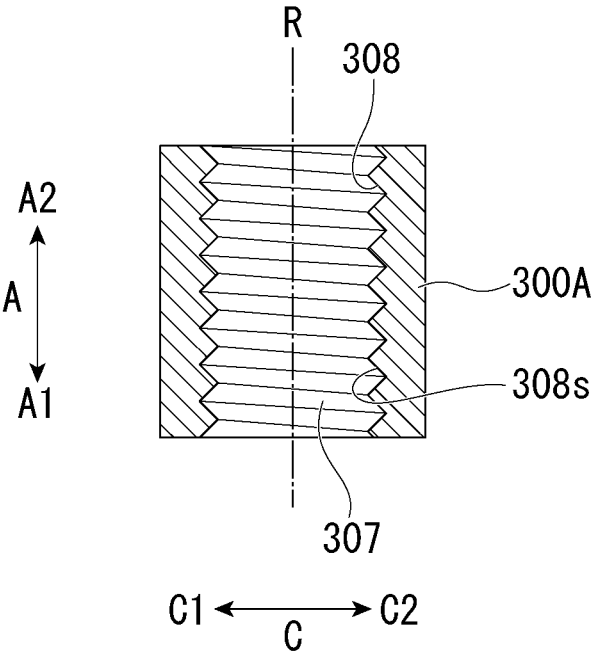

FIG. 23 is a cross-sectional view showing the stopper of the clip device.

Figures 24, 25:
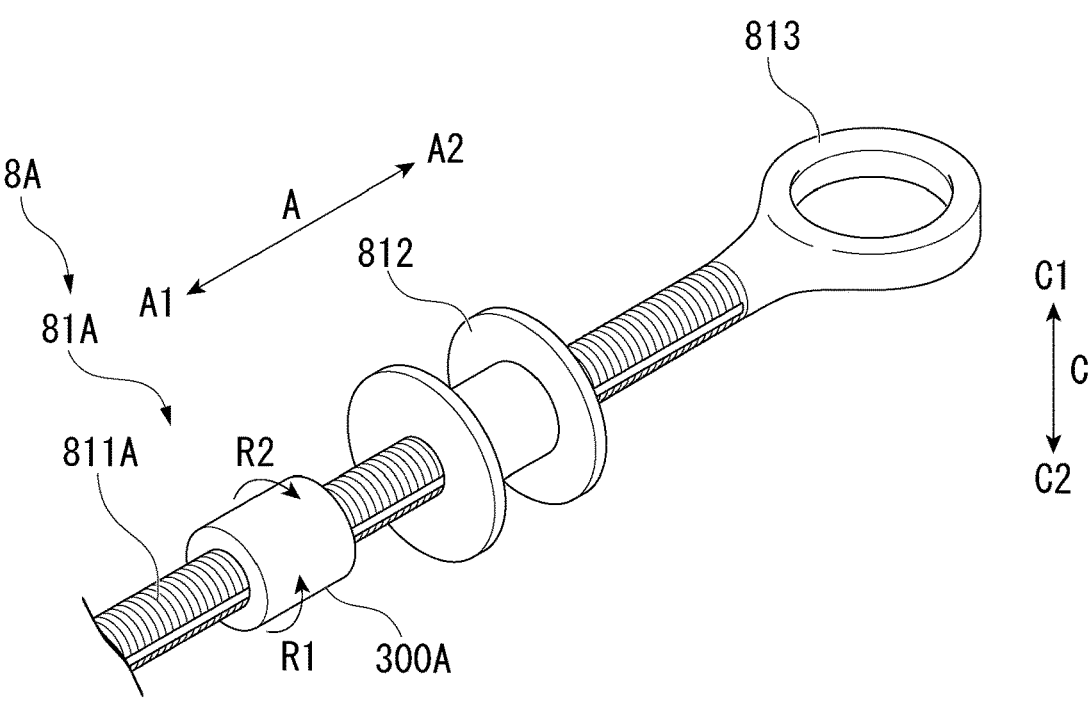

FIG. 24 is a perspective view showing the operation portion and the stopper of the clip device.

FIG. 25 is a view showing a modification example of the clip device according to the present disclosure.

Figure 26:
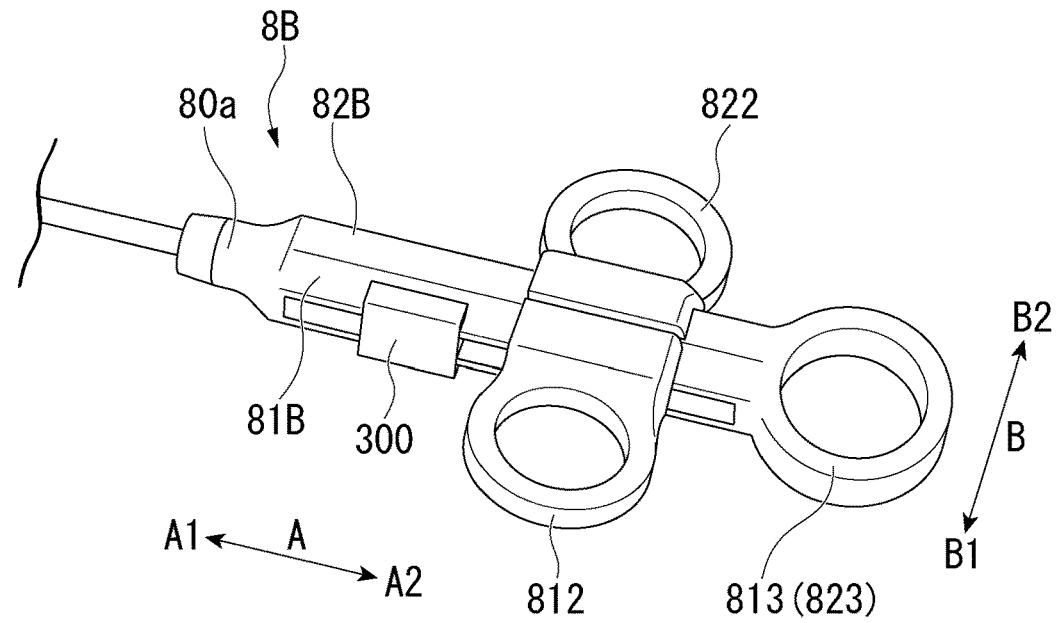

FIG. 26 is a view showing another modification example of the clip device according to the present disclosure.

Figure 27:
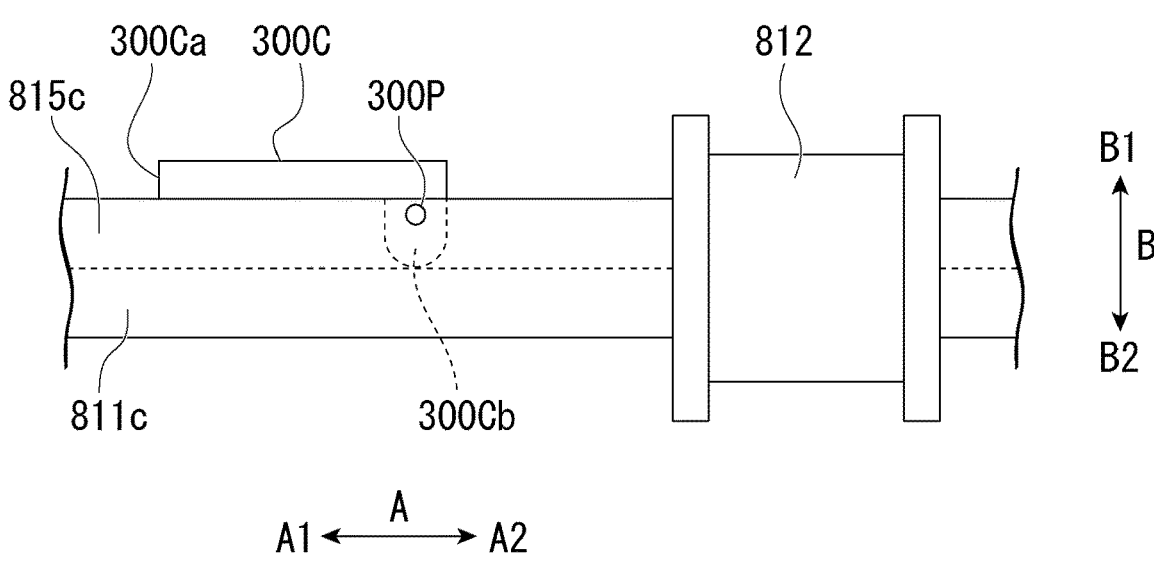

FIG. 27 is a view showing another modification example of the clip device according to the present disclosure.

Figure 28:
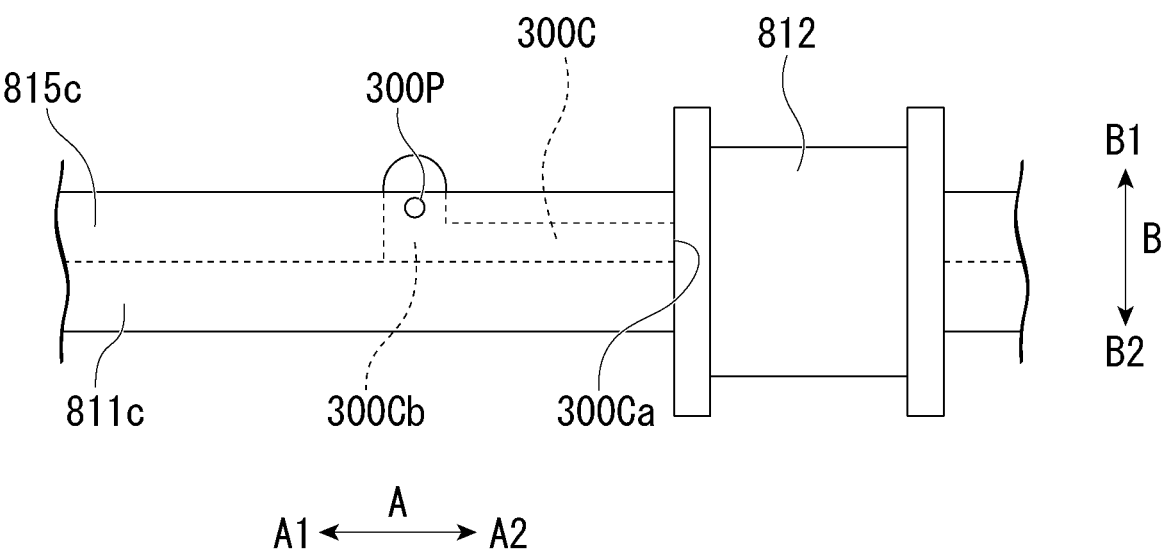

FIG. 28 is a view showing the same modification example of the clip device according to the present disclosure.

Figure 29:
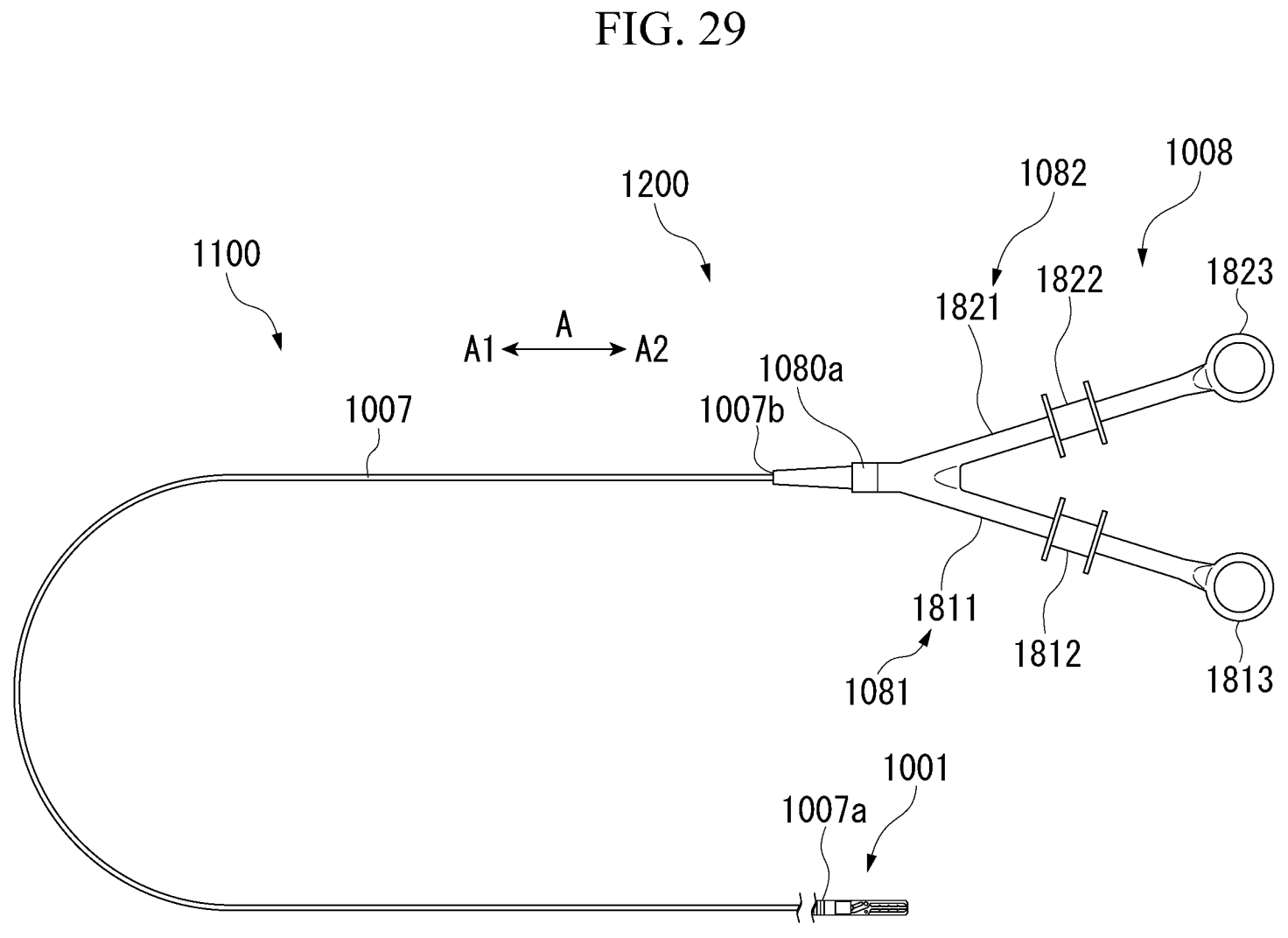

FIG. 29 is a view showing an overall configuration of a clip device according to a third embodiment of the present disclosure.

Figure 30:
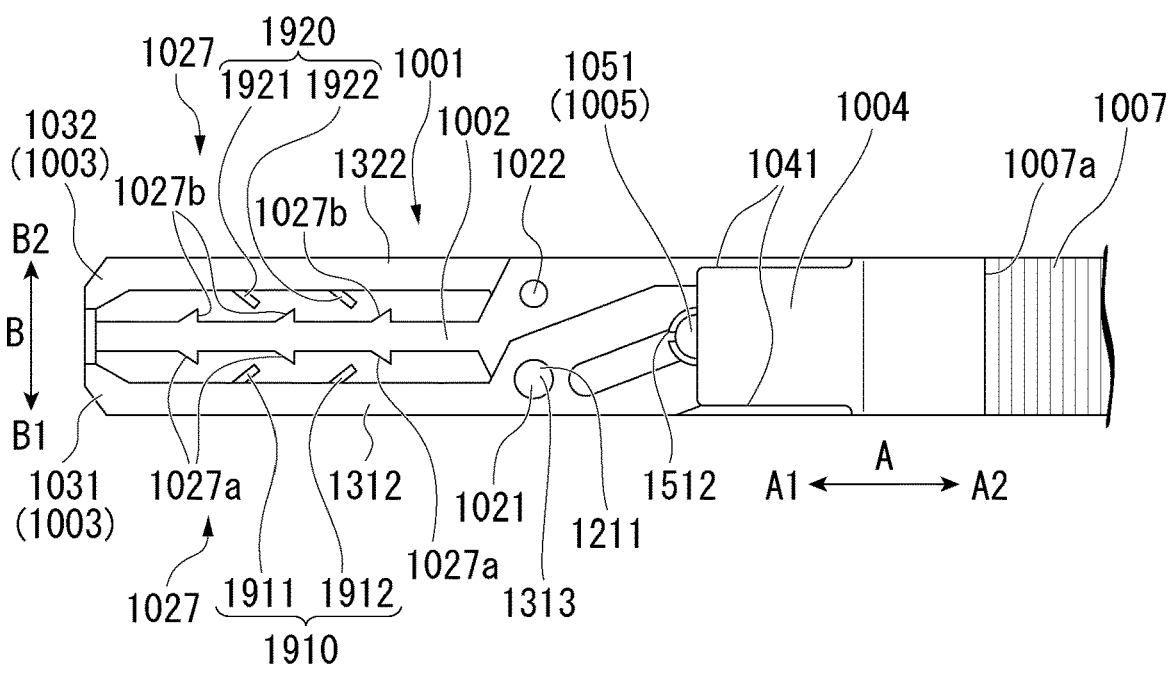

FIG. 30 is a view showing a state in which a treatment portion of the clip device is closed.

Figure 31:
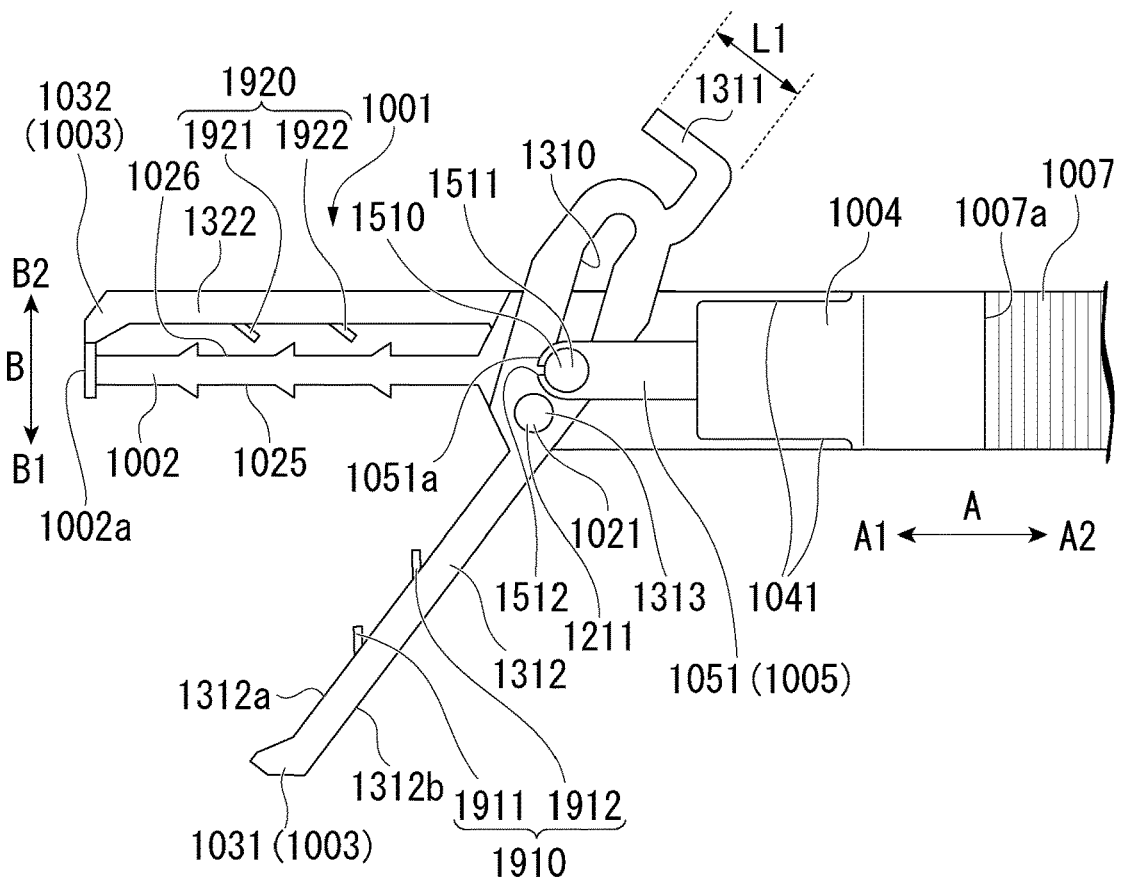

FIG. 31 is a view showing a state in which a first movable arm of the treatment portion of the clip device is opened when viewed from a left side of a thickness direction.

Figure 32:
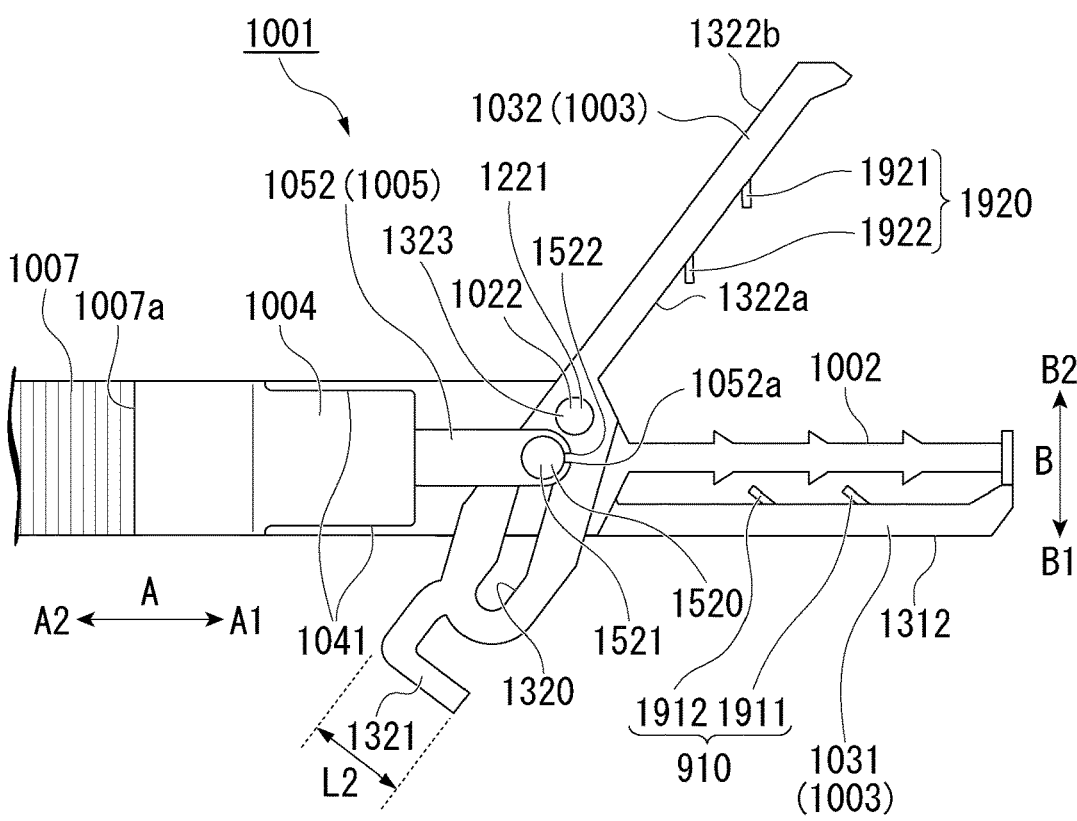

FIG. 32 is a view showing a state in which a second movable arm of the treatment portion of the clip device is opened when viewed from a right side of the thickness direction.

Figure 33:
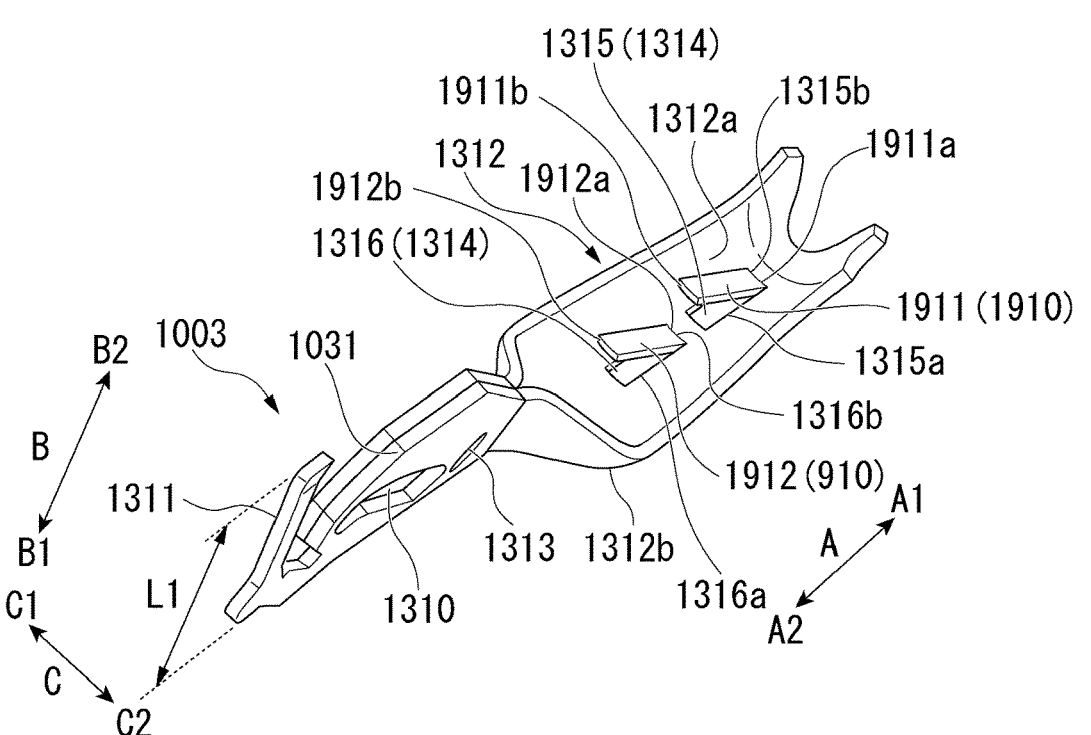

FIG. 33 is a view showing the first movable arm of the treatment portion of the clip device.

Figure 34:
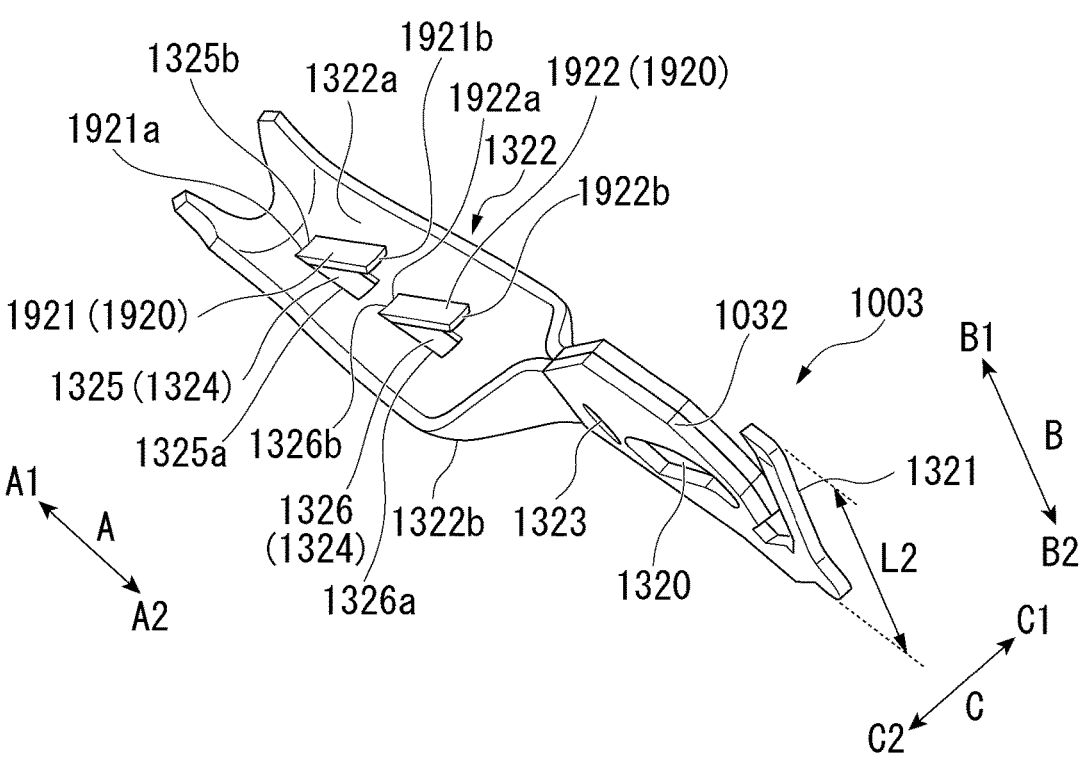

FIG. 34 is a view showing the second movable arm of the treatment portion of the clip device.

Figure 35:
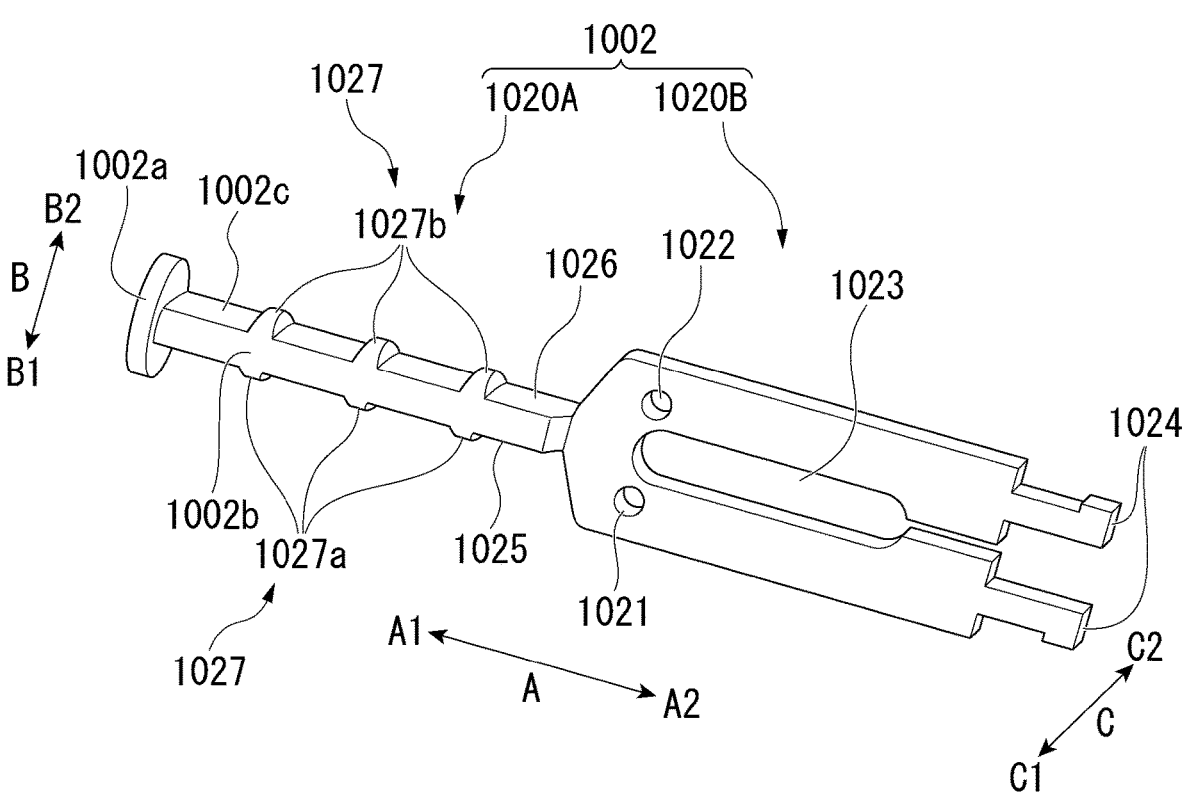

FIG. 35 is a view showing a fixed arm of the treatment portion of the clip device.

Figure 36:
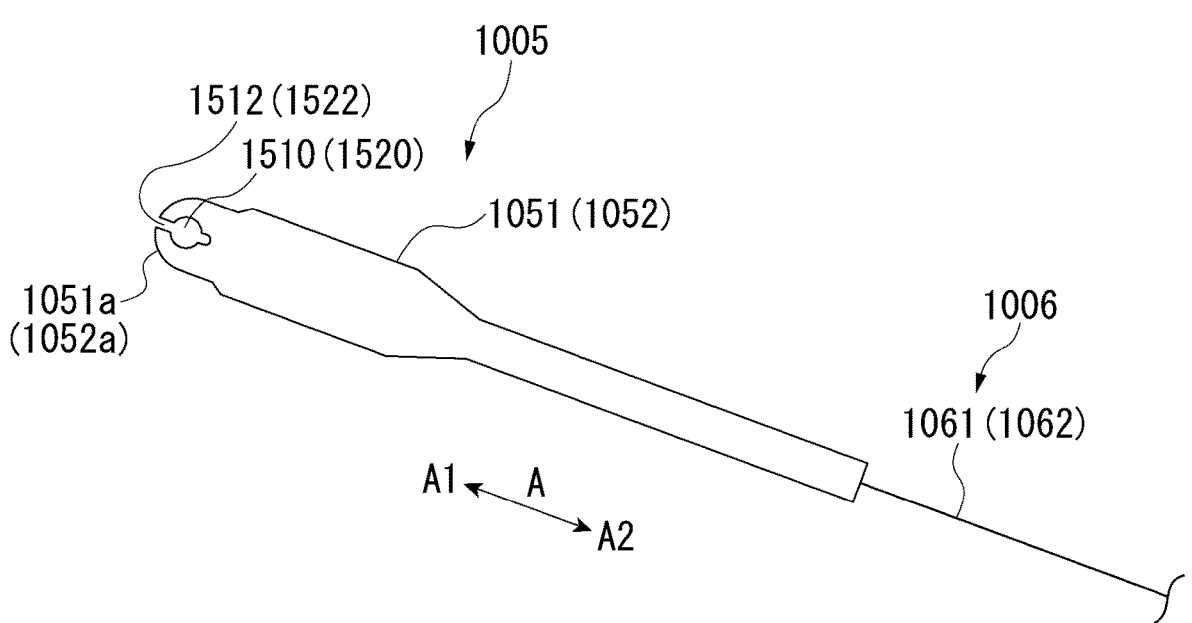

FIG. 36 is a view showing a traction member of an applicator of the clip device.

Figure 37:
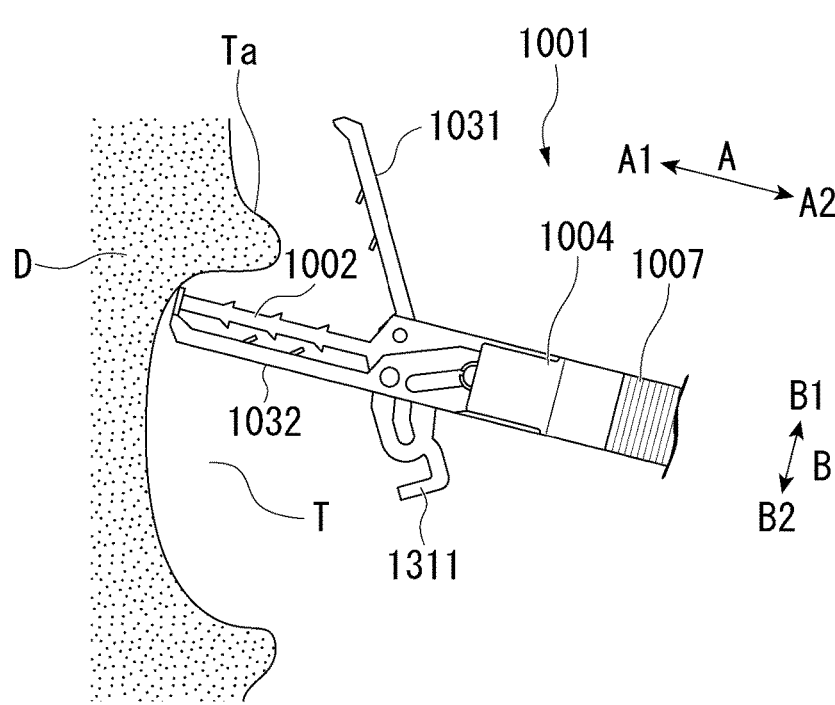

FIG. 37 is a schematic view showing a state of opening the first movable arm of the treatment portion of the clip device and moving the treatment portion to approach the tissue to be grasped.

Figure 38:
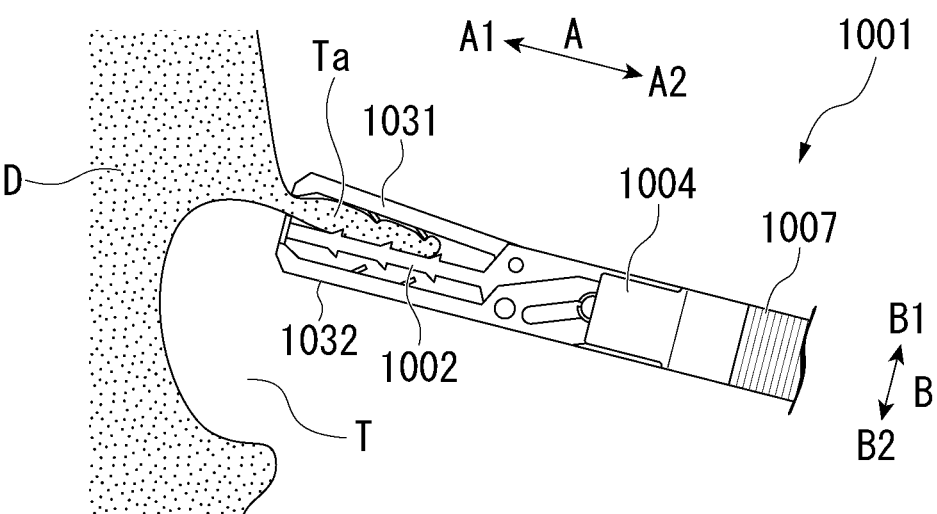

FIG. 38 is a schematic view showing a state of closing the first movable arm of the treatment portion of the clip device to grasp the tissue.

4

Figure 39:
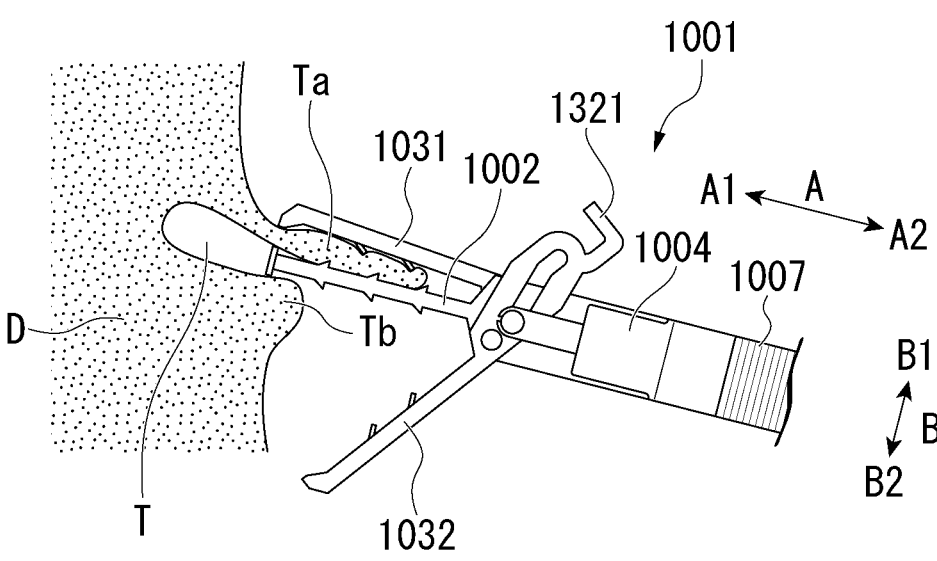

FIG. 39 is a schematic view showing a state of opening the second movable arm and moving the treatment portion to approach the tissue to be grasped while the first movable arm of the treatment portion of the clip device is grasping the tissue.

Figure 40:
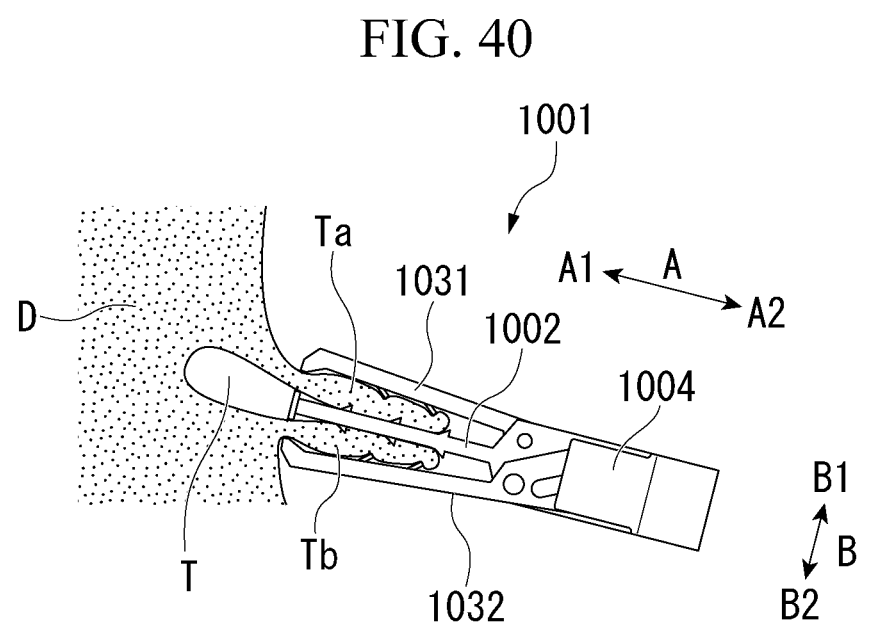

FIG. 40 is a schematic view showing a state of closing the second movable arm of the treatment portion of the clip device to indwell the treatment portion from the clip device in the state in which the treatment portion is grasping the tissue.

Figure 41:
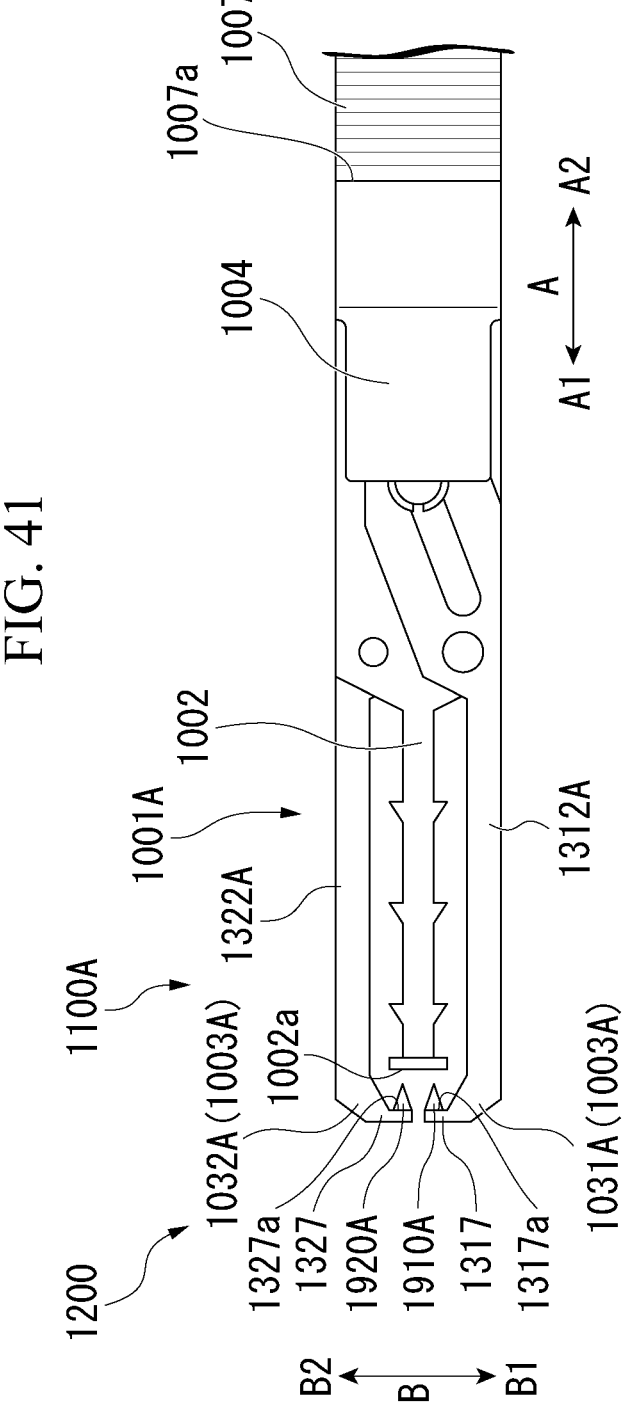

FIG. 41 is a view showing a state in which a treatment portion of a clip device according to a fourth embodiment of the present disclosure is closed.

Figure 42:
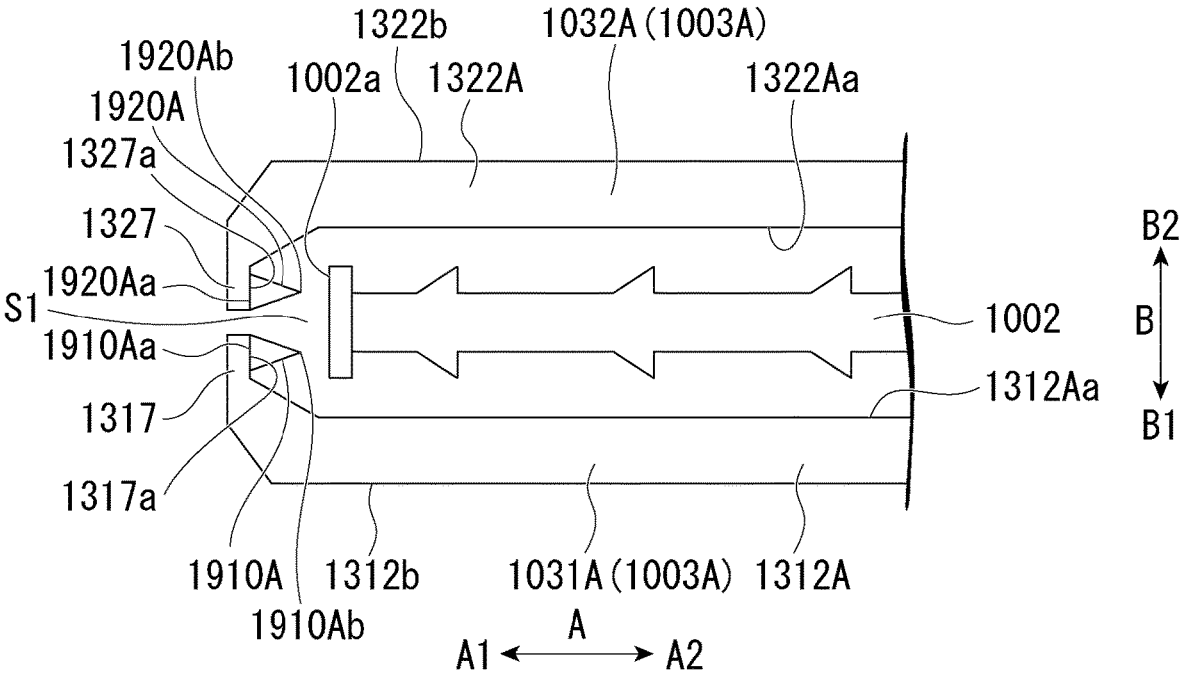

FIG. 42 is an enlarged view showing the treatment portion of the clip device.

Figure 43:
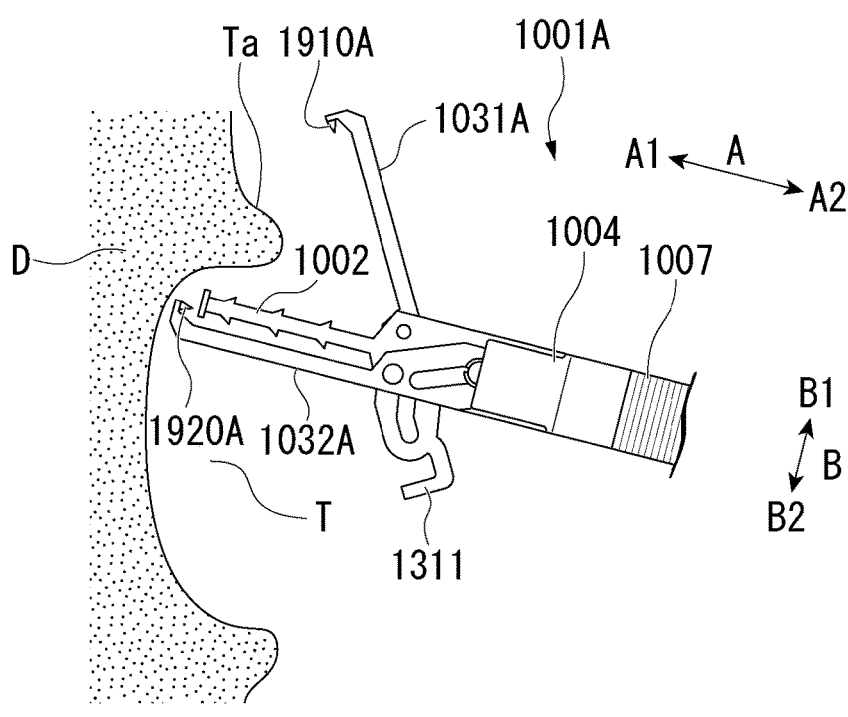

FIG. 43 is a schematic view showing a state of opening a first movable arm of the treatment portion of the clip device to make the treatment portion to approach the tissue to be grasped.

Figure 44:
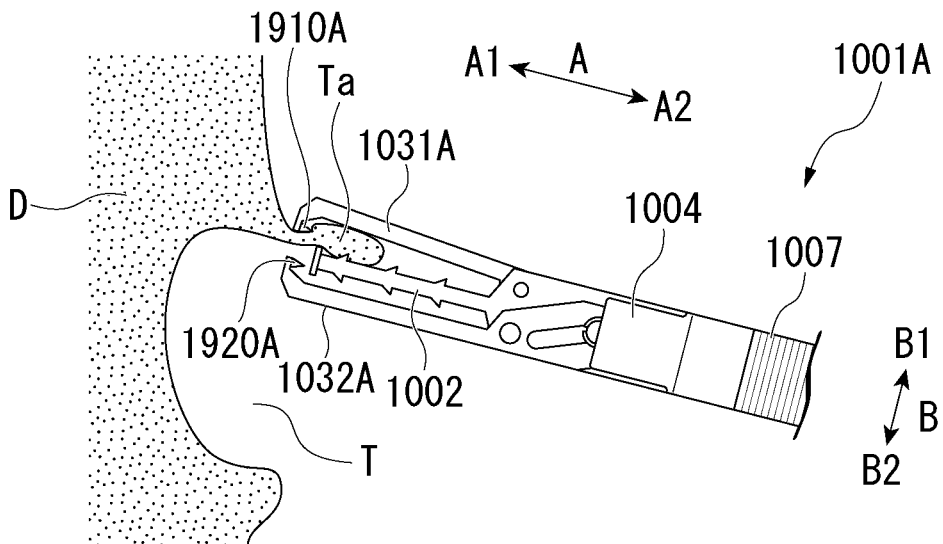

FIG. 44 is a schematic view showing a state of closing the first movable arm of the treatment portion of the clip device and grasping the tissue.

Figure 45:
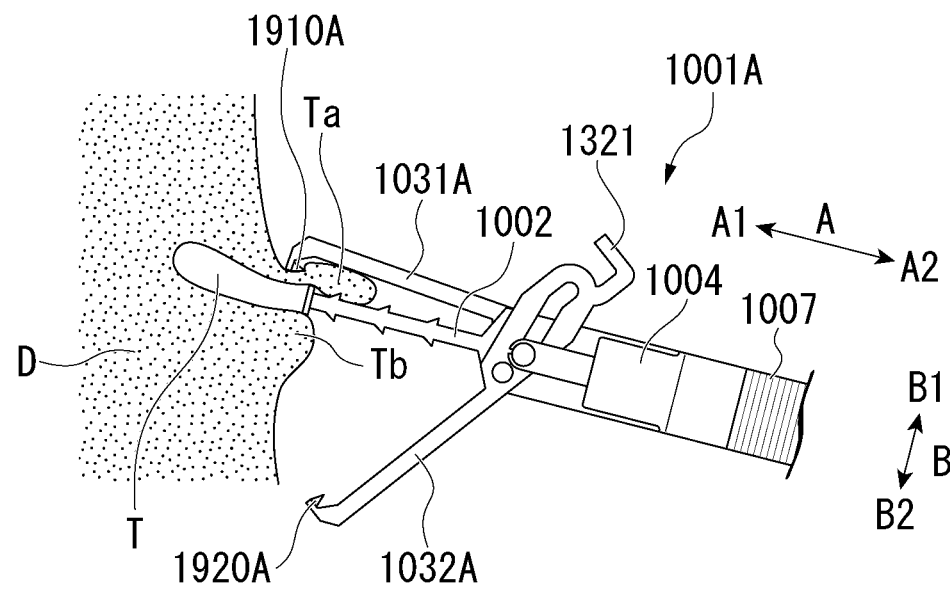

FIG. 45 is a schematic view showing a state of opening the second movable arm and making the treatment portion to approach the tissue to be grasped while the first movable arm of the treatment portion of the clip device is grasping the tissue.

Figure 46:
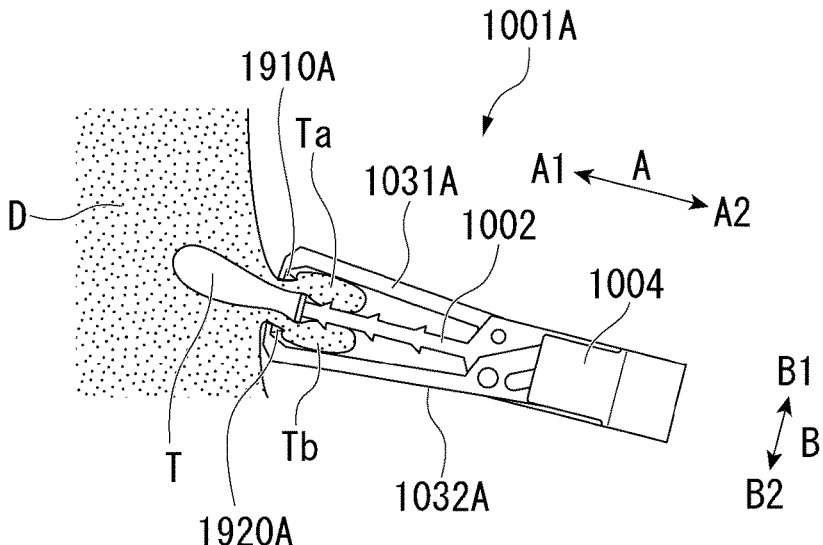

FIG. 46 is a schematic view showing a state of closing the second movable arm of the treatment portion of the clip device to indwell the treatment portion from the clip device in a state in which the treatment portion is grasping the tissue.

Figure 47:
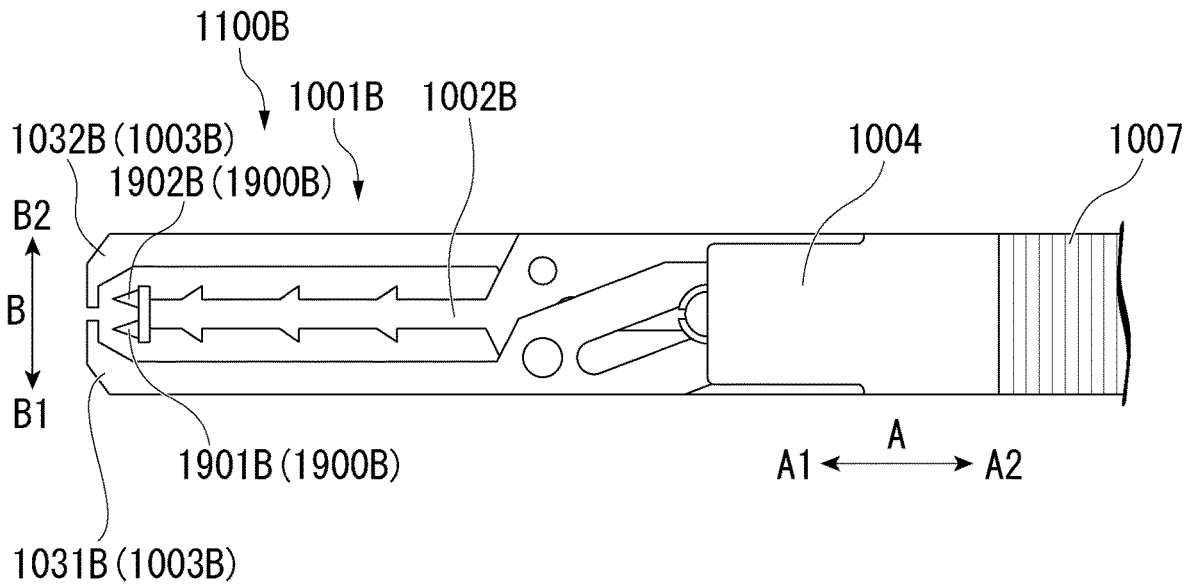

FIG. 47 is a view showing a state in which a treatment portion of a clip device according to a fifth embodiment of the present disclosure is closed.

Figure 48:
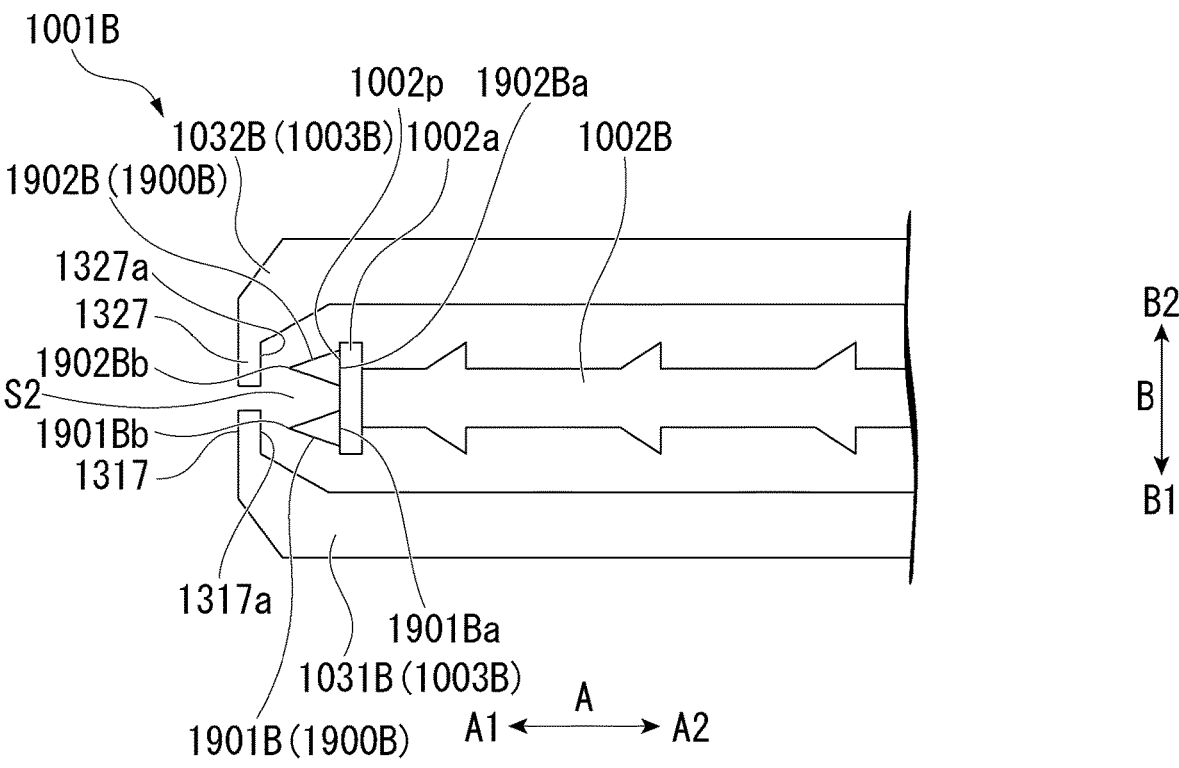

FIG. 48 is an enlarged view showing a distal-end side of the treatment portion of the clip device.

Figure 49:
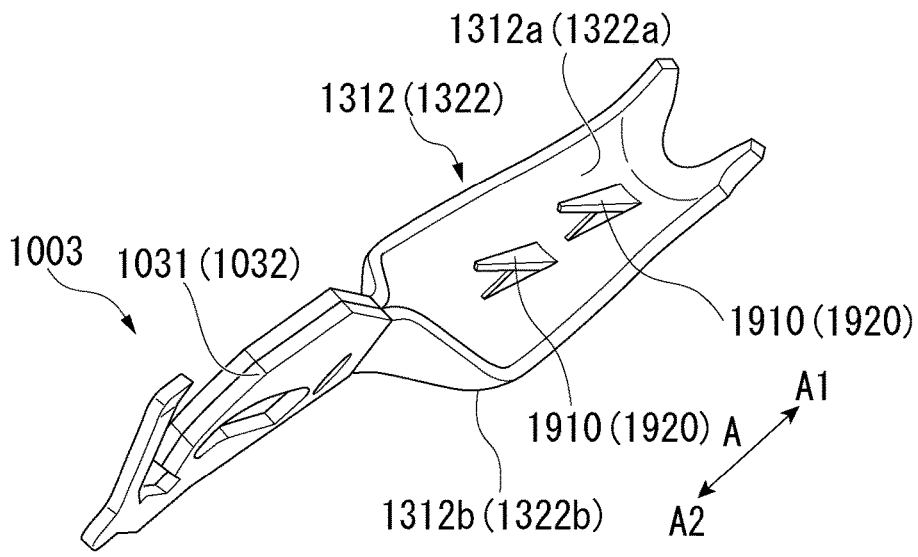

FIG. 49 is a view showing another modification example of treatment portion of the clip device according to the present disclosure.

Figure 50:
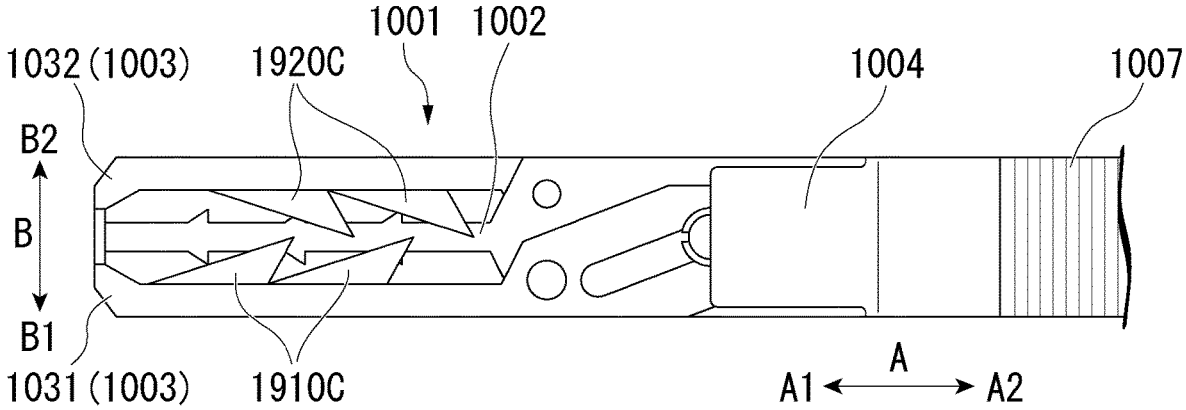

FIG. 50 is a view showing another modification example of treatment portion of the clip device according to the present disclosure.

Figure 51:
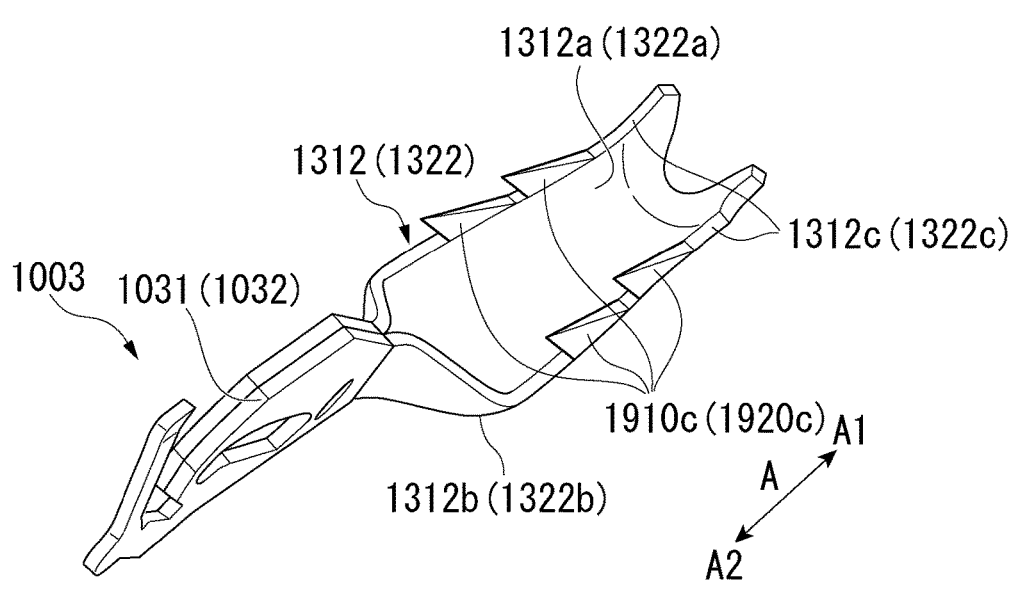

FIG. 51 is a view showing the same modification example of treatment portion of the clip device according to the present disclosure.

Figure 52:
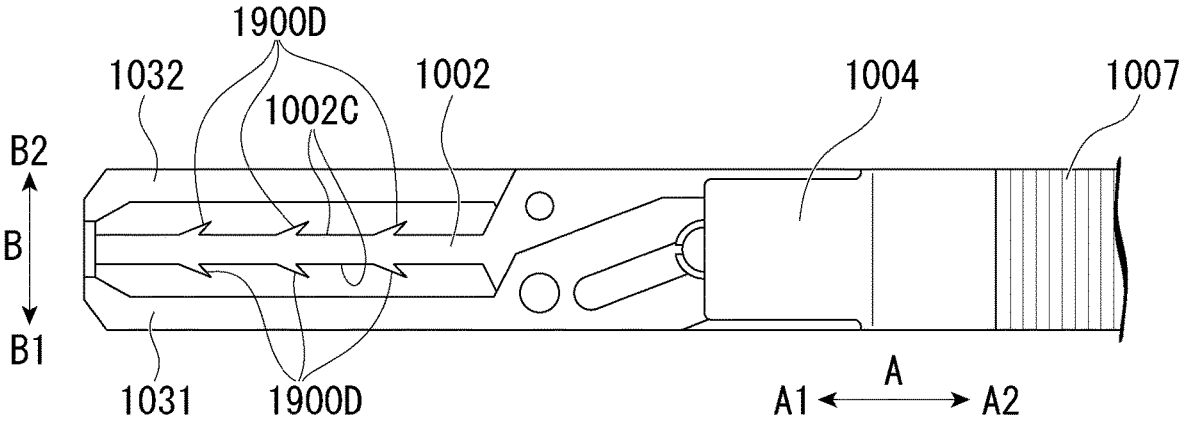

FIG. 52 is a view showing another modification example of treatment portion of the clip device according to the present disclosure.

Figure 53:
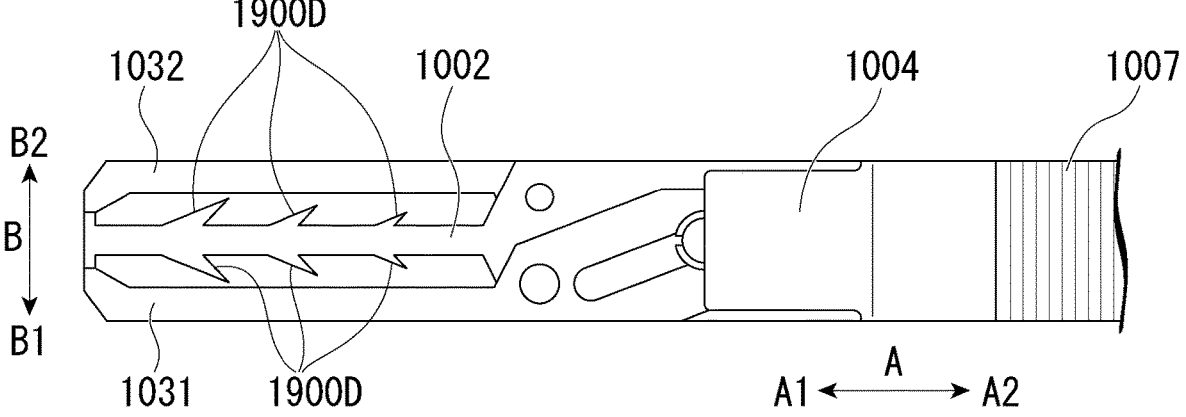

FIG. 53 is a view showing another modification example of treatment portion of the clip device according to the present disclosure.

Figure 54:
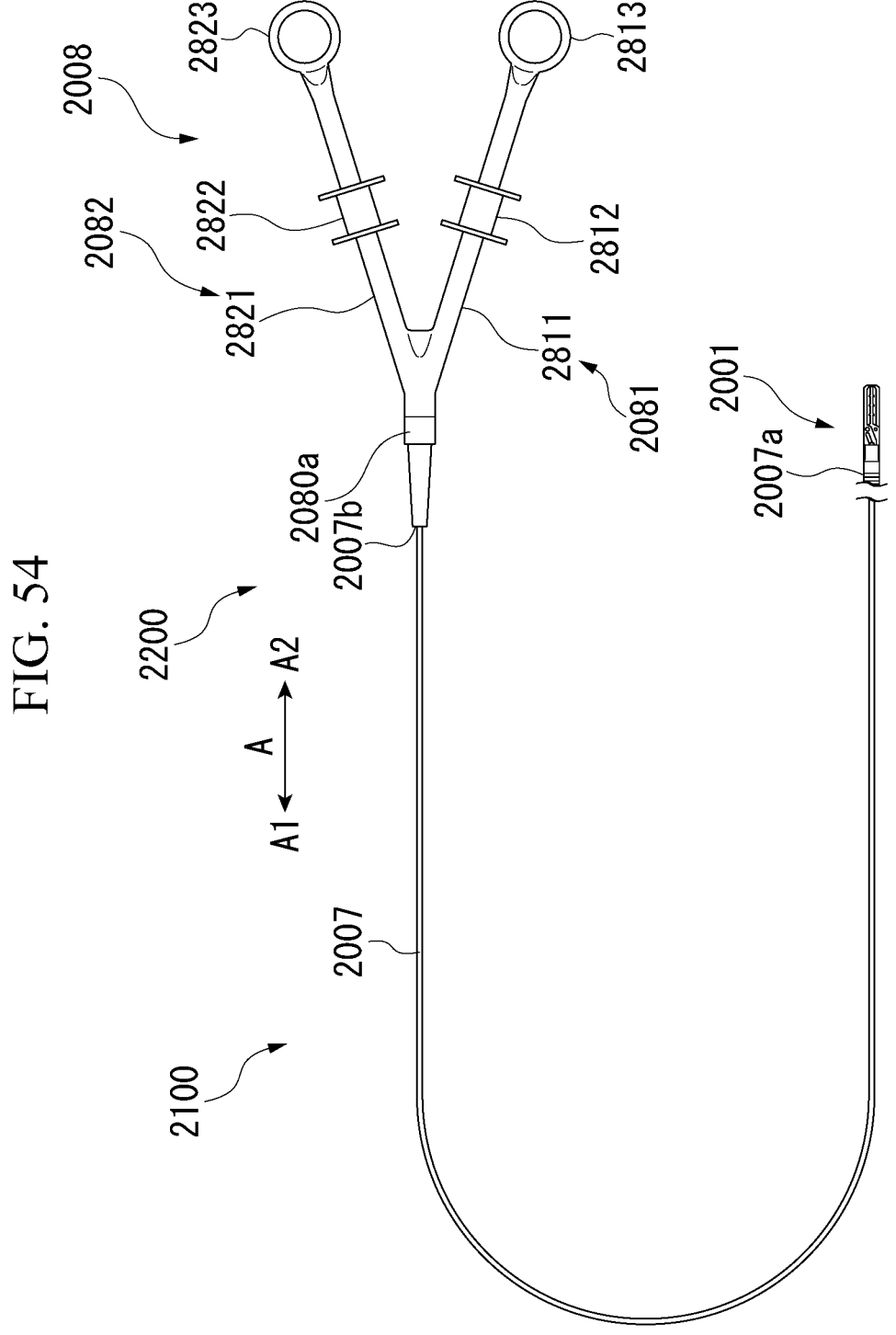

FIG. 54 is a view showing an overall configuration of a clip device according to a sixth embodiment of the present disclosure.

Figure 55:
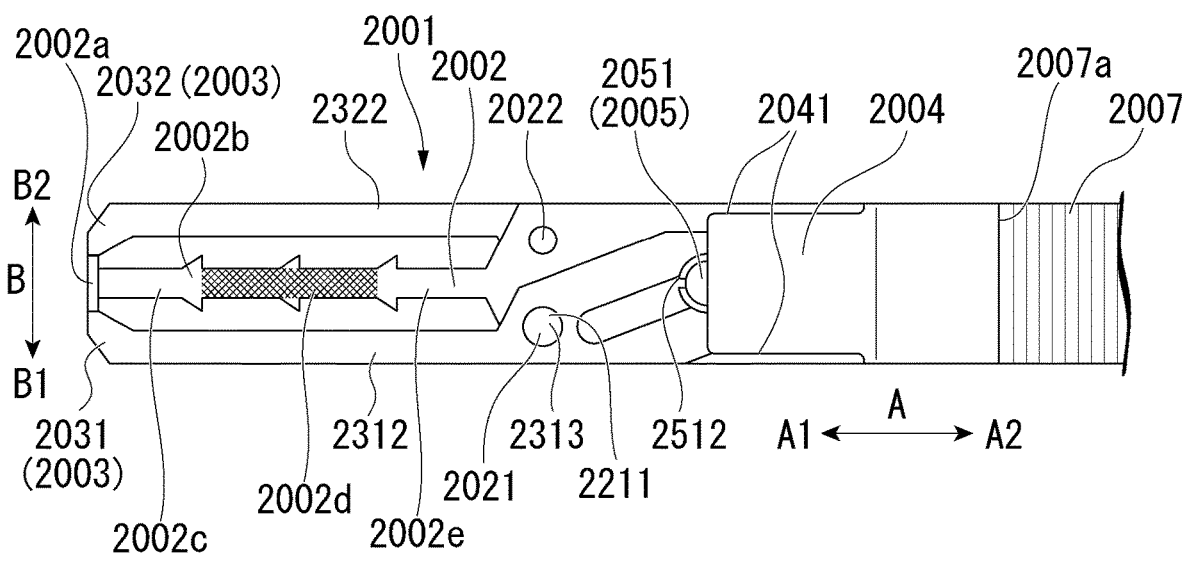

FIG. 55 is a view showing a state in which a treatment portion of the clip device is closed.

Figure 56:
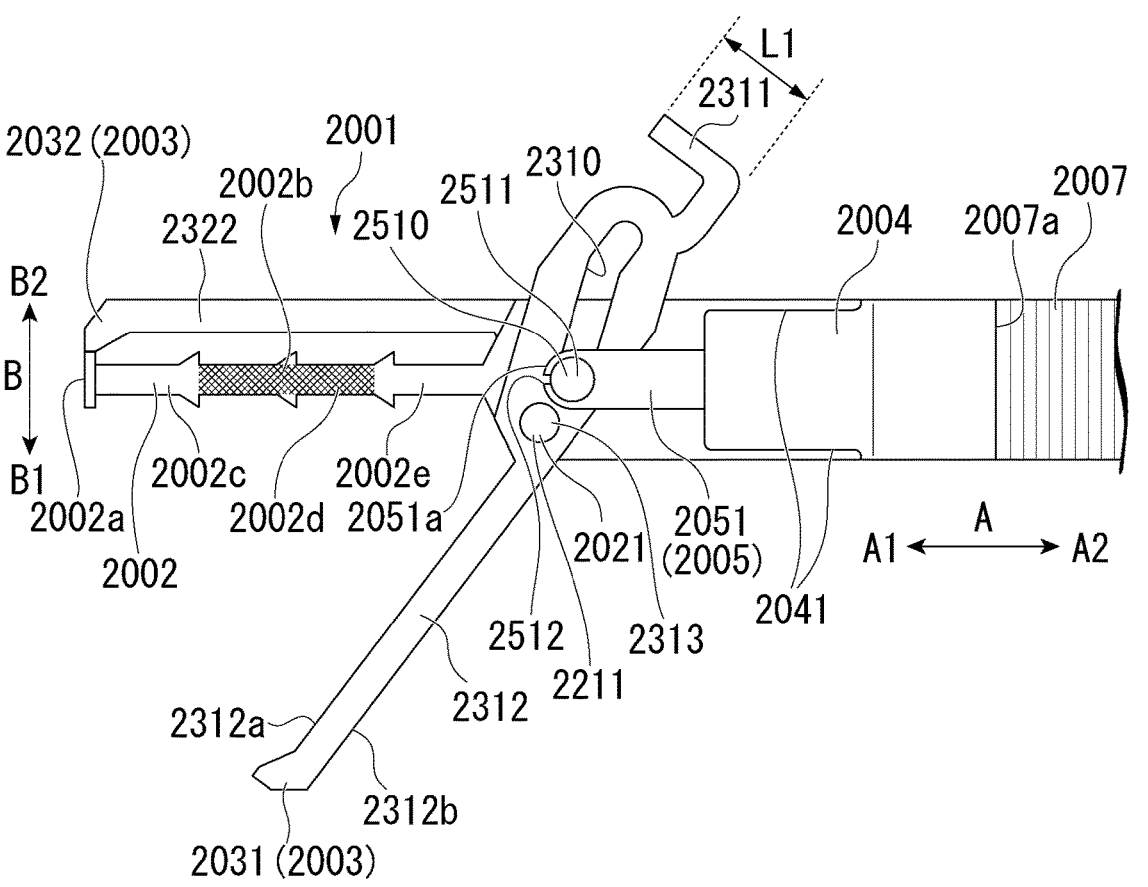

FIG. 56 is a view showing a state in which a first movable arm of the treatment portion of the clip device is opened when viewed from a left side of a thickness direction.

Figure 57:
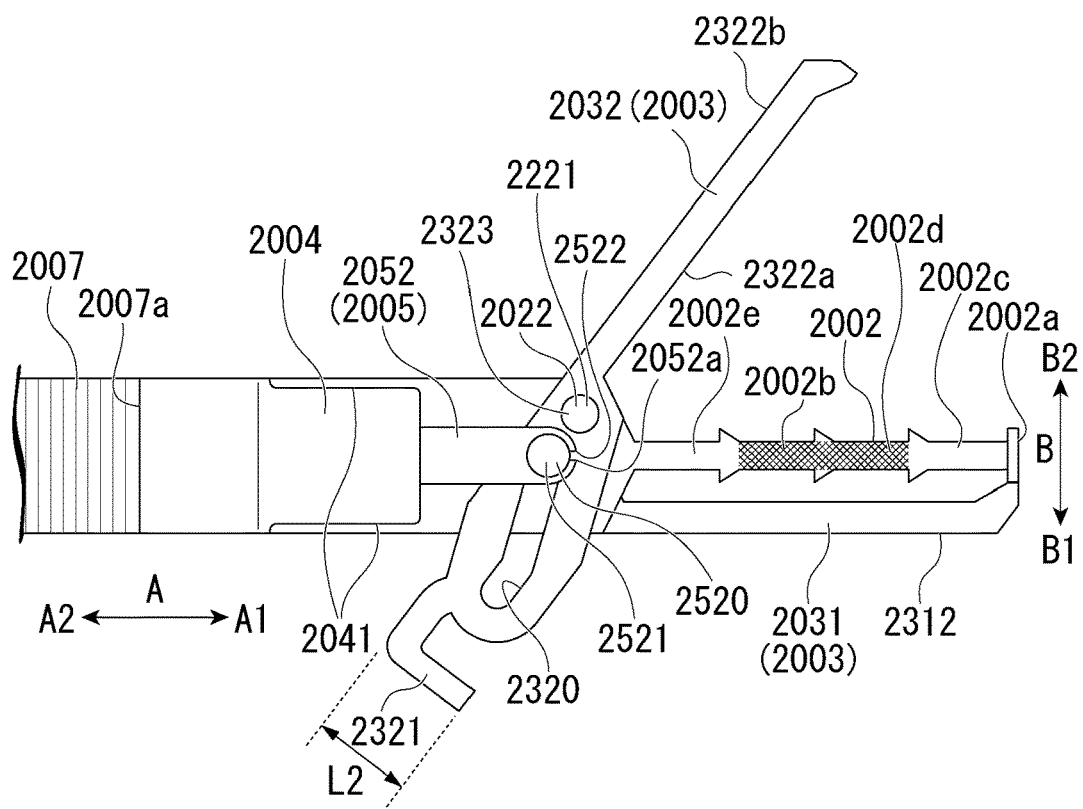

FIG. 57 is a view showing a state in which a second movable arm of the treatment portion of the clip device is opened when viewed from a right side of the thickness direction.

Figure 58:
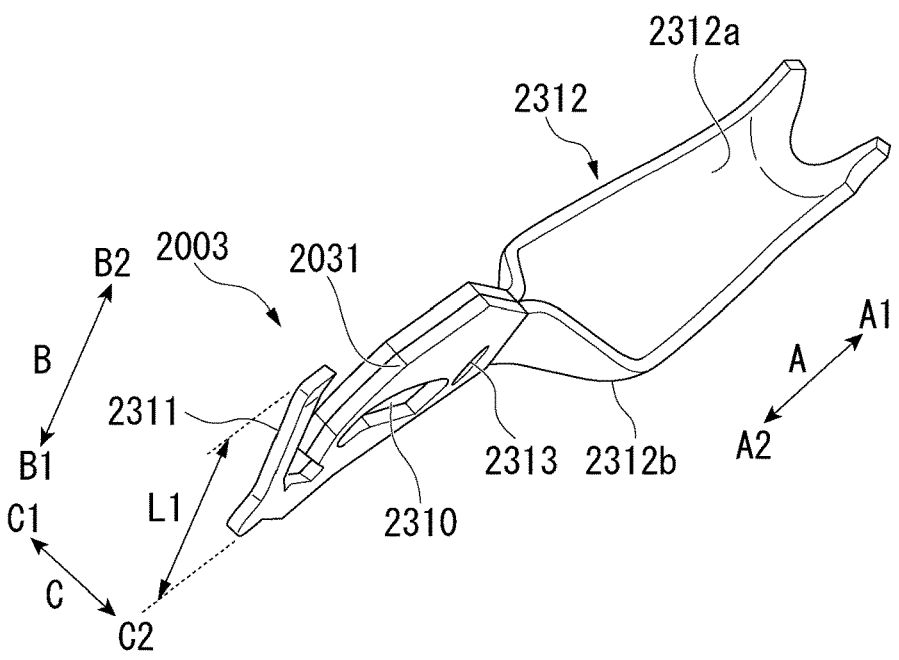

FIG. 58 is a view showing the first movable arm of the treatment portion of the clip device.

Figure 59:
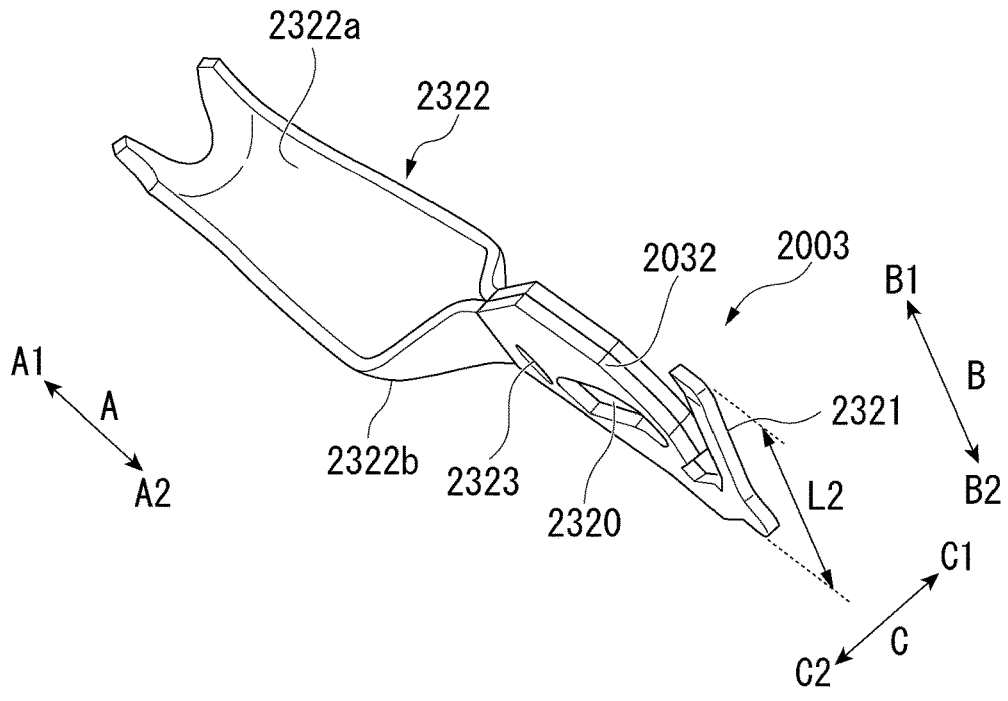

FIG. 59 is a view showing the second movable arm of the treatment portion of the clip device.

Figure 60:
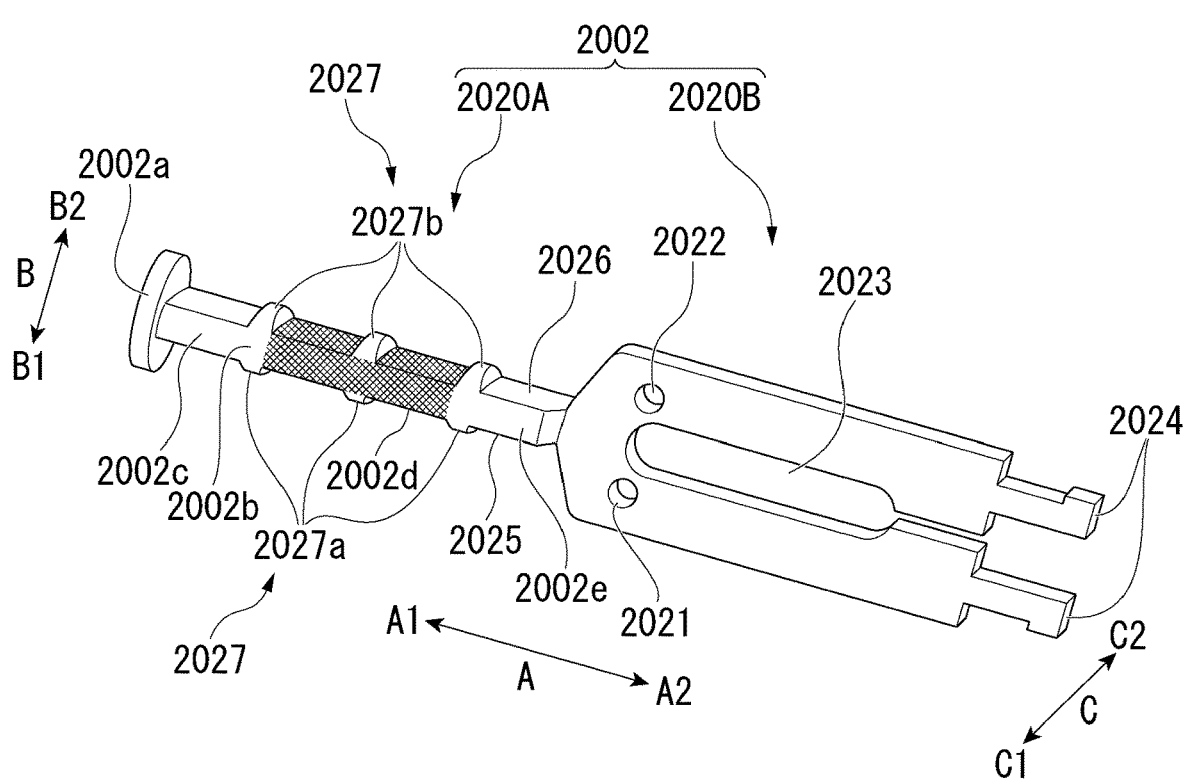

FIG. 60 is a view showing a fixed arm of the treatment portion of the clip device.

Figure 61:
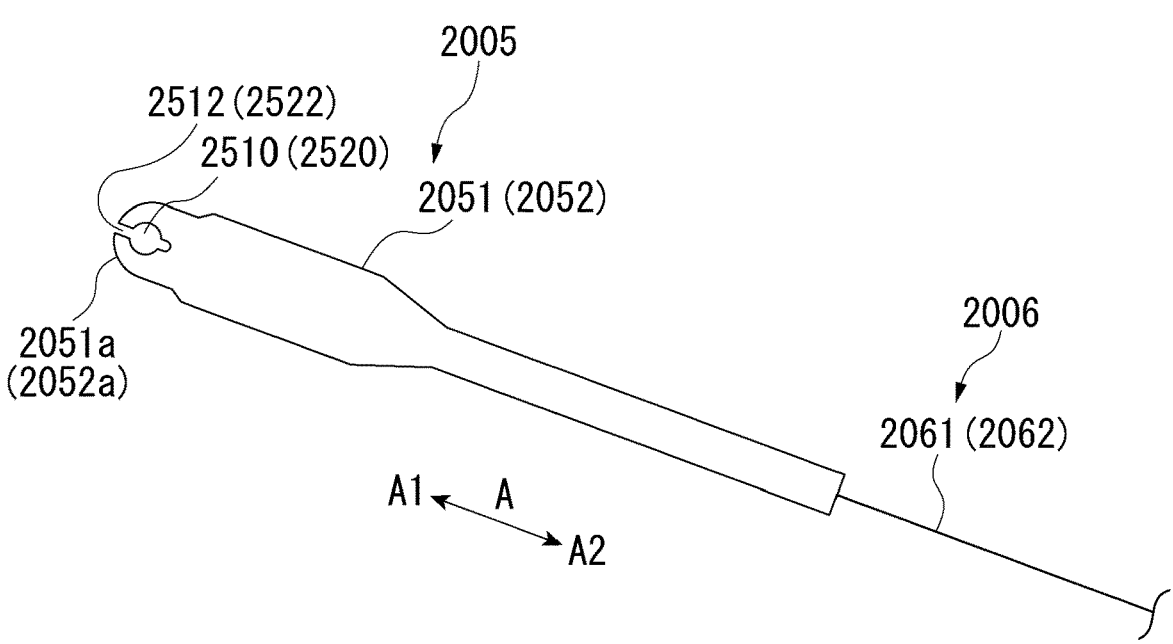

FIG. 61 is a view showing a traction member of an applicator of the clip device.

Figure 62:
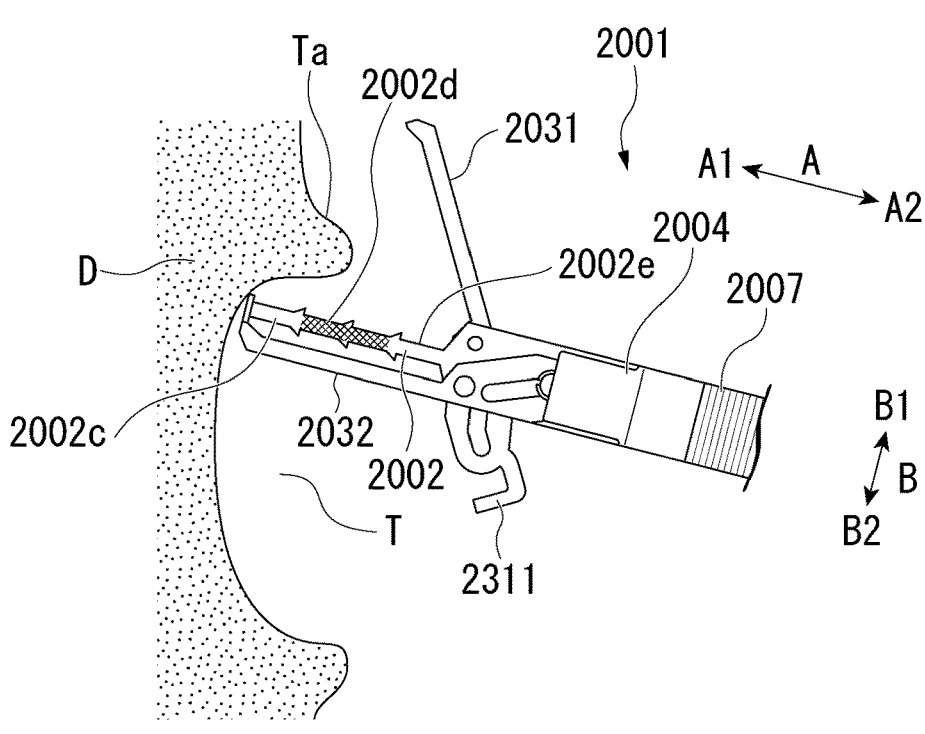

FIG. 62 is a schematic view showing a state of opening the first movable arm of the treatment portion of the clip device and moving the treatment portion to approach the tissue to be grasped.

Figure 63:
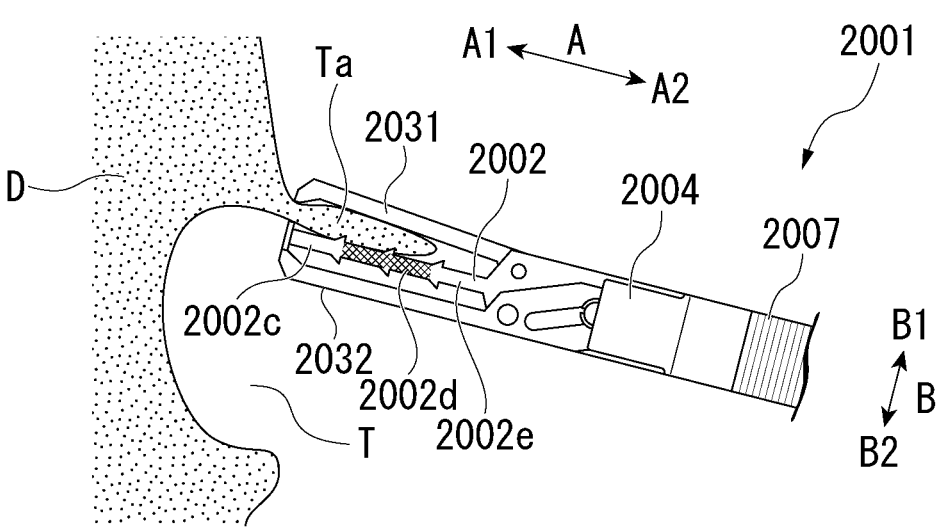

FIG. 63 is a schematic view showing a state of closing the first movable arm of the treatment portion of the clip device to grasp the tissue.

Figure 64:
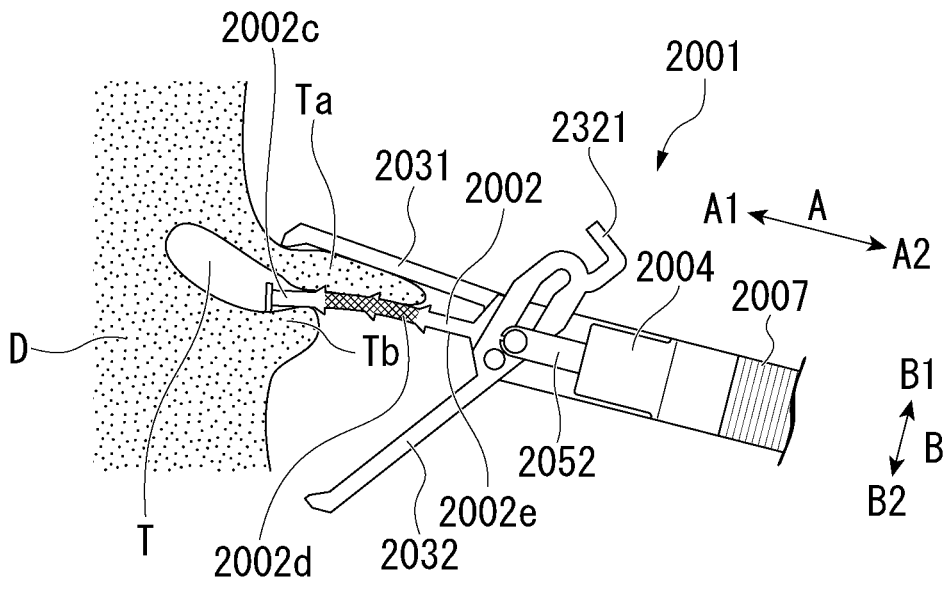

FIG. 64 is a schematic view showing a state of opening the second movable arm and moving the treatment portion to approach the tissue to be grasped while the first movable arm of the treatment portion of the clip device is grasping the tissue.

Figure 65:
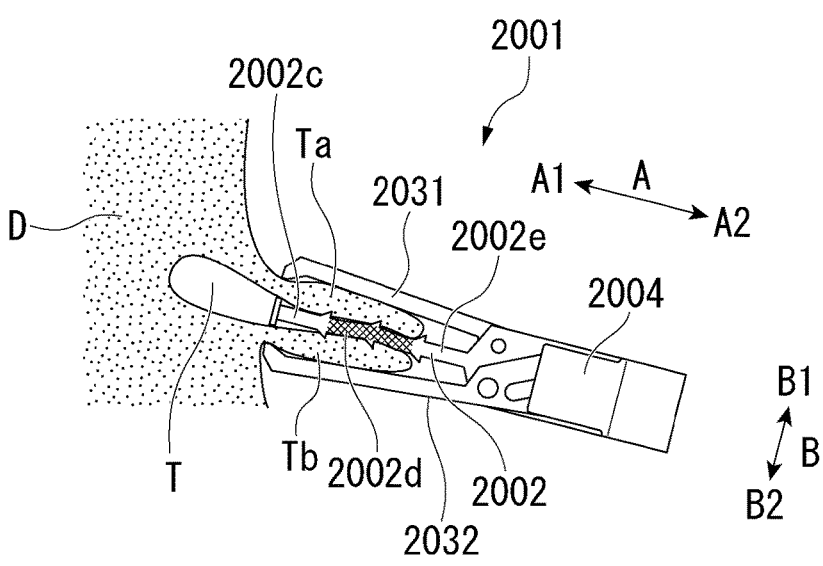

FIG. 65 is a schematic view showing a state of closing the second movable arm of the treatment portion of the clip device to indwell the treatment portion from the clip device in the state in which the treatment portion is grasping the tissue.

Figure 66:
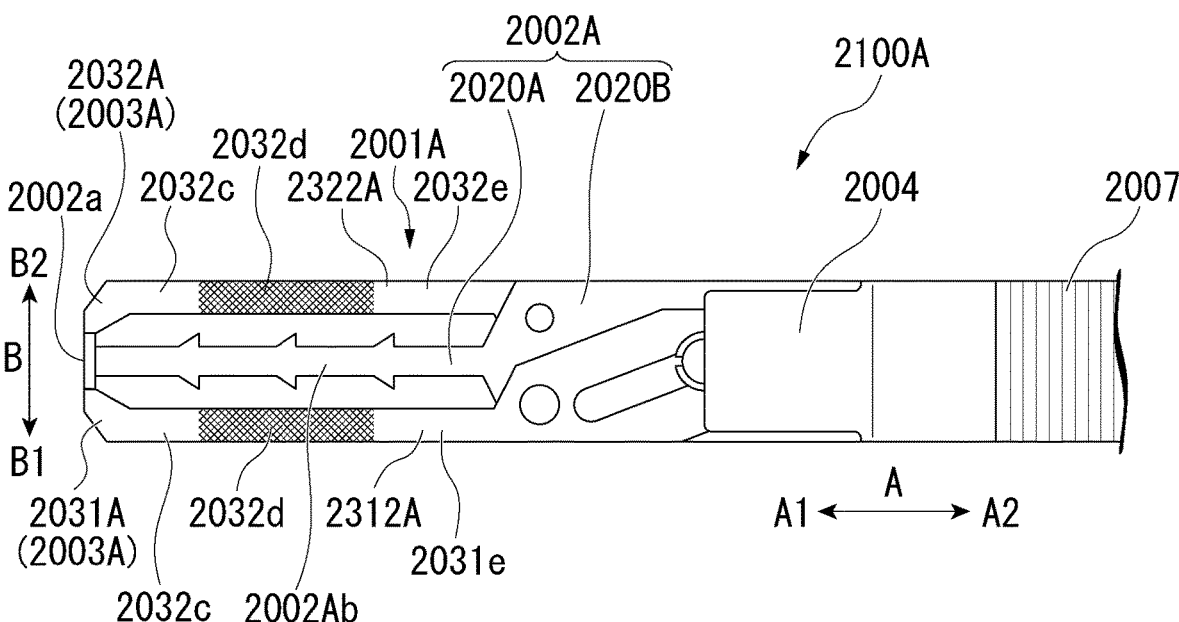

FIG. 66 is a view showing a state in which a treatment portion of a clip device according to a seventh embodiment of the present disclosure is closed.

Figure 67:
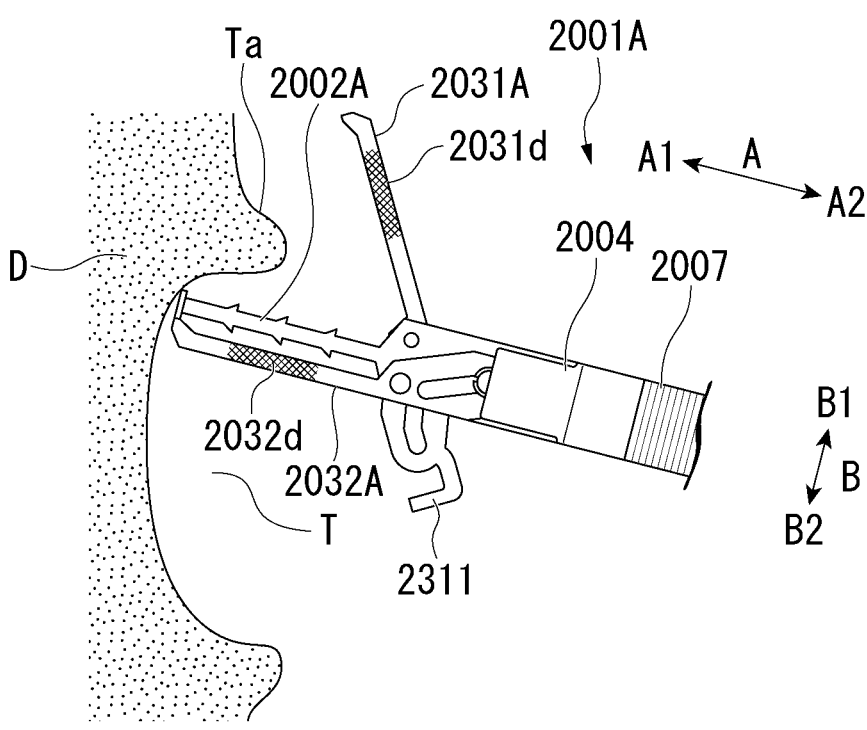

FIG. 67 is a schematic view showing a state of opening a first movable arm of the treatment portion of the clip device to make the treatment portion to approach the tissue to be grasped.

Figure 68:
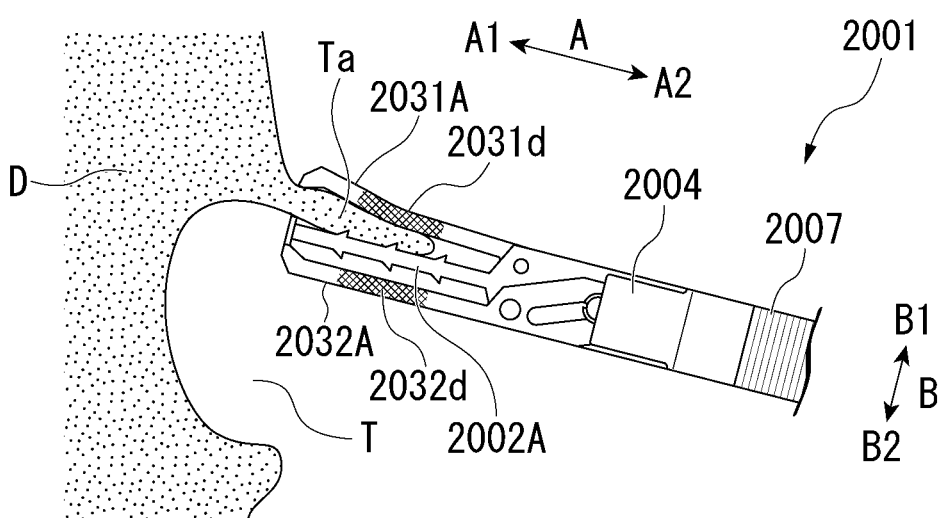

FIG. 68 is a schematic view showing a state of closing the first movable arm of the treatment portion of the clip device and grasping the tissue.

Figure 69:
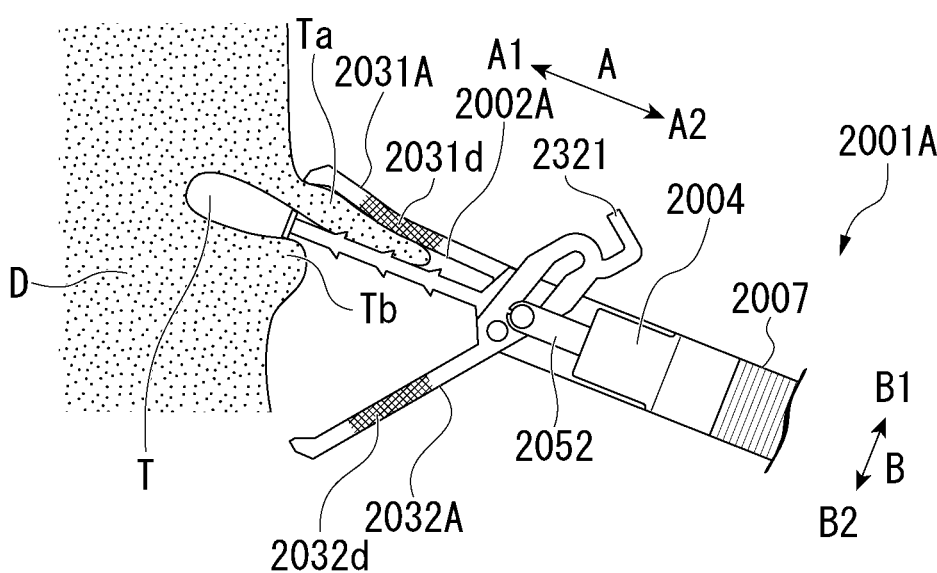

FIG. 69 is a schematic view showing a state of opening the second movable arm and making the treatment portion to approach the tissue to be grasped while the first movable arm of the treatment portion of the clip device is grasping the tissue.

Figure 70:
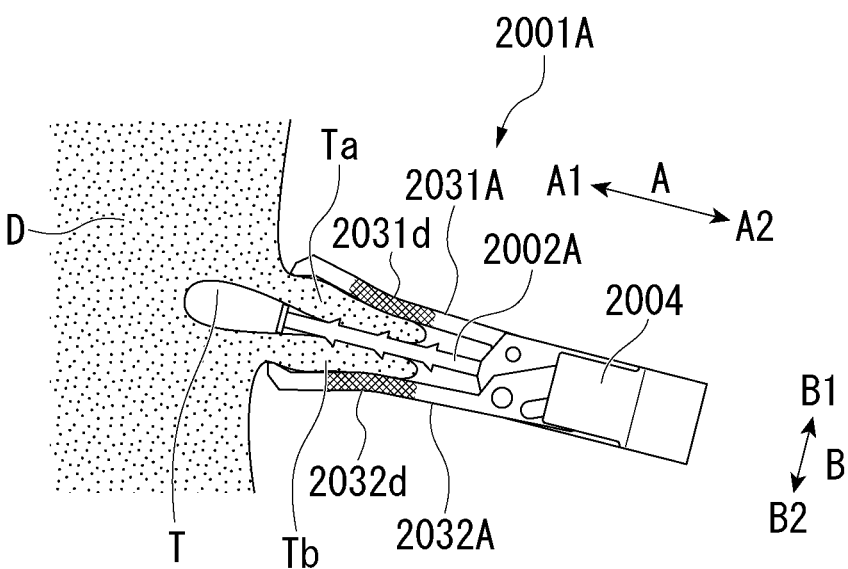

FIG. 70 is a schematic view showing a state of closing the second movable arm of the treatment portion of the clip device to indwell the treatment portion from the clip device in a state in which the treatment portion is grasping the tissue.

Figure 71:
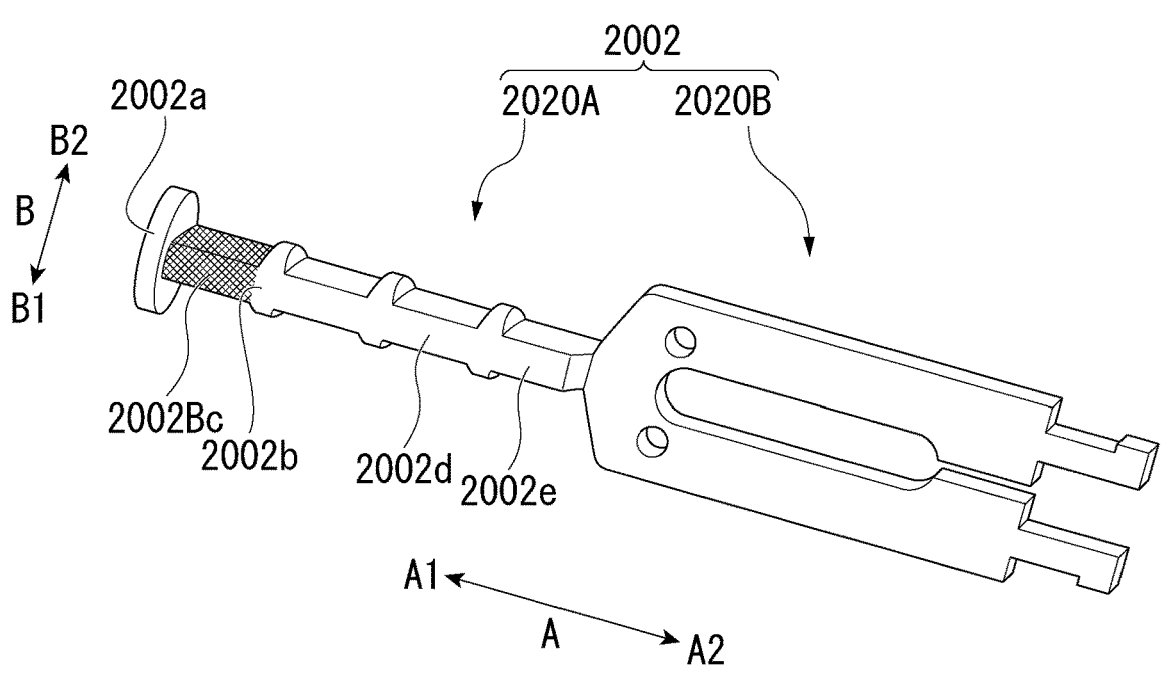

FIG. 71 is a view showing another modification example of treatment portion of the clip device according to the present disclosure.

Figure 72:
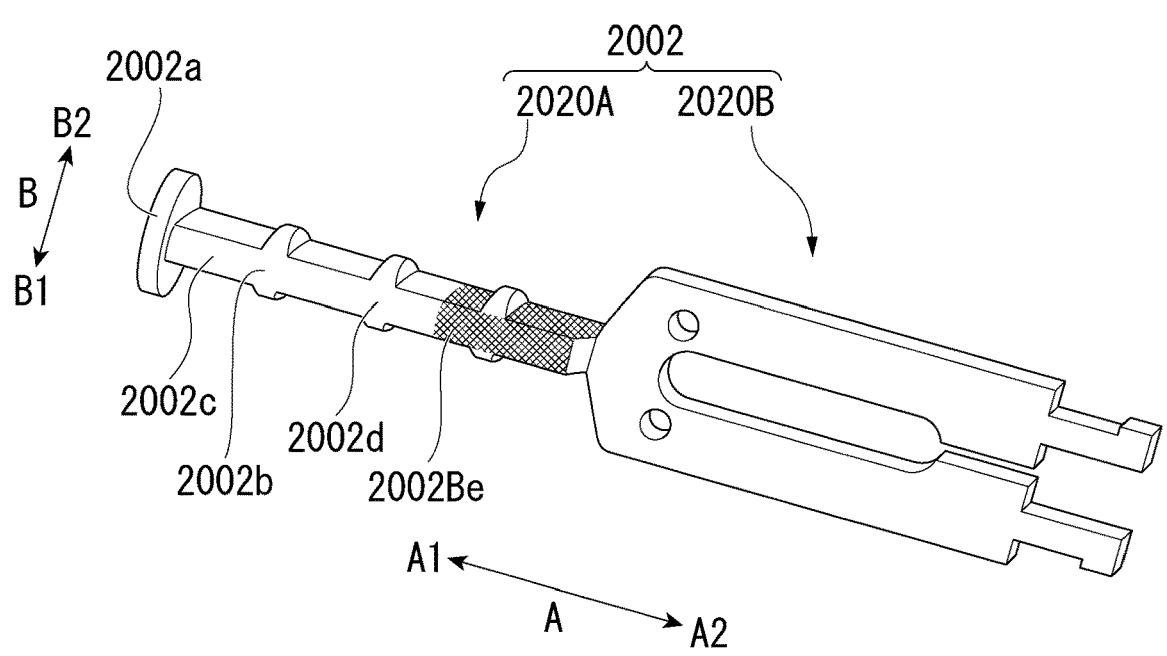

FIG. 72 is a view showing another modification example of treatment portion of the clip device according to the present disclosure.

Figure 73:
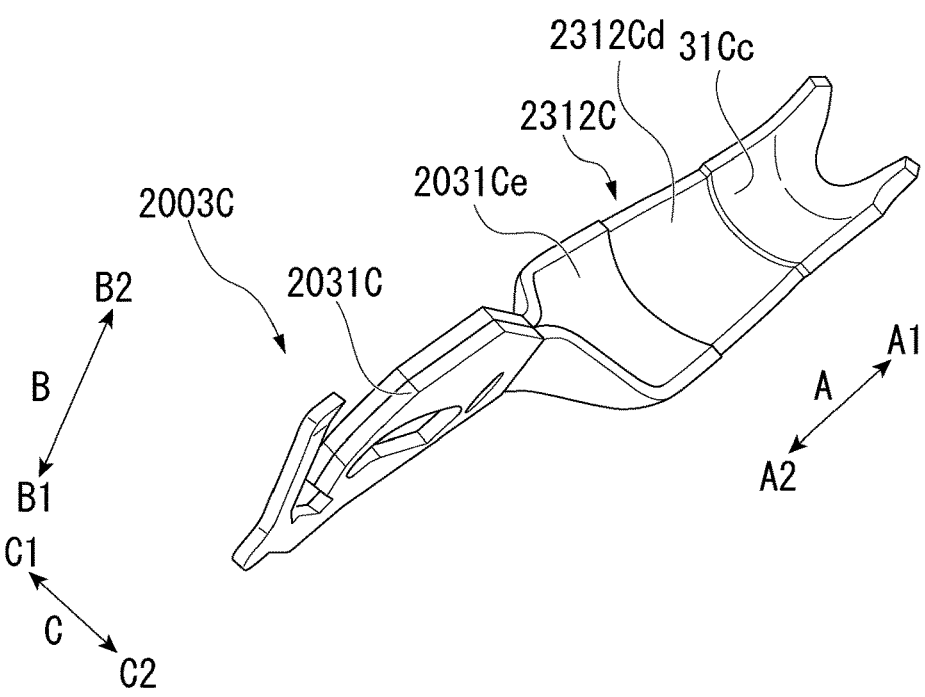

FIG. 73 is a view showing another modification example of treatment portion of the clip device according to the present disclosure.

Figure 74:
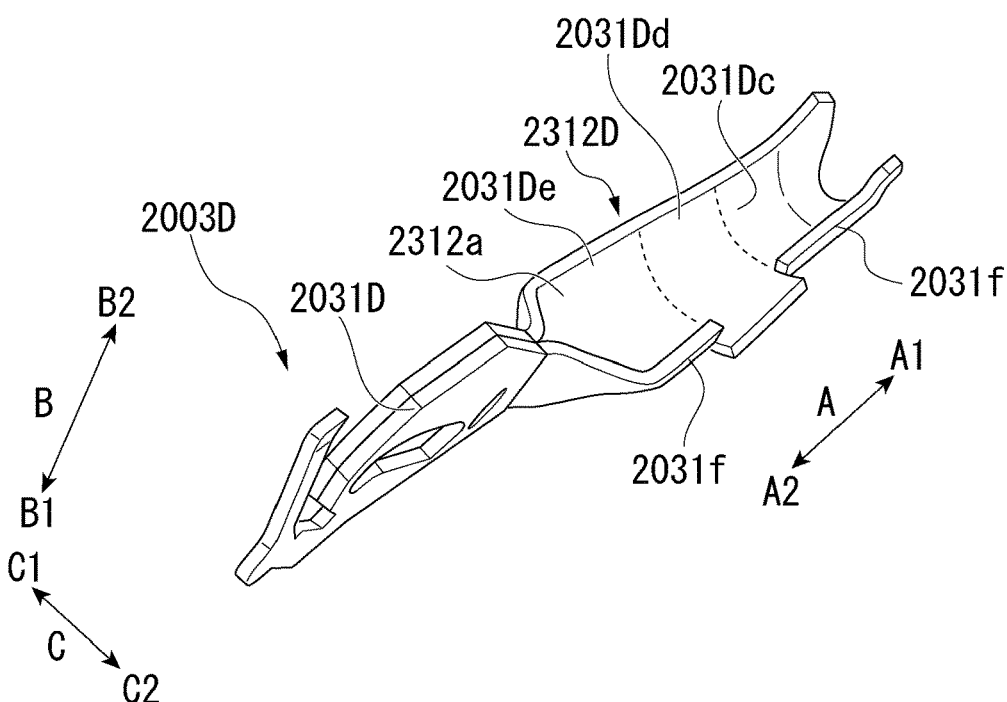

FIG. 74 is a view showing another modification example of treatment portion of the clip device according to the present disclosure.

DETAILED DESCRIPTION

First Embodiment

Figure 1:
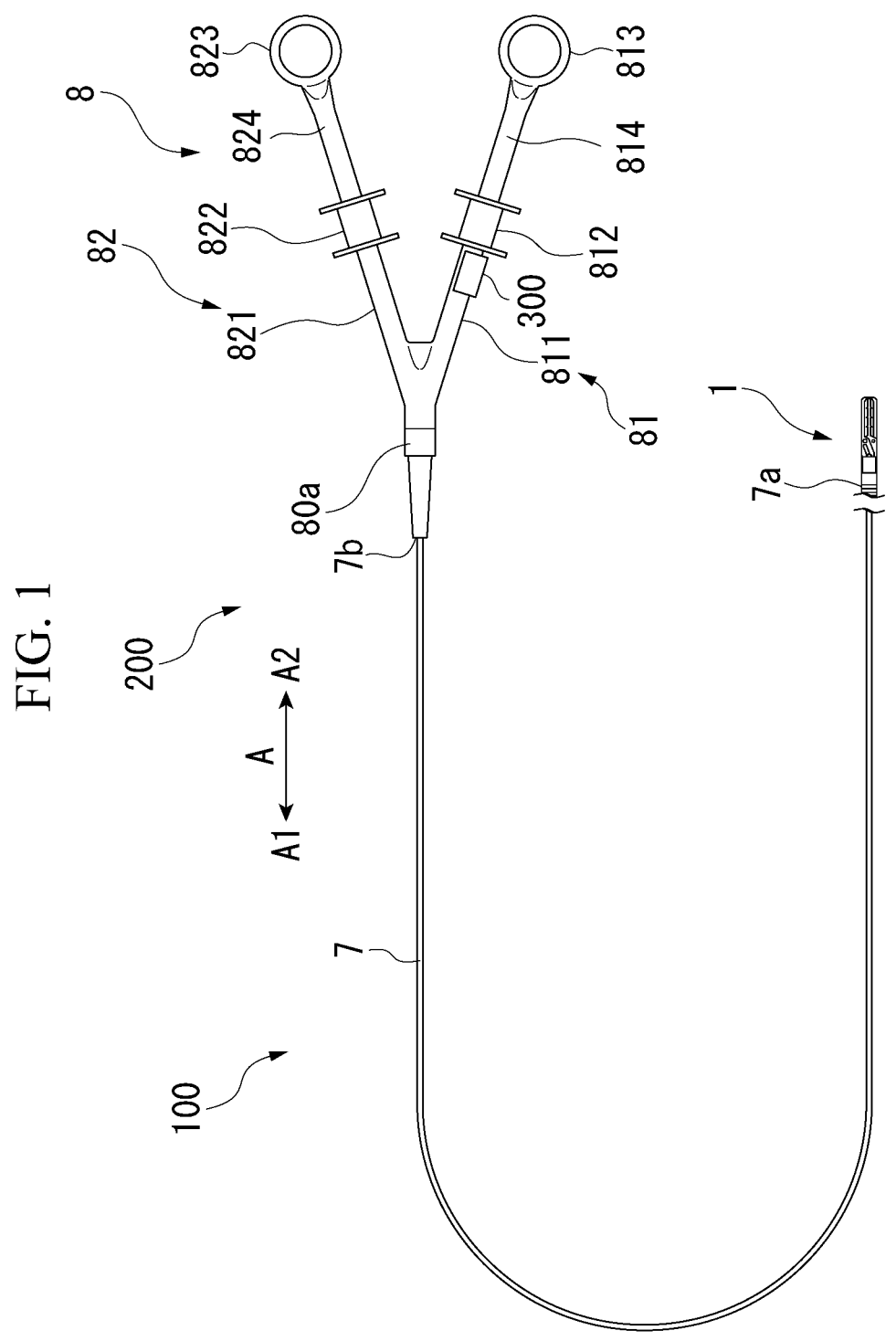
FIG. 1 is a view showing an overall configuration of a clip device according to a first embodiment of the present disclosure.

A clip device (endoscopic treatment device) 100 according to a first embodiment of the present disclosure will be described with reference to FIG. 1 to FIG. 20. FIG. 1 is a view showing the overall configuration of the clip device (endoscopic treatment device) 100 according to the first embodiment of the present disclosure.

Here, in the embodiments and modification examples described below, the same reference signs are given to mutually corresponding configurations, and descriptions of redundant features may be omitted. Also, in the following description, recitations indicating the relative or absolute arrangements such as "parallel", "orthogonal", "center", "coaxial" or the like do not only express such arrangements strictly, but also express a state of relative displacement at an angle or distance that provides the same function. Furthermore, the recitation of "patient" as used herein includes any organism and includes the recitation "tester". The patient may be a human or an animal.

[Clip Device (Endoscopic Treatment Device) 100]

FIG. 1 is a view showing the overall configuration of the clip device (endoscopic treatment device) 100. The clip device 100 includes a treatment portion (clip) 1, an applicator 200 and a stopper 300. The applicator 200 also includes a traction member (connector) 5 (see FIG. 8), an operation wire (wire) 6 (see FIG. 8), a sheath 7, and an operation portion 8. In the following description, the treatment portion 1 side in the longitudinal direction A of the clip device 100 is defined as a tip side (distal-end side) A1 of the clip device 100, and the operation portion 8 side of the applicator 200 of the clip device 100 is defined as base side (proximal-end side) A2 of the clip device. In the clip device 100, the treatment portion 1, the traction member 5 of the applicator 200, the operation wire 6, the sheath 7 and the operation portion 8 are arranged in this sequence from the distal-end side A1 to the proximal-end side A2 of the clip device 100.

The clip device 100 is used, for example, together with an endoscope (not shown). More specifically, the clip device 100 is configured such that it is possible to introduce the treatment portion 1 to the vicinity of the living tissue in the luminal cavity as a treatment object to perform the treatment relative to the living tissue by the surgeon operating the operation portion 8 of the applicator 200 to insert the sheath 7 and the treatment portion 1 provided at the distal-end side A1 of the sheath 7 into a treatment device channel formed in the endoscope. In the present embodiment, the endoscope used with the clip device 100 may be any flexible endoscope.

(Treatment Portion (Clip) 1)

Figure 2:
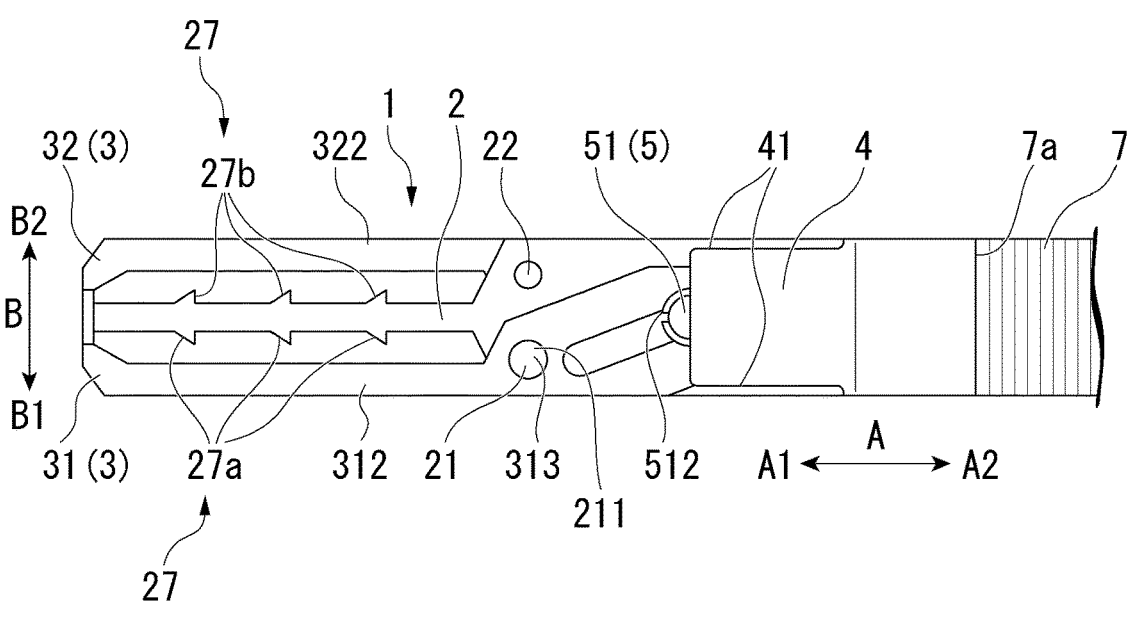
FIG. 2 is a view showing a state in which a treatment portion of the clip device is closed.

FIG. 2 is a view showing a state in which the treatment portion 1 of the clip device 100 is closed.

The treatment portion (clip) 1 is used as a useful clip for patient therapeutic procedures such as performing hemostasis of tissues, closing perforations and hemostasis, suture contraction of internal wounds, marking lesions and tractions (mucosal protuberance), and other surgical procedures. The treatment portion 1 is detached from the applicator 200 by the operation of the surgeon and indwelled in the luminal cavity. The treatment portion 1 includes a fixed arm (central arm, third arm) 2, a movable arm 3, and a clip holder 4, as shown in FIG. 2. Here, the movable arm 3 has a first movable arm (first arm) 31 and a second movable arm (second arm) 32 that open and close relative to the fixed arm 2. The first movable arm 31 and the second movable arm 32 are provided on both sides of the fixed arm 2 and are arms that open independently in opposite directions.

A direction in which the movable arm 3 of the treatment portion 1 opens and closes relative to the fixed arm 2 is defined as an open-close direction B or an up-down direction B, and a direction in which the first movable arm 31 opens to be separated away from the fixed arm 2 is defined as an upper side B1. Also, a direction in which the second movable arm 32 opens to be separated away from the fixed arm 2 is defined as a lower side B2. A direction orthogonal to the longitudinal direction A and the open-close direction B is defined as a thickness direction C or a left-right direction C. In the following description, there are cases in which the open-close direction B is referred to as an open direction B or a close direction B.

[Fixed Arm (Central Arm, Third Arm) 2]

Figure 7:
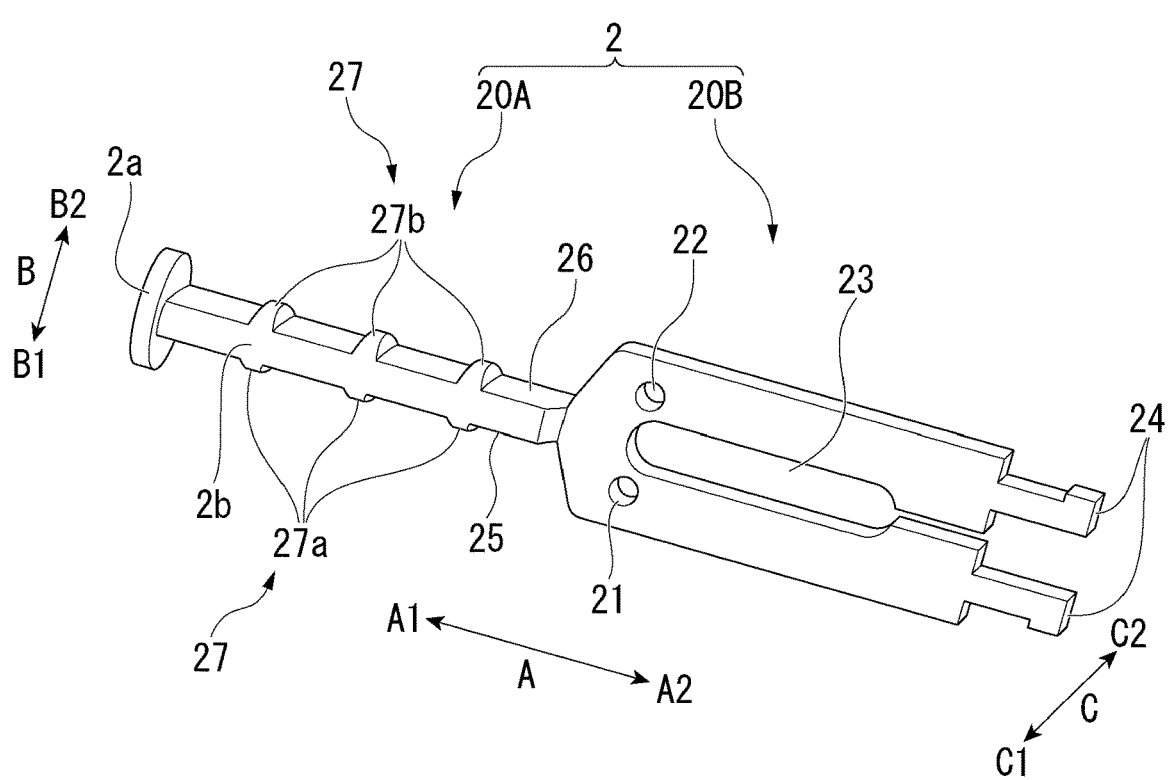
FIG. 7 is a view showing a fixed arm of the treatment portion of the clip device.

FIG. 7 is a view showing the fixed arm (central arm, third arm) 2 of the treatment portion 1 of the clip device 100.

The fixed arm (central arm, third arm) 2 is a rod-shaped member provided between the movable arms 3 along the longitudinal direction A, as shown in FIG. 2 and FIG. 7. The fixed arm 2 has a rod portion 20A formed on the distal-end side A1 and a connection portion 20B formed on the proximal-end side A2.

The rod portion 20A is, for example, a substantially round rod-shaped member made of a material having biocompatibility, as shown in FIG. 7. The rod portion 20A is exposed on its entire outer surface and can come into contact with the tissue. The rod portion 20A includes a distal-end portion 2a and a rod-shaped portion 2b.

The distal-end portion 2a is provided at the distal end the rod-shaped portion 2b. The distal-end portion 2a is formed in a substantially disc shape having a diameter larger than that of the rod-shaped portion 2b. Therefore, the fixed arm 2 can be locked to the living tissue by hooking the distal-end portion 2a of the fixed arm 2 to the living tissue.

The rod-shaped portion 2b is a substantially round rod-shaped member, and has the distal-end portion 2a at its distal end. The rod-shaped portion 2b includes a first opposite surface 25, a second opposite surface 26, and a plurality of protrusion portions 27.

The first opposite surface 25 is formed on the rod-shaped portion 2b and faces the first movable arm 31 provided on the upper side B1 in the open-close direction B.

The second opposite surface 26 is formed on the rod-shaped portion 2b and faces the second movable arm 32 provided on the lower side B2 in the open-close direction B.

The plurality of protrusion portions 27 are protrusion portions provided on the fixed arm 2, as shown in FIG. 2 and FIG. 7. The protrusion portion 27 includes a first protrusion portion 27a provided on the first opposite surface 25 and a second protrusion portion 27b provided on the second opposite surface 26. The first protrusion portion 27a protrudes from the first opposite surface 25 toward the first movable arm 31 arranged on the upper side B1 in the open-close direction B. The second protrusion 27b protrudes from the second opposite surface 26 toward the second movable arm 32 arranged on the lower side B2 in the open-close direction B.

The connection portion 20B is provided on the proximal-end side A2 of the rod portion 20A. The connection portion 20B is formed in a plate shape, and the plate thickness direction of the connection portion 20B substantially coincides with the thickness direction C. Here, in the thickness direction C, one side of the connection portion 20B is defined as a left side C1. Also, in the thickness direction C, the direction opposite to the left side C1 on one side of the connection portion 20B is defined as a right side C2. The connection portion 20B connects the fixed arm 2 and the movable arm 3 with the clip holder 4 and the traction member 5, which will be described later. The connection portion 20B includes a through hole 21, a through hole 22, an engagement groove 23, and a tail 24, as shown in FIG. 7.

The through hole 21 is a hole penetrating through the connection portion 20B in the thickness direction C. The through hole 21 is formed on the distal-end side A1 of the connection portion 20B. A first rotation pin 211 is engaged with the through hole 21 from the left side C1.

The through hole 22 is a hole penetrating through the connection portion 20B in the thickness direction C. The through hole 22 is formed on the distal-end side A1 of the connection portion 20B. The through hole 22 is provided at substantially the same position as that of the through hole 21 in the longitudinal direction A. A second rotation pin 221 is engaged with the through hole 22 from the right side C2.

The engagement groove 23 is a groove extending along the longitudinal direction A formed in the connection portion 20B. The engagement groove 23 is a groove penetrating the connection portion 20B in the thickness direction C.

The tail 24 is formed on the proximal-end side A2 of the connection portion 20B of the fixed arm 2. The tail 24 is connected to the clip holder 4 which will be described later.

[Movable Arm 3]

Figure 3:
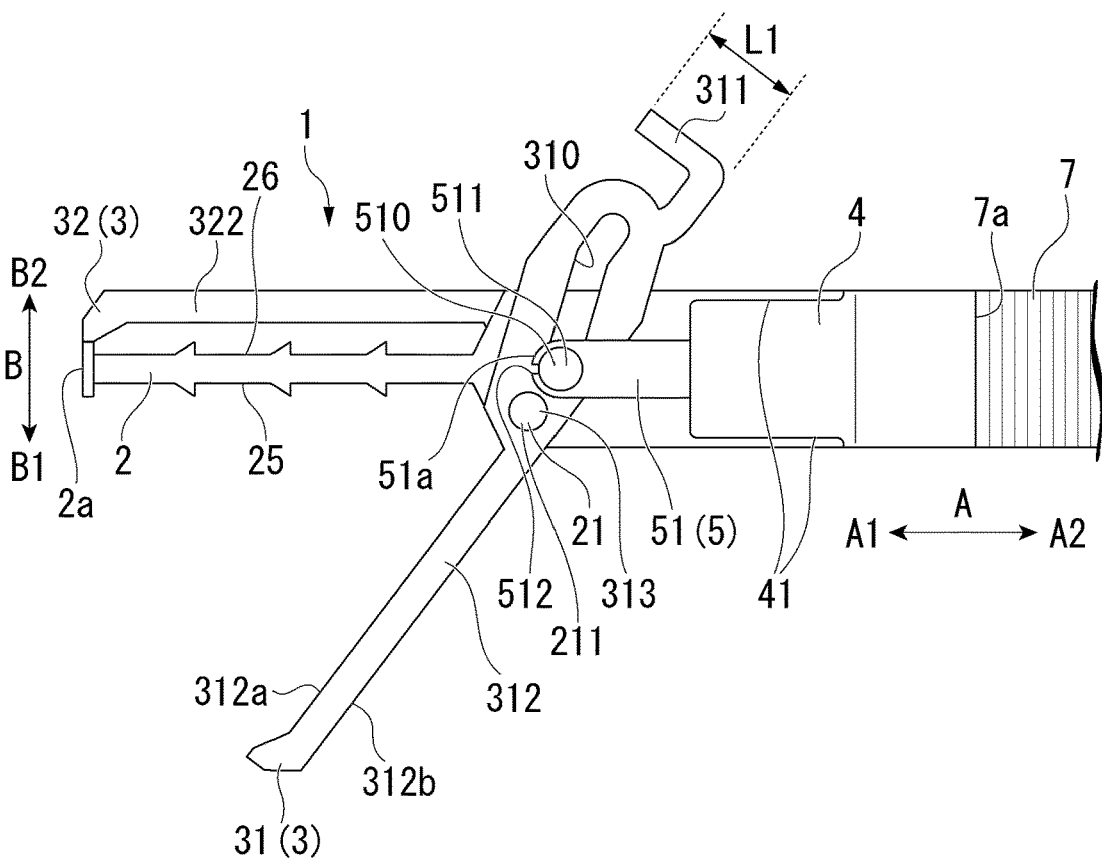
FIG. 3 is a view showing a state in which a first movable arm of the treatment portion of the clip device is opened when viewed from a left side of a thickness direction.
Figure 4:
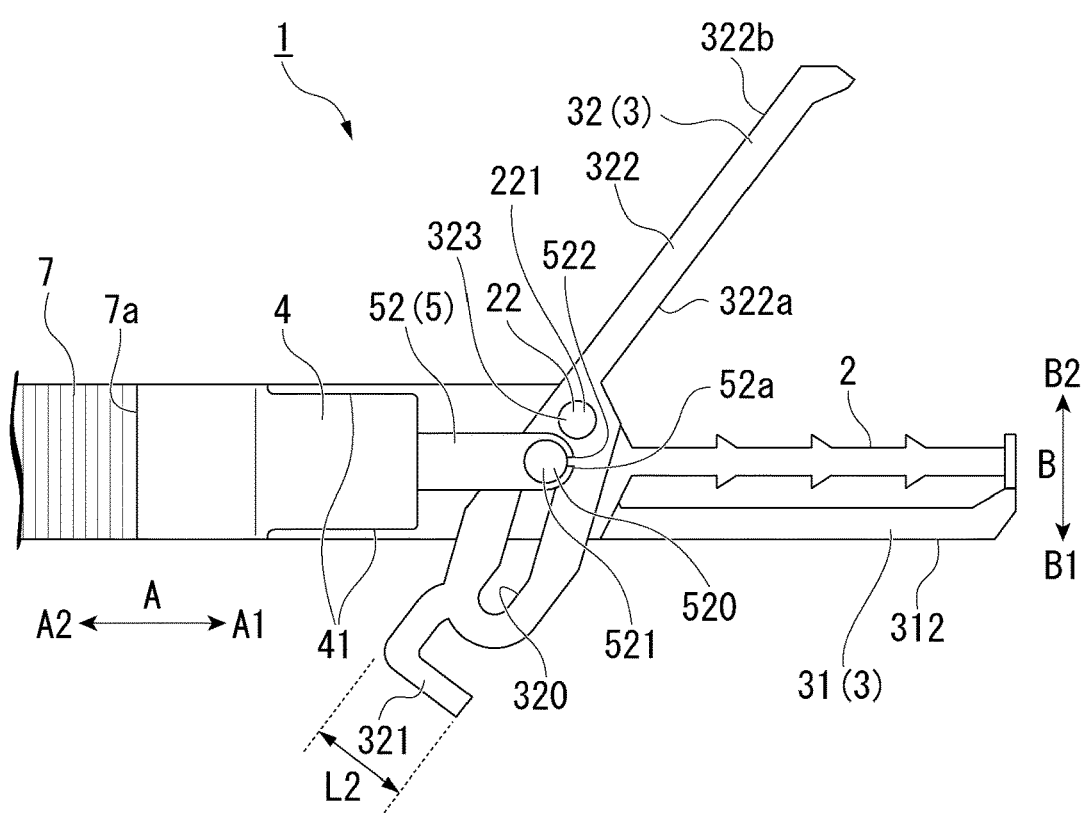
FIG. 4 is a view showing a state in which a second movable arm of the treatment portion of the clip device is opened when viewed from a right side of the thickness direction.
Figure 5:
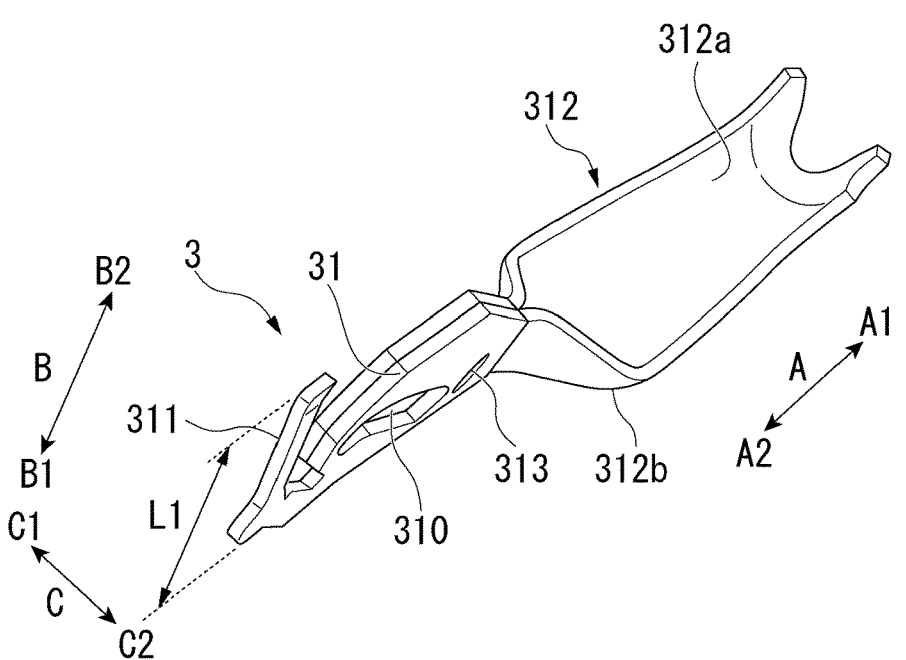
FIG. 5 is a view showing the first movable arm of the treatment portion of the clip device.
Figure 6:
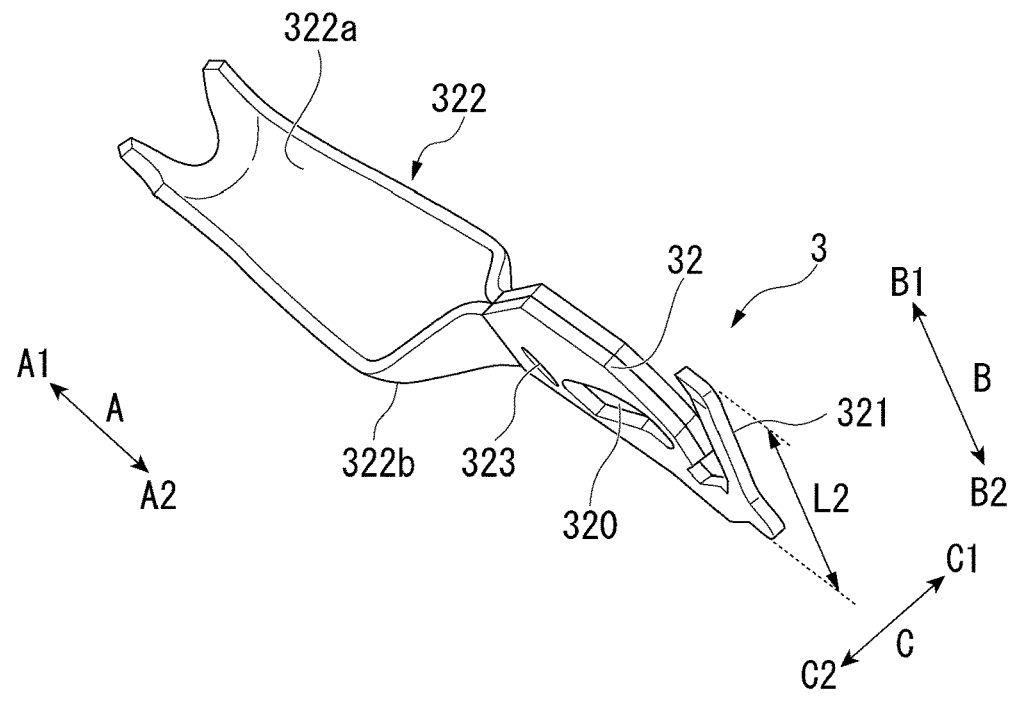
FIG. 6 is a view showing the second movable arm of the treatment portion of the clip device.

FIG. 3 is a view showing a state in which the first movable arm (first arm) 31 of the treatment portion 1 of the clip device 100 is opened when viewed from the left side C1 in the thickness direction C. FIG. 4 is a view showing a state in which the second movable arm (second arm) 32 of the treatment portion 1 of the clip device 100 is opened when viewed from the right side C2 in the thickness direction C. FIG. 5 is a view showing the first movable arm 31 of the treatment portion 1 of the clip device 100. FIG. 6 is a view showing the second movable arm 32 of the treatment portion 1 of the clip device 100. The movable arm 3 has the first movable arm 31 and the second movable arm 32, as shown in FIG. 2 to FIG. 6. The first movable arm 31 is arranged on the upper side B1 of the fixed arm 2 in the open-close direction B. The second movable arm 32 is arranged on the lower side B2 of the fixed arm 2 in the open-close direction B. The first movable arm 31 and the second movable arm 32 can be opened and closed independently.

As shown in FIG. 2, FIG. 3 and FIG. 5, the first movable arm (first arm) 31 is provided so as to be able to open and close relative to the upper side B1 in the open-close direction B relative to the fixed arm 2. Specifically, the first movable arm 31 is rotatably attached to the fixed arm 2 by a first rotation pin 211 provided in the first through hole 313. The first movable arm 31 has a first slide slot 310, a first engagement portion 311, a first through hole 313 and a first arm portion 312.

The first slide slot 310 is provided on the proximal-end side A2 of the first movable arm 31, as shown in FIG. 5. The first slide slot 310 engages with a first slide pin 511, which will be described later.

The first engagement portion 311 is an elastic member having elasticity in the open-close direction B provided on the proximal-end side A2 of the first movable arm 31. The first engagement portion 311 is, for example, a leaf spring. The first engagement portion 311 is accommodated inside the clip holder 4 when the first movable arm 31 is closed relative to the fixed arm 2. Specifically, as shown in FIG. 3, in a state in which the first movable arm 31 is opened relative to the fixed arm 2, the first engagement portion 311 is positioned outside the clip holder 4, which will be described later. On the other hand, as shown in FIG. 2, the first engagement portion 311 is accommodated inside the clip holder 4 when the first movable arm 31 is closed relative to the fixed arm 2. In the state in which the first movable arm 31 is closed relative to the fixed arm 2, a length L1 of the first engagement portion 311 in the open-close direction B is substantially equal to or slightly larger than the inner diameter of the clip holder 4.

In the present embodiment, when the first movable arm 31 transitions from the closed state to the open state relative to the fixed arm 2 in the open-close direction B, the first engagement portion 311 rotates together with the first movable arm 31, and the most proximal end of the first engagement portion 311 enters the inside of the clip holder 4. During the process of the first engagement portion 311 entering the inside of the clip holder 4, each portion of the first engagement portion 311 that contacts the clip holder 4 may be rounded or processed such as chamfering so as not to damage the inner circumferential surface of the clip holder 4.

The first through hole 313 is a hole penetrating through the first movable arm 31 in the thickness direction C. The first through hole 313 is arranged on the left side C1 of the through hole 21 provided in the fixed arm 2 in the thickness direction C and engages with the first rotation pin 211. The first rotation pin 211 connects the first through hole 313 and the through hole 21. With this configuration, the first movable arm 31 can rotate about the first through hole 313 as a rotation center relative to the fixed arm 2.

By rotating the first arm portion 312 along the open-close direction B relative to the fixed arm 2, the distal-end portion thereof approaches the distal-end portion 2a of the fixed arm 2 and can sandwich the living tissue. The first arm portion 312 has a first grasping surface 312a and a first outer surface 312b.

The first grasping surface 312a is an inner surface that contacts the tissue in the open-close direction B and faces the fixed arm 2. The first outer surface 312b is a surface provided on the side opposite to the first grasping surface 312a in the open-close direction B. In the open-close direction B, the first arm portion 312 is formed with a recess on the side of the first grasping surface 312a and a rounded bulge on the side of the first outer surface 312b. Therefore, when the tissue is grasped by the first movable arm 31 and the fixed arm 2, the tissue is accommodated in the recess portion included in the first movable arm 31.

The first arm portion 312 is not limited to the shape according to the present embodiment, and can be configured along various conventional structures. For example, the first arm portion 312 may have a claw-shaped distal end portion in order to definitely clamp the living tissue.

As shown in FIG. 2, FIG. 4 and FIG. 6, the second movable arm (second arm) 32 is provided so as to be openable and closable toward the lower end side B2 in the open-close direction B relative to the fixed arm 2. Specifically, the second movable arm 32 is provided to be openable and closable to the side opposite to the first movable arm 31 relative to the fixed arm 2 by means of a second rotation pin 221 provided in the second through hole 323. The second movable arm 32 has a second slide slot 320, a second engaging portion 321, a second through hole 323 and a second arm portion 322.

The second slide slot 320 is provided on the proximal-end side A2 of the second movable arm 32, as shown in FIG. 6. The second slide slot 320 engages with the second slide pin 521, which will be described later.

The second engaging portion 321 is an elastic member provided on the proximal-end side A2 of the second movable arm 32 and having elasticity in the open-close direction B. The second engaging portion 321 is, for example, a leaf spring. The second engaging portion 321 is accommodated inside the clip holder 4 when the second movable arm 32 is closed relative to the fixed arm 2. Specifically, as shown in FIG. 4, when the second movable arm 32 is opened relative to the fixed arm 2, the second engaging portion 321 is positioned outside the clip holder 4, which will be described later. On the other hand, as shown in FIG. 2, the second engaging portion 321 is accommodated inside the clip holder 4 when the second movable arm 32 is closed relative to the fixed arm 2. In the state in which the second movable arm 32 is closed relative to the fixed arm 2, the length L2 of the second engaging portion 321 in the open-close direction B is substantially equal to or substantially larger than the inner diameter of the clip holder 4.

In the present embodiment, when the second movable arm 32 transitions from the closed state to the open state relative to the fixed arm 2 in the open-close direction B, the second engaging portion 321 rotates together with the second movable arm 32, and the second engaging portion 321 enters the inside of the clip holder 4 from the most proximal end of the second engaging portion 321. Each portion of the second engaging portion 321 that contacts the clip holder 4 may be formed in the rounded shape or processed such as the chamfering so as not to damage the inner circumferential surface of the clip holder 4 in the process of the second engaging portion 321 entering the inside of the clip holder 4.

The second through hole 323 is a hole penetrating through the second movable arm 32 in the thickness direction C. The second through hole 323 is arranged on the right side C2 of the through hole 21 provided in the fixed arm 2 in the thickness direction C and engages with the second rotation pin 221. The second rotation pin 221 connects the second through hole 323 and the through hole 22. This configuration allows the second movable arm 32 to be rotatable about the second through hole 323 as a center relative to the fixed arm 2.

By rotating the second arm portion 322 following the open-close direction B relative to the fixed arm 2, the distal-end portion of the second arm portion 332 approaches the distal-end portion 2a of the fixed arm 2 so as to clamp the living tissue. Similar to the first arm portion 312, the second arm portion 322 is not limited to the shape according to the present embodiment, and for example, the distal-end portion thereof may be formed into the claw shape in order to definitely clamp the living tissue. The second arm portion 322 has a second grasping surface 322a and a second outer surface 322b.

The second grasping surface 322a is an inner surface that contacts the tissue in the open-close direction B and faces the fixed arm 2. The second outer surface 322b is a surface provided on the side opposite to the second grasping surface 322a in the open-close direction B. In the open-close direction B, the second arm portion 322 is formed with a recess on the side of the second grasping surface 322a and a rounded bulge on the side of the second outer surface 322b. Therefore, when the tissue is grasped by the second movable arm 32 and the fixed arm 2, the tissue is accommodated in the recess portion of the second movable arm 32.

[Clip Holder 4]

The clip holder 4 is a pipe formed in a cylindrical shape having a longitudinal axis, as shown in FIG. 2. In the present embodiment, the clip holder 4 is arranged along the longitudinal direction A. The clip holder 4 is configured such that at least the proximal-end portions of the movable arm 3 and the fixed arm 2 in the closed state can enter therein. Also, the clip holder 4 rotates together with the first movable arm 31 and the second movable arm 32 when the clip device 100 is rotated in the circumferential direction.

The clip holder 4 has groove portions 41. The groove portions 41 are formed on the distal-end side A1 of the clip holder 4 and on the upper side B1 and the lower side B2 in the open-close direction B. The groove portions 41 are, for example, slits formed from the distal end toward the proximal-end side A2, and have dimensions suitable for the first engagement portion 311 of the first movable arm 31 and the second engaging portion 321 of the second movable arm 32 to enter inside of the clip holder 4.

The clip holder 4 may include an engaging hole (not shown) formed at the base end A2 and with which the pair of tails 24 of the fixed arm 2 can be engaged, for example. Accordingly, the fixed arm 2 is thereby attached to the clip holder 4. The fixed arm 2 and the clip holder 4 may be integrally molded.

The clip holder 4 has an inner diameter equal to or slightly shorter than the length L1 of the first engagement portion 311 and the length L2 of the second engaging portion 321. The clip holder 4 can accommodate the first engagement portion 311 and the second engaging portion 321 inside therein. When the first movable arm 31 rotates toward the lower side B2 in the open-close direction B, the first engagement portion 311 enters the inside of the clip holder 4 through the groove portion 41. Also, when the second movable arm 32 rotates toward the upper side B1 in the open-close direction B, the second engaging portion 321 enters the inside of the clip holder 4 from the groove portion 41. The first movable arm 31 can be opened again relative to the fixed arm 2 until the first engagement portion 311 is engaged to and locked by the clip holder 4. Also, the second movable arm 32 can be opened again relative to the fixed arm 2 until the second engaging portion 321 is engaged to and locked by the clip holder 4.

When the first movable arm 31 rotates further toward the lower side B2 in the open-close direction B in the state in which the first engagement portion 311 is accommodated inside the clip holder 4, the first engagement portion 311 abuts on the inner circumferential surface of the clip holder 4 to be elastically deformed so as to be engaged with and locked inside the clip holder 4. Also, when the second movable arm 32 is further rotated toward the upper side B1 in the open-close direction B in the state in which the second engaging portion 321 is accommodated inside the clip holder 4, the second engaging portion 321 abuts on the inner circumferential surface of the clip holder 4 to be elastically deformed so as to be engaged with and locked inside the clip holder 4. Accordingly, the closed state of the first movable arm 31 and the second movable arm 32 relative to the fixed arm 2 is maintained. It is noted that the clip holder 4 can at first lock either one of the first engagement portion 311 and the second engaging portion 321.

[Applicator 200]

The applicator 200 is a portion of the clip device 100 that is not indwelled in the luminal cavity except for the treatment portion 1. The applicator 200 includes a traction member (connector) 5, an operation wire 6, a sheath 7, and an operation portion 8, as shown in FIG. 1 and FIG. 8 to FIG. 12.

[Traction Member 5]

Figure 8:
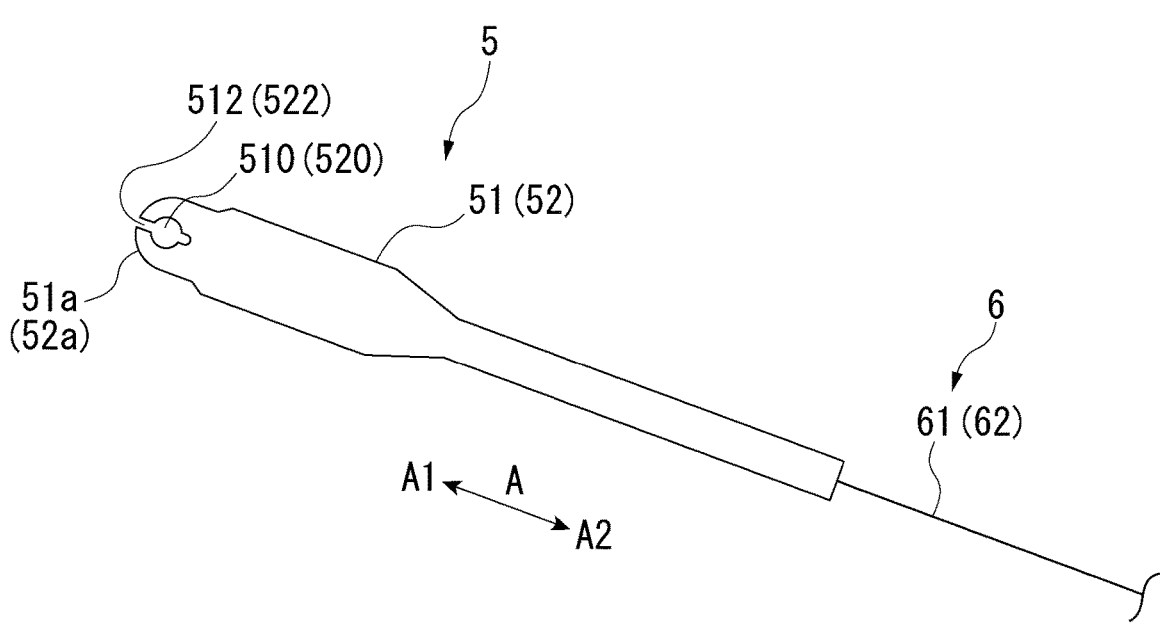
FIG. 8 is a view showing a traction member of an applicator of the clip device.

FIG. 8 is a view showing the traction member 5 of the applicator 200 of the clip device 100.

As shown in FIG. 8, the traction member 5 includes a first traction member 51 and a second traction member 52. Since the first traction member 51 and the second traction member 52 have substantially the same configuration, the figure of the second traction member 52 is omitted.

The first traction member 51 is arranged on the left side C1 relative to the connection portion 20B of the fixed arm 2. The first traction member 51 connects the distal-end portion 51a to the proximal-end side A2 of the first movable arm 31. Also, the proximal-end side A2 of the first traction member 51 is connected to the distal-end portion of the first operation wire 61. The first traction member 51 includes a first slide pin hole 510 and a first slide pin 511 at the distal-end portion thereof.

The first slide pin hole 510 is a hole provided in the distal-end portion 51a of the first traction member 51. The first slide pin 511 can be engaged with the first slide pin hole 510. The first slide pin hole 510 has a notch portion 512 on the distal-end side A1.

The first slide pin 511 connects the first slide pin hole 510, the first slide slot 310 of the first movable arm 31 and the engagement groove 23. The first slide pin 511 can advance and retract along the first slide slot 310 and the engagement groove 23 by sliding the first slider 812 of the operation portion 8 along the longitudinal direction A. When the first slide pin 511 advances along the first slide slot 310 and the engagement groove 23 toward the distal-end side A1, the first movable arm 31 rotates around the first rotation pin 211 as the center to open in the open-close direction B to enter the open state relative to the fixed arm 2. When the first slide pin 511 retreats along the first slide slot 310 and the engagement groove 23 toward the proximal-end side A2, the first movable arm 31 rotates around the first rotation pin 211 as the center to close in the open-close direction B to enter the closed state relative to the fixed arm 2. Accordingly, the first movable arm 31 is able to open and close relative to the fixed arm 2 in the open-close direction B. Here, the state in which the first movable arm 31 is closed relative to the fixed arm 2 includes the state in which a distance between the distal end of the first movable arm 31 and the distal end of the fixed arm 2 is substantially zero. In this state, the first movable arm 31 and the fixed arm 2 can clamp the living tissues as the treatment target between the first movable arm 31 and the fixed arm 2.

The second traction member 52 is arranged on the right side C2 relative to the connection portion 20B of the fixed arm 2. The second traction member 52 connects the distal-end portion 52a to the proximal-end side A2 of the second movable arm 32. Also, the proximal-end side A2 of the second traction member 52 is connected to the distal-end portion of the second operation wire 62. The second traction member 52 has a second slide pin hole 520 and a second slide pin 521 in the distal-end portion 52a.

The second slide pin hole 520 is provided in the distal-end portion 52a of the second traction member 52 and is a hole with which the second slide pin 521 can be engaged. The second slide pin hole 520 has a notch portion 522 on the distal-end side A1.

The second slide pin 521 connects the second slide pin hole 520, the second slide slot 320 of the second movable arm 32 and the engagement groove 23. The second slide pin 521 can advance and retract along the second slide slot 320 and the engagement groove 23 by sliding the second slider 822 of the operation portion 8 along the longitudinal direction A. When the second slide pin 521 advances along the second slide slot 320 and the engagement groove 23 toward the distal-end side A1, the second movable arm 32 rotates around the second rotation pin 221 as the center to open in the open-close direction B to enter the open state relative to the fixed arm 2. When the second slide pin 521 retreats along the second slide slot 320 and the engagement groove 23 toward the proximal-end side A2, the second movable arm 32 rotates around the second rotation pin 221 as the center to close in the open-close direction B to enter the closed state relative to the fixed arm 2. Accordingly, the second movable arm 32 is able to open and close relative to the fixed arm 2 in the open-close direction B. Here, the state in which the second movable arm 32 is closed relative to the fixed arm 2 includes the state in which a distance between the distal end of the second movable arm 32 and the distal end of the fixed arm 2 is substantially zero. In this state, the distal end of the second movable arm 32 and the distal end of the fixed arm 2 can clamp the living tissues as the treatment target.

In the state in which the first movable arm 31 is closed relative to the fixed arm 2, and the first engagement portion 311 is locked inside the clip holder 4, the first slider 812 of the operation portion 8 is slid toward the proximal-end side A2. As a result, the notch portion 512 is deformed or broken so as to be detached from the first slide pin 511. The first traction member 51 is separated from the connected fixed arm 2 and the first movable arm 31. Also, in the state in which the second movable arm 32 is closed with the fixed arm 2 and the second engaging portion 321 is locked inside the clip holder 4, the second slider 822 of the operation portion 8 is slid toward the proximal-end side A2. As a result, the notch portion 522 is deformed or broken so as to be detached from the second slide pin 521. The second traction member 52 is separated from the connected fixed arm 2 and the second movable arm 32. When the first traction member 51 and the second traction member 52 are separated from the fixed arm 2, the first movable arm 31 and the second movable arm 32, it is possible for the clip device 100 to indwell the treatment portion 1 including the fixed arm 2, the movable arm 3, and the clip holder 4 in the luminal cavity in the state of grasping the tissues.

[Operation Wire (Wire) 6]

As shown in FIG. 8, the operation wire (wire) 6 has a first operation wire 61 and a second operation wire 62. Since the first operation wire 61 and the second operation wire 62 have substantially the same configuration, the figure of the second operation wire 62 is omitted.

The first operation wire 61 connects the distal-end portion to the proximal-end portion of the first traction member 51. The proximal-end portion of the first operation wire 61 is fixed to the first slider 812 of the operation portion 8. The first operation wire 61 is inserted through the sheath 7 so as to be advanceable and retractable therein. The first operation wire 61 may be formed of, for example, a metal single wire or twisted wire. Also, the outer circumferential surface of the first operation wire 61 may be covered with a non-conductive member or the like. The first operation wire 61 is fixed to the first traction member 51 by various known methods such as adhesion, welding and the like. The first operation wire 61 can advance or retract the first traction member 51 by sliding the first slider 812 of the operation portion 8 attached to the proximal-end portion.

The second operation wire 62 connects the distal-end portion to the proximal-end portion of the second traction member 52. The proximal-end portion of the second operation wire 62 is fixed to the second slider 822 of the operation portion 8. The second operation wire 62 is inserted through the sheath 7 so as to be advanceable and retractable therein. The second operation wire 62 may be formed of, for example, a metal single wire or twisted wire. Further, the outer circumferential surface of the second operation wire 62 may be covered with a non-conductive member or the like. The second operation wire 62 is fixed to the second traction member 52 by various known methods, such as adhesion, welding and the like. The second operation wire 62 can advance or retract the second traction member 52 by sliding the second slider 822 of the operation portion 8 attached to the proximal-end portion.

[Sheath 7]

For example, as shown in FIG. 1, the sheath 7 is configured to extend along the longitudinal direction A and is an elongated member that can be inserted into the luminal cavity. The sheath 7 is made of an insulating material such as a fluororesin including PTFE (polytetrafluoroethylene) or a resin material such as HDPE (high density polyethylene). The sheath 7 has the flexibility and can easily change the shape following the curved shape of the luminal tissue or the like inside the luminal cavity so as to be inserted into and removed from the channel (not shown) of the clip device 100. A proximal-end portion 7b of the sheath 7 is connected to the operation portion 8, and a distal-end portion 7a is connected to the proximal-end side A2 of the clip holder 4. Also, the first operation wire 61 and the second operation wire 62 are inserted through the sheath 7.

[Operation Portion 8]

Figure 9:
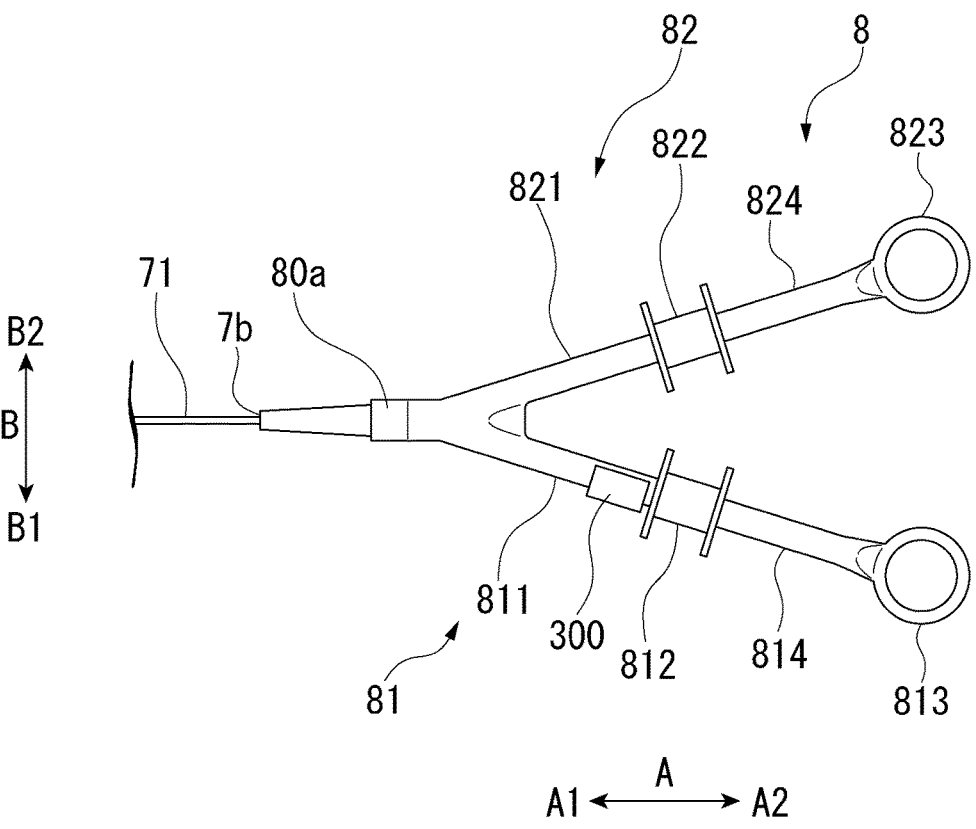
FIG. 9 is a view showing an operation portion of the applicator of the clip device.
Figure 10:
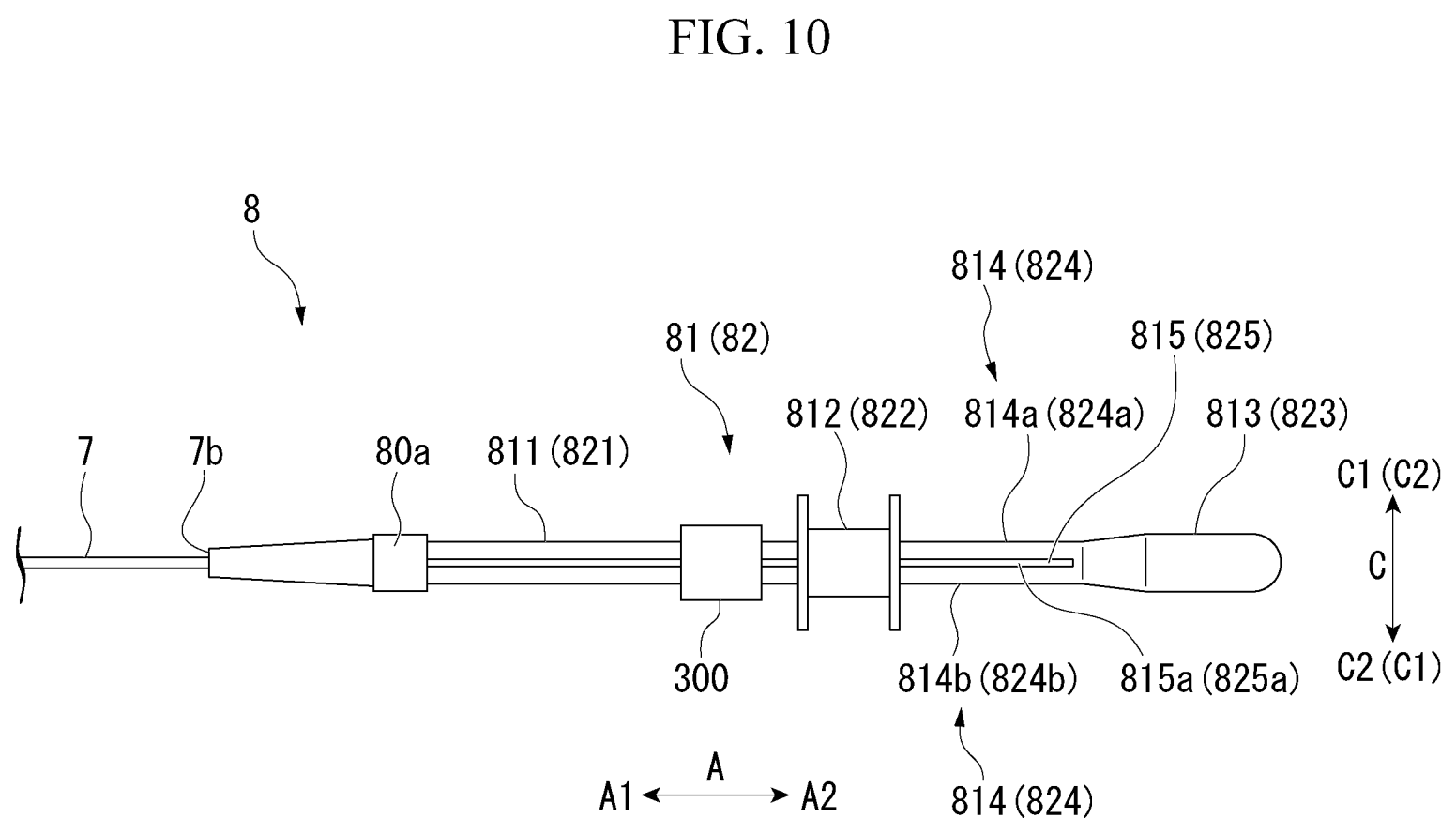

FIG. 9 is a view showing the operation portion 8 of the applicator 200 of the clip device 100. FIG. 10 is a view showing the operation portion 8 of the applicator 200 of the clip device 100 viewed from the upper side B1 (or the lower side B2) in the up-down direction B.

The operation portion 8 includes a distal-end portion 80a, a first operation portion 81, and a second operation portion 82, and extends in the longitudinal direction A, as shown in FIG. 1 or FIG. 9 to FIG. 10. The distal-end portion 80a is connected to the proximal-end portion 7b of the sheath 7, as shown in FIG. 9. In the present embodiment, the directions in which the first operation portion 81 and the second operation portion 82, which are connected from the distal end portion 80a to the distal end portion 80a of the operation portion 8, branch off from each other substantially coincide with the open-close direction B. The first operation portion 81 and the second operation portion 82 extend toward the upper side B1 and the lower side B2 in the up-down direction B from the distal-end portion 80a toward the proximal-end side A2.

The first operation portion 81 has a first operation portion main body (handle) 811, a first slider 812, and a finger hook portion 813, as shown in FIG. 9 and FIG. 10.

The first operation portion main body (handle) 811 operates the first traction member 51 and the first movable arm 31 via the first operation wire 61. The first operation portion main body 811 of the first operation portion 81 is formed in a substantially round rod shape extending in the longitudinal direction A. The first operation portion main body 811 includes a first outer surface 814 and a first slider groove 815, as shown in FIG. 10.

The first outer surface 814 is the surface of the first operation portion main body 811 exposed to the outside. The first outer surface 814 has a first left surface 814a provided on the left side C1 in the left-right direction C and a first right surface 814b provided on the right side C2. The first left surface 814a and the first right surface 814b are rounded in shape.

The first slider groove 815 is a groove formed in the upper side B1 of the first operation portion main body 811 along the longitudinal direction A, as shown in FIG. 10. The first slider groove 815 has a first sliding surface 815a on the surface of the first slider groove 815 on the upper side B1, and extends from the distal-end portion 80a of the operation portion 8 to the vicinity of the distal-end side A1 of the finger hook portion 813 of the first operation portion 81. The length of the first slider groove 815 in the longitudinal direction A is longer than the length when the first slider 812 and the stopper 300 attached to the first operation portion main body 811 described below are arranged in the longitudinal direction A.

As shown in FIG. 9 and FIG. 10, the first slider 812 has a substantially hollow columnar shape, and is fitted and attached to the first operation portion main body 811. The length of the first slider 812 in the longitudinal direction A is shorter than that of the first operation portion main body 811. Also, a part of the first slider 812 engages with the first slider groove 815 and slides on the first sliding surface 815*a*. Therefore, the first slider 812 is slidable in the longitudinal direction A relative to the first operation portion main body 811. The proximal-end portion of the first operation wire 61 is fixed to the first slider 812. When the first slider 812 is slid along the first operation portion main body 811 to advance and retreat in the longitudinal direction A, the first operation wire 61 and the first traction member 51 fixed to the distal-end portion of the first operation wire 61 are moved to advance and retreat along the longitudinal direction A. Furthermore, when the first traction member 51 advances and retreats along the longitudinal direction A, the first slide pin 511 of the first traction member 51 advances and retreats along the first slide slot 310. Then, the first movable arm 31 opens in the open-close direction B with the first rotation pin 211 as the center. With this configuration, when the first slider advances and retracts along the first operation portion main body 811 in the longitudinal direction A, the first movable arm opens and closes in the open-close direction B. It is noted that the inside of the first slider 812 does not have to be slidable on the first sliding surface 815*a* of the first slider groove 815. The first slider 812 is slidable relative to the first operation portion main body 811.

As shown in FIG. 9 and FIG. 10, the finger hook portion 813 is a substantially ring-shaped finger hooking portion formed on the proximal-end side A2 of the first operation portion main body 811.

The second operation portion 82 has a second operation portion main body (handle) 821, a second slider 822, and a finger hook portion 823, as shown in FIG. 9. As shown in FIG. 10, the second operation portion 82 is substantially the same configuration with the first operation portion in a case of reversing the left side C1 and the right side C2 in the left-right direction C when viewing the operation portion 8 of the clip device 200 from the lower side B2 in the up-down direction B.

The second operation portion main body (handle) 821 operates the second traction member 52 and the second movable arm 32 via the second operation wire 62. The second operation portion main body 821 of the second operation portion 82 is formed in a substantially round rod shape extending in the longitudinal direction A. As shown in FIG. 10, the second operation portion main body 821 includes a second outer surface 824 and a second slider groove 825.

The second outer surface 824 is the surface of the second operation portion main body 821 exposed to the outside. The second outer surface 824 has a second right surface 824*a* provided on the right side C2 in the left-right direction C and a second left surface 824*b* provided on the left side C1. The second right surface 824*a* and the second left surface 824*b* are rounded in shape.

As shown in FIG. 10, the second slider groove 825 is a groove formed along the longitudinal direction A on the lower side B2 of the second operation portion main body 821 in the up-down direction B. The second slider groove 825 has a second sliding surface 825*b* on the surface of the second slider groove 825 on the lower side B2, and extends from the distal-end portion 80*a* of the operation portion 8 to the vicinity of the distal-end side A1 of the finger hook portion 823 of the second operation portion 82.

As shown in FIG. 9 and FIG. 10, the second slider 822 has a substantially hollow columnar shape, and is fitted and attached to the second operation portion main body 821. The length of the second slider 822 in the longitudinal direction A is shorter than that of the second operation portion main body 821. A part of the second slider 822 engages with the second slider groove 825 and slides on the second sliding surface 825*a*. Therefore, the second slider 822 is slidable in the longitudinal direction A relative to the second operation portion main body 821. A proximal-end portion of the second operation wire 62 is fixed to the second slider 822. When the second slider 822 is slid along the second operation portion main body 821 to advance and retreat in the longitudinal direction A, the second operation wire 62 and the second traction member 52 fixed to the distal-end portion of the second operation wire 62 are moved to advance and retreat along the longitudinal direction A. Furthermore, when the second traction member 52 advances and retreats along the longitudinal direction A, the second slide pin 521 of the second traction member 52 advances and retreats along the second slide slot 320. Then, the second movable arm 32 opens in the open-close direction B around the second rotation pin 221 as the center. With this configuration, when the second slider 822 advances and retracts along the second operation portion main body 821 in the longitudinal direction A, the second movable arm 32 opens and closes in the open-close direction B. It is noted that the inside of the second slider 822 does not have to be slidable on the second sliding surface 825*a* of the second slider groove 825. The second slider 822 is slidable relative to the second operation portion main body 821.

As shown in FIG. 9 and FIG. 10, the finger hook portion 823 is a substantially ring-shaped finger hooking portion formed on the proximal-end side A2 of the second operation portion main body 821.

[Stopper 300]

Figure 11:
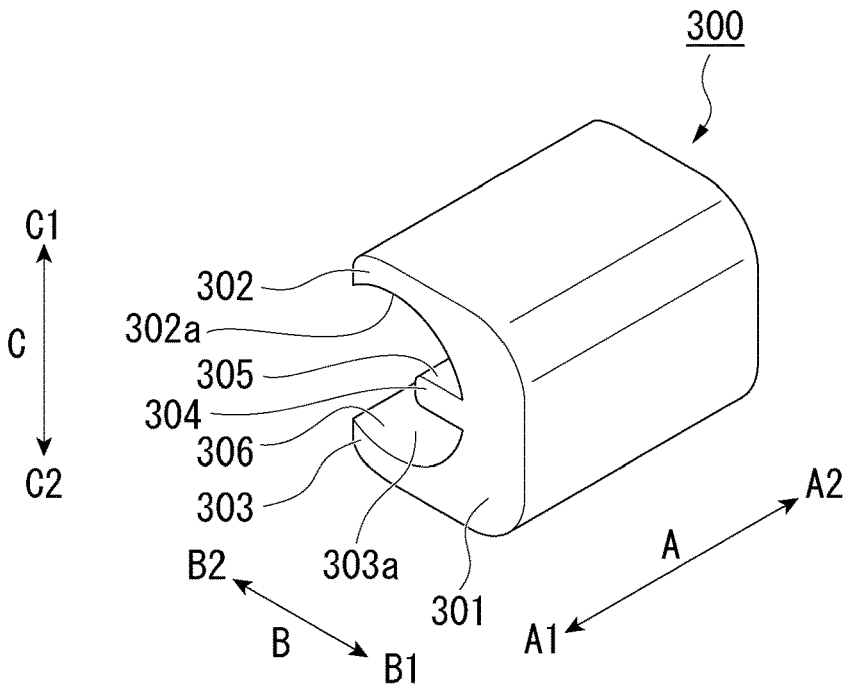
FIG. 11 is a view showing a stopper of the clip device.
Figure 12:
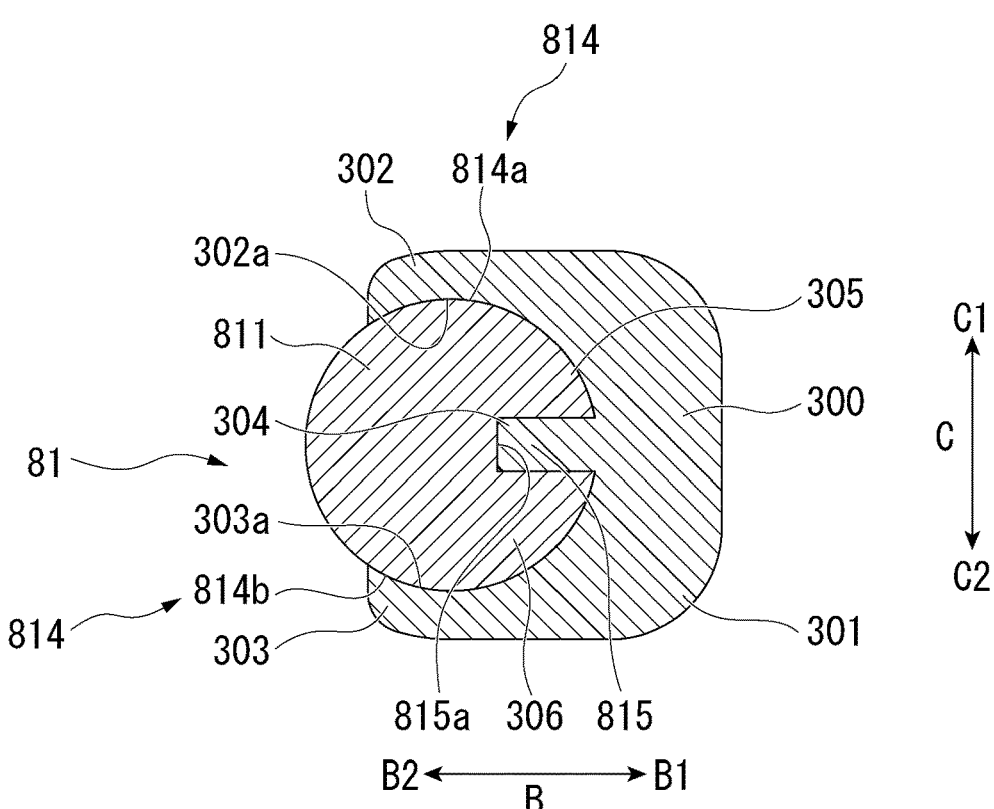
FIG. 12 is a cross-sectional view showing the operation portion and the stopper of the applicator of the clip device.

FIG. 11 is a view showing the stopper 300 of the clip device 100. FIG. 12 is a cross-sectional view showing the operation portion 8 and the stopper 300 of the applicator 200 of the clip device 100.

As shown in FIG. 9 and FIG. 10, the stopper 300 is attached to the first operation portion main body 811 of the clip device 100 to restrict the sliding of the first slider 812. The stopper 300 is arranged on the distal-end side A1 of the first slider 812 in the longitudinal direction A. The stopper 300 can be attached to or removed from any position on the first operation portion main body 811. Also, the stopper 300 can be locked at any position in the first slider groove 815 of the first operation portion main body 811. As shown in FIG. 11 and FIG. 12, the stopper 300 includes a base portion 301, a first outer wall portion 302, a second outer wall portion 303, an intermediate wall portion 304, a first slit portion 305, and a second slit portion 306.

As shown in FIG. 11 and FIG. 12, the base portion 301 is a substantially plate-shaped member provided on the upper side B1 in the up-down direction B. The length of the base portion 301 in the longitudinal direction A is shorter than the first slider groove 815 of the first operation portion main body 811. The length in the left-right direction C of the base portion 301 is longer than the outer diameter of the first operation portion main body 811 in the left-right direction C. The length of the base portion 301 in the up-down direction B is not particularly limited, however the length may be longer than that of the finger of the surgeon such that the surgeon can easily attach the stopper 300 to the first operation portion main body 811 using the base portion 301 as a handle.

The first outer wall portion 302 extends from the base portion 301 along the up-down direction B toward the lower side B2, as shown in FIG. 11 and FIG. 12. The first outer wall portion 302 is provided on the left side C1 of the stopper 300. The first outer wall portion 302 has a side surface 302a on the right side C2. The side surface 302a is formed following the shape of the first left surface 814a of the first operation portion main body 811, and as shown in FIG. 12, contacts the first left surface 814a.

The second outer wall portion 303 extends from the base portion 301 toward the lower side B2 along the up-down direction B, as shown in FIG. 11 and FIG. 12. The second outer wall portion 303 is provided on the right side C2 of the stopper 300. The second outer wall portion 303 has a side surface 303a on the left side C1. The side surface 303a is formed following the shape of the first right surface 814b of the first operation portion main body 811, and as shown in FIG. 12, contacts the first right surface 814b.

As shown in FIG. 11 and FIG. 12, the intermediate wall portion 304 extends from the base portion 301 toward the lower side B2 along the up-down direction B, and is provided between the first outer wall portion 302 and the second outer wall portion 303. The intermediate wall portion 304 has substantially the same shape as the first sliding surface 815a of the first slider groove 815 and can be inserted into the first slider groove 815.

The first slit portion 305 is a groove provided on the lower side B2 of the stopper 300 and formed between the first outer wall portion 302 and the intermediate wall portion 304, as shown in FIG. 11 and FIG. 12. The first slit portion 305 is arranged on the left side C1 of the stopper 300.

The second slit portion 306 is a groove provided on the lower side B2 of the stopper 300 and formed between the second outer wall portion 303 and the intermediate wall portion 304, as shown in FIG. 11 and FIG. 12. The second slit portion 306 is arranged on the right side C2 of the stopper 300.

The stopper 300 is attached to the first operation portion main body 811 of the first operation portion 81 from the upper side B1 in the up-down direction B, as shown in FIG. 12. Specifically, the stopper 300 inserts the intermediate wall portion 304 into the first slider groove 815 of the first operation portion main body 811. At that time, the portion of the first operation portion main body 811 excluding the first slider groove 815 enters the first slit portion 305 and the second slit portion 306. A side surface 302a of the first outer wall portion 302 contacts the first left surface 814a of the first operation portion main body 811. Also, the side surface 303a of the second outer wall portion 303 contacts the first right surface 814b of the first operation portion main body 811. With the above-described configuration, the stopper 300 is attached to the first operation portion main body 811 of the first operation portion 81.

Also, the stopper 300 can be attached to or removed from any position on the first operation portion main body 811. The surgeon brings the stopper 300 into contact with the distal-end side A1 of the first slider 812 to lock the stopper 300. Then, the stopper 300 can restrict the sliding of the first slider 812 toward the distal-end side A1. At this time, the sliding of the first slider 812 toward the proximal-end side A2 is not restricted. Therefore, the stopper 300 allows the first slider 812 to slide toward the proximal-end side A2.

The surgeon can attach the stopper 300 to the first operation portion main body 811 and then remove the stopper 300 from the first operation portion main body 811. Therefore, the stopper 300 can release the restriction on the sliding of the first slider 812 toward the distal-end side A1.

Here, the stopper 300 is not limited to this embodiment, and may be attached to the second operation portion main body 821 of the clip device 100, for example. Also, the stopper 300 may be attached to both the first operation portion main body 811 and the second operation portion main body 821. Also, the material of the stopper 300 is not particularly limited. For example, an elastic member such as elastically deformable rubber or resin may be used, or the stopper 300 may be made of metal. Also, the base portion 301 of the stopper 300 may be formed in a shape that is easy for the surgeon to hold and attach to the first operation portion main body 811.

[Operations and Effect of Clip Device 100]

Next, operations and effect of the clip device 100 will be described with reference to FIG. 13 to FIG. 20. In the present embodiment, as an example of how to use the clip device 100, a procedure for ligating a wound in body tissue will be described.

Figure 13:
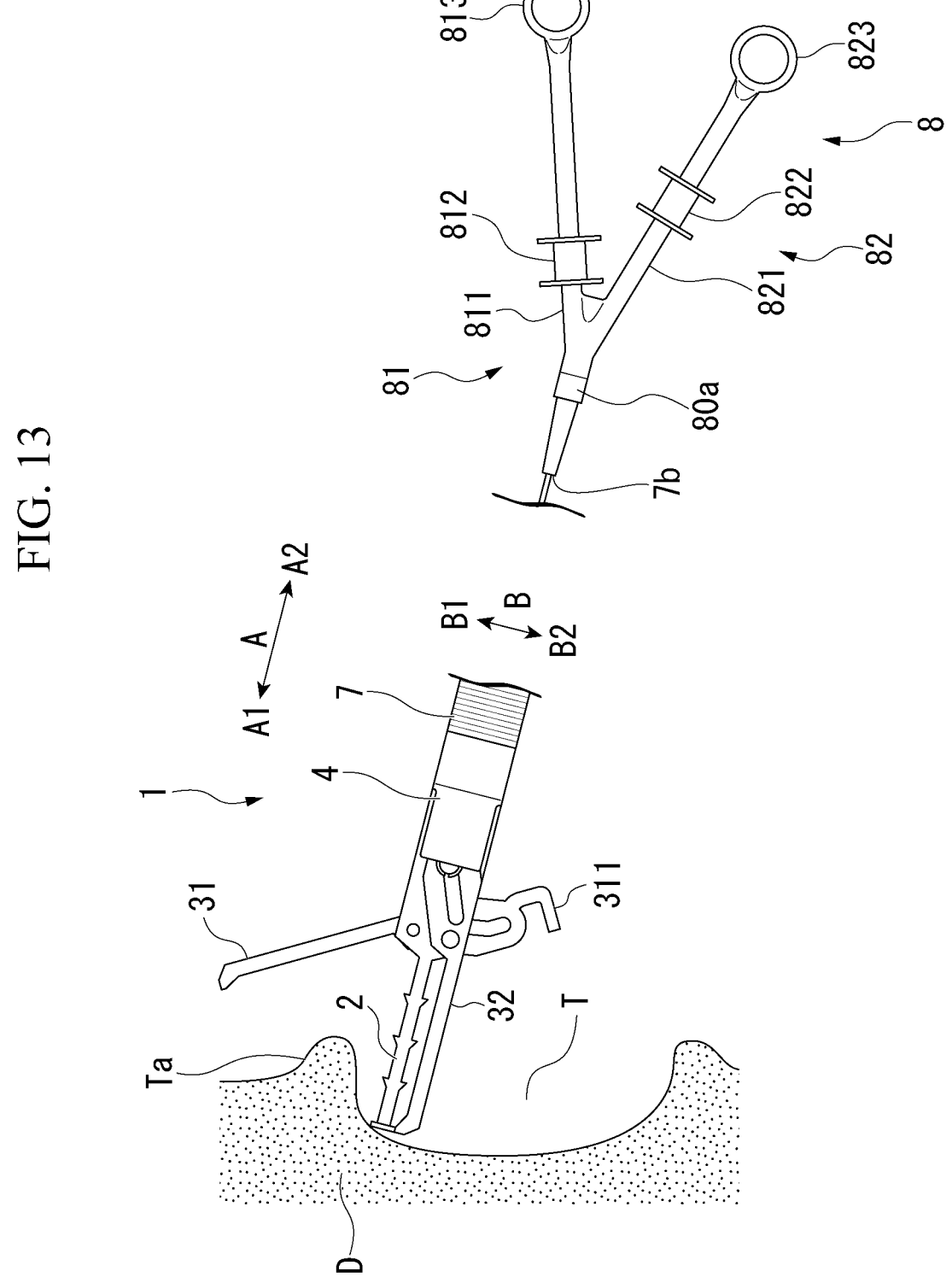
FIG. 13 is a schematic view showing a state of opening the first movable arm of the treatment portion of the clip device and moving the treatment portion to approach a first portion of the tissue to be grasped and a state of the operation portion at this time.
Figure 14:
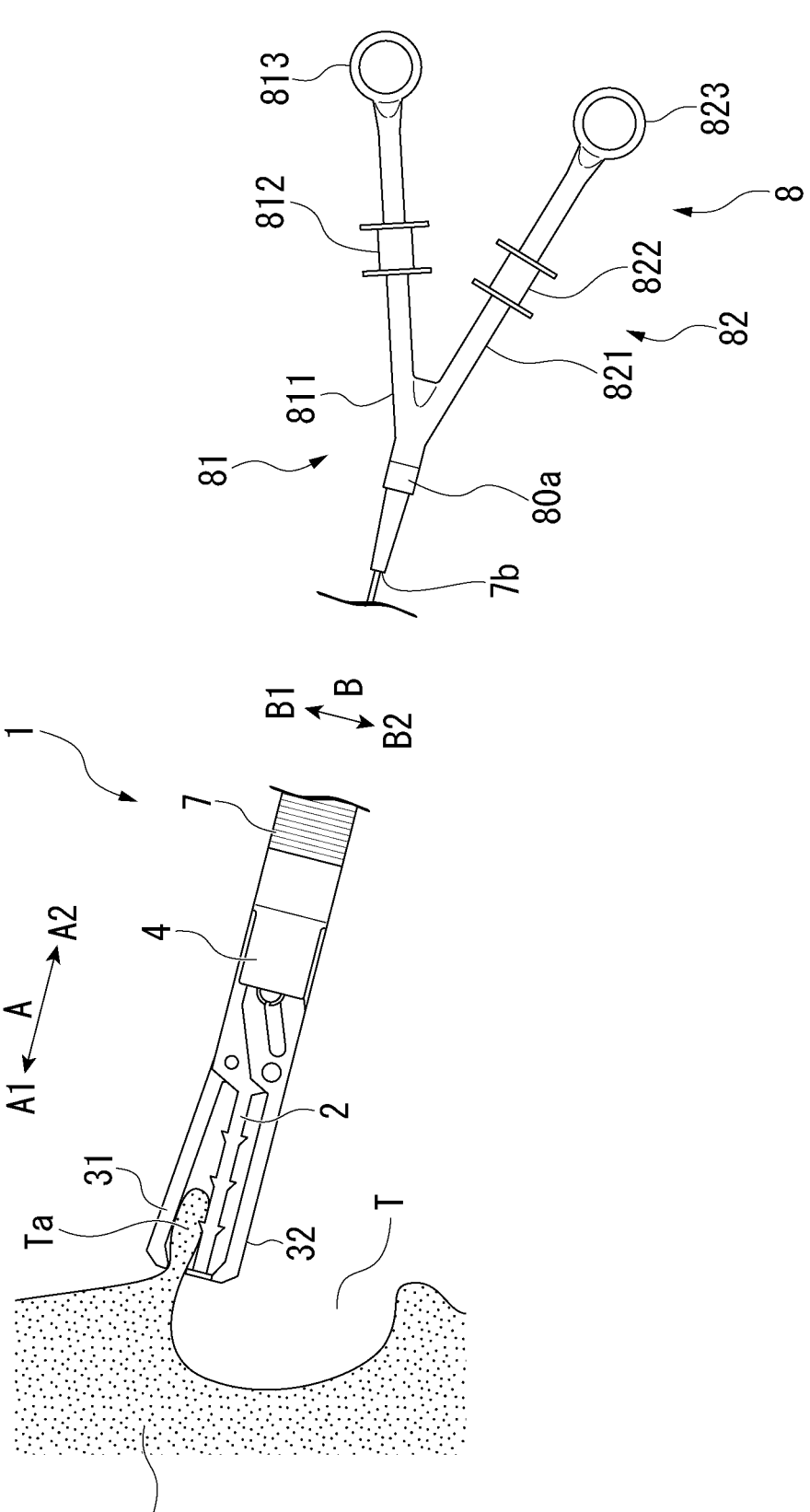
FIG. 14 is a schematic view showing a state of closing the first movable arm of the treatment portion of the clip device to grasp the first portion of the tissue and a state of the operation portion at this time.
Figure 15:
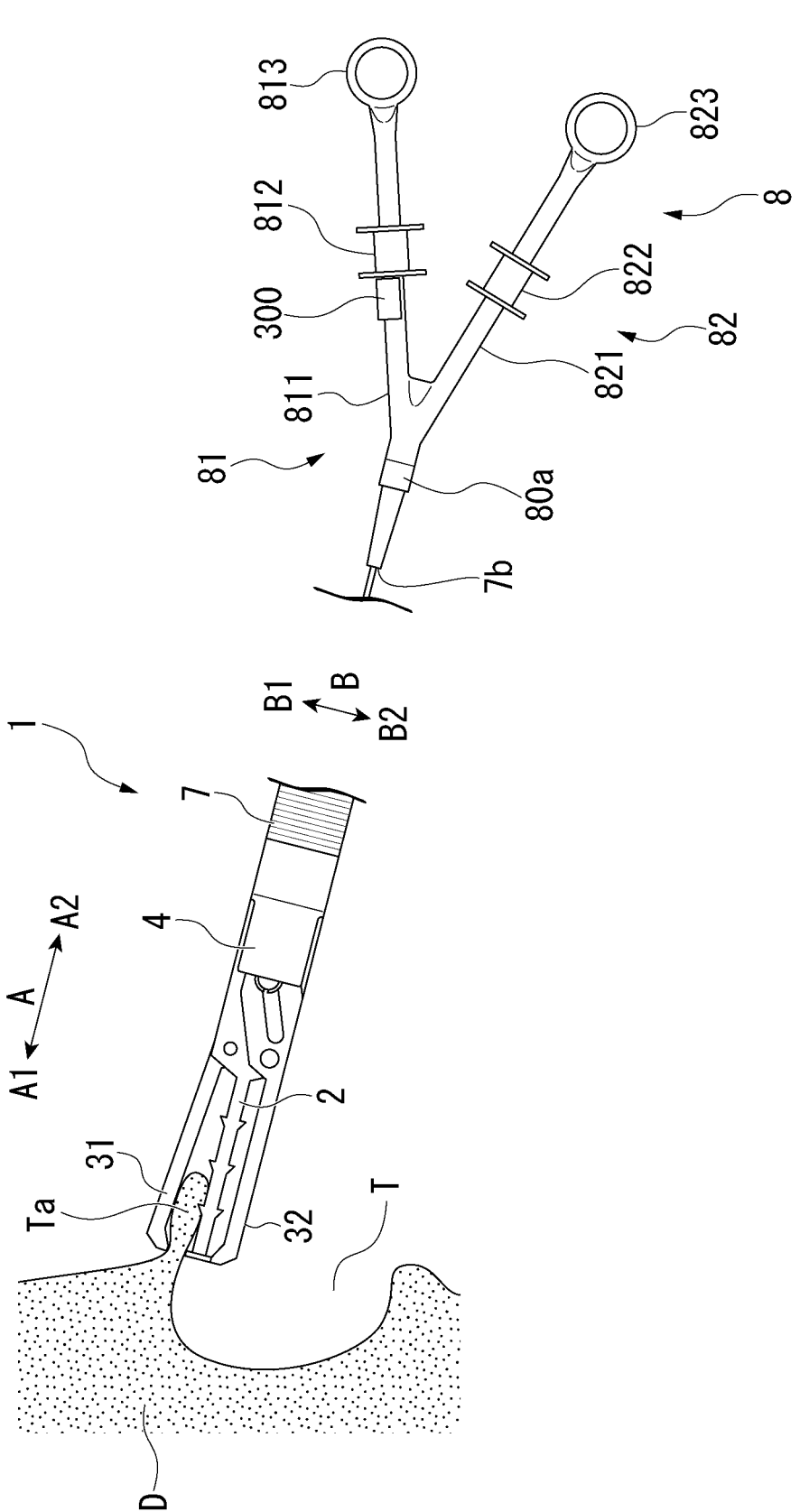
FIG. 15 is a schematic view showing a state of closing the first movable arm of the treatment portion of the clip device to grasp the first portion of the tissue and a state of attaching a stopper to a first operation portion at this time.
Figure 16:
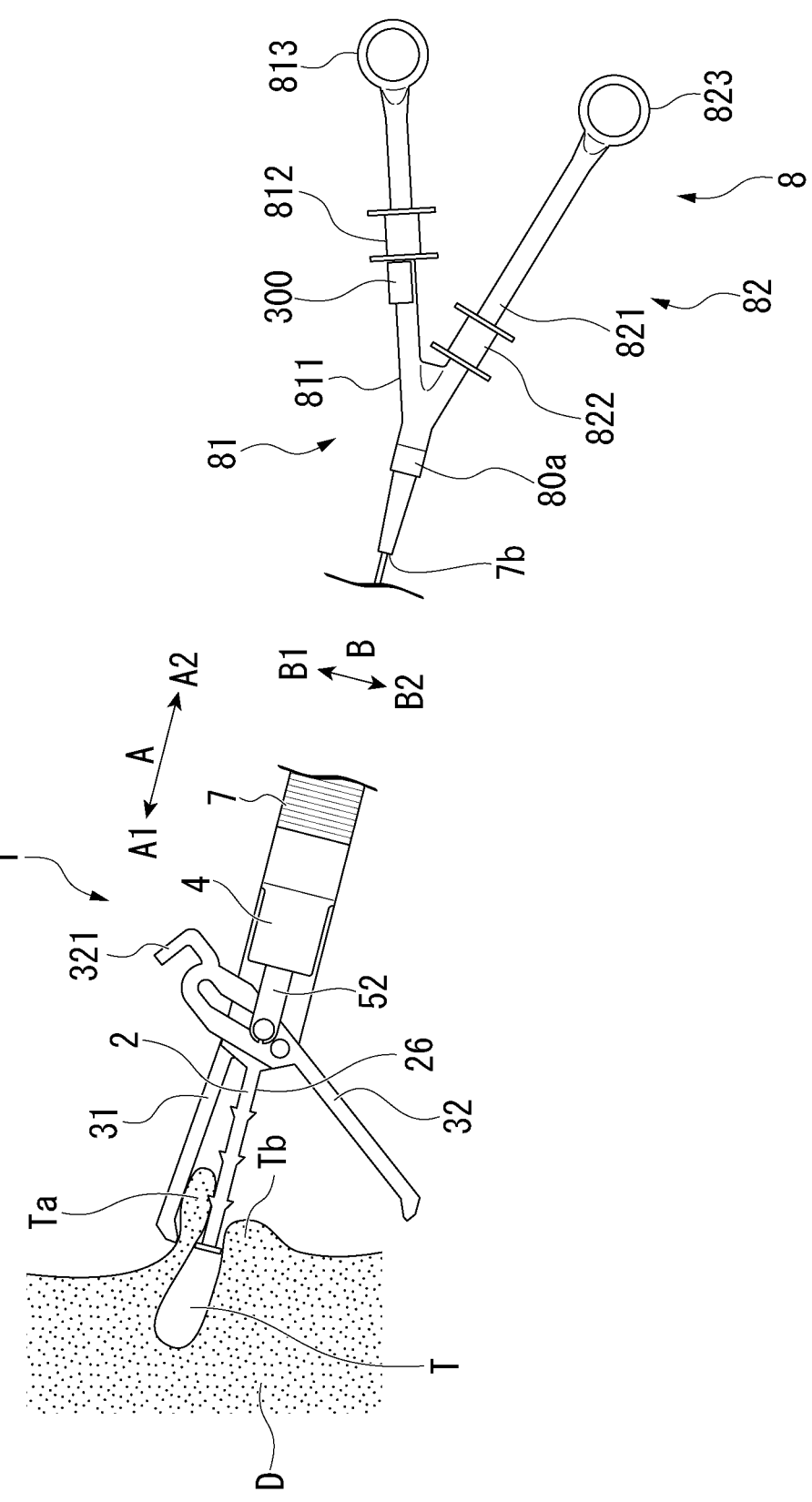

FIG. 13 is a view schematically showing a state in which the first movable arm 31 of the treatment portion 1 of the clip device 100 is opened and the treatment portion 1 is moved to approach the first portion Ta of the tissue to be grasped, and the state of the operation portion 8 at that time. FIG. 14 schematically shows a state in which the first movable arm 31 of the treatment portion 1 of the clip device 100 is closed and the first portion Ta of the tissue is grasped, and the state of the operation portion 8 at that time. FIG. 15 schematically shows a state in which the first movable arm 31 of the treatment portion 1 of the clip device 100 is closed and the first portion Ta of the tissue is grasped, and a state in which the stopper 300 is attached to the first operation portion 81 at that time. FIG. 16 is a view showing a state in which the first movable arm 31 of the treatment portion 1 of the clip device 100 grasps the first portion Ta of the tissue while opening the second movable arm 32 and moving the treatment portion 1 to the second portion Tb of the grasped tissue, and the states of the operation portion and the stopper 300 at that time. FIG. 17 is a view schematically showing a state in which the second movable arm 32 of the treatment portion 1 of the clip device 100 is closed to grasp the second portion Tb of the tissue, and the states of the operation portion 8 and the stopper 300 at that time. FIG. 18 is a view showing a state in which the second movable arm 32 of the clip device 100 grasps the second portion Tb of the tissue while detaching the stopper 300 that is attached to the first operation portion 81 to open the first movable arm 31 of the treatment portion 1 again and moves the treatment portion 1 to approach a third portion Tc different from the first portion Ta of the tissue and the state of the operation portion 8 at that time. FIG. 19 is a view showing a state in which the first movable arm 31 of the treatment portion 1 is closed to grasp the third portion Tc of the tissue and the state of attaching the stopper 300 to the first operation portion at that time. FIG. 20 is a view showing a state in which the treatment portion 1 is indwelled from the clip device 100 in a state in which the treatment portion 1 of the clip device 1 is grasping the tissue and the states of the operation portion 8 and the stopper 300 at that time.

[Preparation]

As a preparation operation, a surgeon (not shown) identifies a wound in body tissue by a known method.

Specifically, the surgeon inserts an insertion portion of an endoscope (not shown) into a digestive tract such as the esophagus, stomach, duodenum, or large intestine through a Natural orifice of a luminal cavity (for example, the mouth of a patient), and observes an image obtained by an imaging unit of the endoscope to specify a defect T in the tissue D inside the luminal cavity as the treatment target.

(Insertion Step)

The surgeon inserts the clip device 100 into the channel of the endoscope, and protrudes the clip device 100 from the distal-end opening of the channel of the endoscope. The surgeon moves the treatment portion 1 provided on the distal-end side A1 of the clip device 100 to the vicinity of the defect T.

(Arrangement Step)

As shown in FIG. 13, the surgeon opens and closes the first movable arm 31 near the first portion Ta as an edge of the defect T as the ligation target while viewing the image. More specifically, the surgeon slides the first slider 812 in the longitudinal direction A toward the distal-end side A1. Then, the first traction member 51 moves toward the distal-end side A1. When the first slide pin 511 connected to first traction member 51 advances, the first movable arm 31 rotates about the first rotation pin 211 as the center of rotation. The first movable arm 31 rotates toward the upper side B1 in the open-close direction B such that the first arm portion 312 on the distal-end side A1 is separated from the fixed arm 2. As a result, the first movable arm 31 enters the open state relative to the fixed arm 2, and it is possible to grasp the first portion Ta.

In this state, the surgeon moves the first movable arm 31 in the open state and the fixed arm 2 toward the first portion Ta that is intended to be grasped, and locate the first portion Ta between the first movable arm 31 and the fixed arm 2.

(Grasping Step)

In FIG. 14, when the surgeon confirms that the first portion Ta is positioned between the first movable arm 31 and the fixed arm 2, the surgeon slides the first slider 812 of the first operation portion 81 to the proximal-end side A2 to move the first traction member 51 toward the proximal-end side A2. As a result, when the first slide pin 511 connected to the first traction member 51 retreats, the first arm portion 312 of the first movable arm 31 rotates toward the lower side B2 in the open-close direction B toward the fixed arm 2. As a result, the first movable arm 31 enters the closed state relative to the fixed arm 2 and grasps the first portion Ta.

During the process when the surgeon pulls the first slider 812 toward the proximal-end side A2, the first engagement portion 311 formed on the proximal-end side A2 of the first movable arm 31 also rotates about the first rotation pin 211 in the close direction B. As a result, the first engagement portion 311 enters the groove portion 41 formed in the clip holder 4 and is accommodated inside the clip holder 4. Accordingly, the first portion Ta is grasped by the first movable arm 31 and the fixed arm 2.

(Regulating Sliding of Slider Step)

In FIG. 15, the surgeon attaches the stopper 300 to the first operation portion main body 811 while grasping the first portion Ta with the first movable arm 31 and the fixed arm 2. The stopper 300 is attached to the distal-end side A1 of the first slider 812 provided on the first operation portion main body 811. The surgeon slides the stopper 300 toward the proximal-end side A2 to abut against the distal-end side A1 of the first slider 812. The stopper 300 abuts on the distal-end side A1 of the first slider 812 and is engaged with the first operation portion main body 811. Then, the stopper 300 can restrict the sliding of the first slider 812 toward the distal-end side A1. Further, the stopper 300 can fix the relative positions between the first movable arm 31 and the fixed arm 2 and maintain the state of grasping the first portion Ta of the defect T. Here, the sliding of the first slider 812 toward the proximal-end side A2 is not restricted.

Accordingly, the stopper 300 can allow the first slider 812 to slide toward the proximal-end side A2.

(Traction Step)

In FIG. 16, the surgeon maintains the state of grasping the first portion Ta of the defect T by the stopper 300 and moves the whole treatment portion 1 to the first portion Ta and the vicinity of the second portion Tb that is positioned to be opposite to the first portion Ta while drawing the first portion Ta to the vicinity of the second portion Tb. During this process, the stopper 300 maintains the closed state of the first movable arm 31 and the fixed arm 2.

(Arrangement Step)

When the surgeon confirms that the treatment portion 1 reaches the vicinity of the second portion Tb as an edge portion of the defect T, the surgeon opens and closes the second movable arm 32 near the second portion Tb. More specifically, the surgeon slides the second slider 822 toward the distal-end side A1. Then, the second traction member 52 moves to the distal-end side A1. When the second slide pin 521 connected to the second traction member 52 advances, the second movable arm 32 rotates about the second rotation pin 221 as the center of rotation. The second movable arm 32 rotates toward the lower side B2 in the open-close direction B such that the second arm portion 322 on the distal-end side A1 is separated from the fixed arm 2. As a result, the second movable arm 32 is in the open state relative to the fixed arm 2, and it is possible to grasp the second portion Tb of the defect T as the treatment target.

In this state, the surgeon moves the second movable arm 32 and the fixed arm 2, which are in the open state, toward the second portion Tb of the defect T that is intended to be grasped, and locates the second portion Tb of the defect T between the second movable arm 32 and the fixed arm 2.

(Grasping Step)

As shown in FIG. 17, when the surgeon can confirm that the second portion Tb of the defect T is positioned between the second movable arm 32 and the fixed arm 2, the surgeon slides the second slider 822 of the second operation portion 82 to the proximal-end side A2 to move the second traction member 52 to the proximal-end side A2. As a result, when the second slide pin 521 connected to the second traction member 52 retreats, the second arm portion 322 of the second movable arm 32 rotates toward the upper side B1 in the open-close direction B toward the fixed arm 2. As a result, the second movable arm 32 enters the closed state relative to the fixed arm 2 so as to grasp the second portion Tb of the defect T as the treatment target.

In the process in which the surgeon slides the second slider 822 toward the proximal-end side A2, the second engaging portion 321 formed on the proximal-end side A2 of the second movable arm 32 also rotates about the second rotation pin 221 as the center in the open-close direction B. As a result, the second engaging portion 321 enters the groove portion 41 formed in the clip holder 4 and is accommodated inside the clip holder 4. Accordingly, the second portion Tb of the defect T is grasped by the second movable arm 32 and the fixed arm 2.

(Releasing Restriction to Sliding of Slider Step)

In FIG. 18, the surgeon can remove the stopper 300 attached to the first operation portion main body 811 from the first operation portion main body 811. When the stopper 300 is removed, the stopper 300 can release the restriction on the sliding of the first slider 812 toward the distal-end side A1. Accordingly, the surgeon can slide the first slider 812 toward the distal-end side A1 again. When the first slider 812 is slid toward the distal-end side A1, the first movable arm 31 rotates toward the upper side B1 in the open-close direction B so as to separate from the fixed arm 2. Then, the surgeon can make the first movable arm 31 to transition to the open state in which the first movable arm 31 is opened relative to the fixed arm 2 to release the state of grasping the first portion Ta. The surgeon subsequently brings the first movable arm 31 to approach the third portion Tc which is different from the first portion Ta. The surgeon slides the first slider 812 in the longitudinal direction A toward the distal-end side A1. Then, the first movable arm 31 enters the open state relative to the fixed arm 2 such that it is possible to grasp the third portion Tc as the edge portion of the defect T. The surgeon closes the first movable arm 31 relative to the fixed arm 2 by sliding the first slider 812 of the first operation portion 81 toward the proximal-end side A2 so as to close the third portion Tc. It is noted that this step does not necessarily have to be performed after the second portion Tb is grasped by the second movable arm 32 and the fixed arm 2. That is, as shown in FIG. 15 and FIG. 16, in the state in which the first portion Ta is grasped by the first movable arm 31 and the fixed arm 2, the surgeon can remove the stopper 300 attached to the first operation portion main body 811 from the first operation portion main body 811. In this case, as described above, the surgeon can make the first movable arm 31 to transition to the open state relative to the fixed arm 2 to release the state of grasping the first portion Ta. Subsequently, the surgeon can close the first movable arm 31 relative to the fixed arm 2 to grasp the third portion Tc by sliding the first slider 812 of the first operation portion 81 to the proximal-end side A2.

(Restricting Sliding of Slider Step)

In FIG. 19, in the state in which the third portion Tc is grasped by the first movable arm 31 and the fixed arm 2, the surgeon attaches the stopper 300 to the first operation portion main body 811 again. The stopper 300 is attached to the distal-end side A1 of the first slider 812 provided on the first operation portion main body 811. The surgeon slides the stopper 300 toward the proximal-end side A2 to abut against the distal-end side A1 of the first slider 812. The stopper 300 abuts on the distal-end side A1 of the first slider 812 and is locked to the first operation portion main body 811. Then, the stopper 300 can restrict the sliding of the first slider 812 toward the distal-end side A1. Furthermore, the stopper 300 can maintain the state in which the third portion Tc is grasped by the first movable arm 31 and the fixed arm 2. Here, the sliding of the first slider 812 toward the proximal-end side A2 is not restricted. Therefore, the stopper 300 allows the first slider 812 to slide toward the proximal-end side A2.

Thereafter, when the first slider 812 of the operation portion 8 is further slid toward the proximal-end side A2 in the longitudinal direction A, the clip holder 4 makes the first engaging portion 311 of the first movable arm 31 to be engaged with the inside of the clip holder 4 so as to lock the first movable arm 31 to not to open. Also, when the second slider 822 of the operation portion 8 is further slid toward the proximal-end side A2 in the longitudinal direction A, the clip holder 4 makes the second engaging portion 321 of the second movable arm 32 to be engaged with the inside of the clip holder 4 so as to lock the second movable arm 32 to not to open.

(Releasing Connection and Indwelling Step)

By the above-described treatment, the second portion Tb and the third portion Tc of the defect T as the treatment targets are grasped by the treatment portion 1 as shown in FIG. 19. In this state, the surgeon further slides the first slider 812 of the first operation portion 81 and the second slider 822 of the second operation portion 82 toward the proximal-end side A2 to move the first traction member 51 and the second traction member 51 to the proximal-end side A2. The first traction member 51 and the second traction member 52 are detachably attached to the first slide pin 511 and the second slide pin 521, respectively. For example, by pulling the first traction member 51 toward the proximal-end side A2, the notch portion 512 of the first traction member 51 is deformed or broken, and the first slide pin 511 comes out of the first slide pin hole 510 so as to release the engagement. Also, by pulling the second traction member 52 toward the proximal-end side A2, the notch portion 522 of the second traction member 52 is deformed or broken, and the second slide pin 521 comes out of the second slide pin hole 520 and so as to release the engagement. It is noted that that the specific configuration of the engagement between the first traction member 51 and the first slide pin 511, and the engagement between the second traction member 52 and the second slide pin 521 are not limited to the present embodiment.

As shown in FIG. 20, when the amount of the force that the surgeon moves the first traction member 51 and the second traction member 52 toward the proximal-end side A2 exceeds a predetermined value, as described above, the engagement between the first traction member 51 and the first slide pin 511 and the engagement between the second traction member 52 and the second slide pin 521 are released. At this time, the connection between the applicator 200 including the traction member 5, the operation wire 6, the sheath 7, and the operation portion 8, and the stopper 300 to which the operation portion 8 is attached and the treatment portion 1 including the fixed arm 2, the movable arm 3, and the clip holder 4 is released. Accordingly, the treatment portion 1 is indwelled inside the luminal cavity (inside the body) in the state in which the first movable arm 31 and the fixed arm 2 grasp the third portion Tc of the defect T and the second movable arm 32 and the fixed arm grasp the second portion Tb of the defect T.

The step of releasing the restriction to the sliding of slider as shown in FIG. 18 and the step of restricting the sliding of slider as shown in FIG. 19 are not necessarily have to be executed. That is, in the grasping step as shown in FIG. 17, in the state in which the first portion Ta and the second portion Tb of the defect T are grasped by the movable arm 3 and the fixed arm 2, as shown in FIG. 20, the treatment portion 1 can be indwelled inside the luminal cavity.

The surgeon then operates the operation portion 8 of the clip device 100 to remove the sheath 7 to the outside of the patient's body. Due to the above-described steps, the surgeon completes the treatment for the treatment target.

In the present embodiment, with the above-described configuration, it is possible for the treatment portion 1 of the clip device 100 to close the defect T of the tissue D as the treatment target.

Further, in the present embodiment, the stopper 300 may make the first engagement portion 311 of the first movable arm 31 to be engaged to the inside of the clip holder 4 so as to restrict the sliding of the first slider 812 toward the distal-end side A1 without performing the locking operation. Furthermore, the stopper 300 can fix the relative position between the first movable arm 31 and the fixed arm 2 so as to maintain the state of grasping the first portion Ta of the defect T. Therefore, the surgeon can operate the second slider 822 of the second operation portion 82 without suppressing the sliding of the first slider 812 of the first operation portion 81 toward the distal-end side A1. Therefore, the operation of the clip device 100 becomes easy, and the time required for surgery can be shortened.

Also, in the present embodiment, the stopper 300 does not restrict the sliding of the first slider 812 toward the proximal-end side A2. The stopper 300 can allow the first slider 812 to slide toward the proximal-end side A2. Therefore, even in a case in which the force for grasping the tissue by the first movable arm 31 and the fixed arm 2 is not enough, the surgeon can slide the first slider 812 toward the proximal-end side A2 to grasp the tissue with a stronger force. Therefore, it is possible to prevent the tissue from slipping off from the arms.

Also, in the present embodiment, the surgeon can remove the stopper 300 attached to the first operation portion main body 811 from the first operation portion main body 811. Therefore, the surgeon can change the position of the stopper 300 by several times. In addition, the surgeon can release the restriction on sliding of the first slider 812 toward the distal-end side A1.

Also, in the present embodiment, the surgeon can release the restriction on sliding of the first slider 812 toward the distal-end side A1 by the stopper 300, and slide the first slider 812 toward the distal-end side A1 again. The surgeon makes the first movable arm 31 to transition to the state of being opened relative to the fixed arm 2 to release the state in which the first portion Ta of the defect T is grasped. Therefore, the surgeon can easily change the position of the defect T grasped by the treatment portion 1. Also, it is possible to reduce the possibility that the movable arm 3 cannot be unlocked after being locked and the surgeon cannot change the position at which the tissue is grasped.

As described above, the first embodiment of the present disclosure has been described in detail with reference to the drawings; however, the specific configuration is not limited to the present embodiment, and design changes and the like are included within the scope of the present disclosure. Also, the stopper and the usage method thereof according to the present embodiment can be combined with the configuration according to each embodiment described below. The configurational elements shown in the present embodiment and each embodiment described below can be combined as appropriate.

Second Embodiment

Next, a second embodiment of the present disclosure will be described with reference to FIG. 21 to FIG. 24. In the following description, the same reference signs are given to the same configurations as those already described, and redundant descriptions will be omitted. Each of the following embodiments differs from the first embodiment in the operation portion of the applicator and the stopper. Therefore, in the following description, the differences from the first embodiment will be mainly described. FIG. 21 is a view showing the operation portion 8A of the applicator 200A of the clip device 100A according to the second embodiment of the present disclosure that is viewed from the upper side B1 in the up-down direction B. FIG. 22 is a perspective view showing the stopper 300A of the clip device 100A. FIG. 23 is a cross-sectional view showing the stopper 300A of the clip device 100A. FIG. 24 is a perspective view showing the operation portion 8A and the stopper 300A of the clip device 100A.

The clip device 100A according to the second embodiment of the present disclosure includes the treatment portion (clip) 1, the applicator 200A, and the stopper 300A. The applicator 200A also includes the traction member 5, the operation wire 6, the sheath 7, and an operation portion 8A. Here, since the treatment portion 1, the traction member 5, the operation wire 6, and the sheath 7 are the same as those according to the first embodiment, their description and figures are omitted.

The operation portion 8A includes the distal-end portion 80a, a first operation portion 81A, and the second operation portion 82. Since the distal-end portion 80a and the second operation portion 82 are the same as those in the first embodiment, their description and figures are omitted. The first operation portion 81A has a first operation portion main body (handle) 811A, the first slider 812, and the finger hook portion 813, as shown in FIG. 21. Similarly, the first slider 812 and the finger hook portion 813 are the same as in the first embodiment such that description and figures of the first slider 812 and the finger hook portion 813 are omitted.

The first operation portion main body (handle) 811A includes a first outer surface 814A and a first slider groove 815, as shown in FIG. 21. Since the first slider groove 815 is the same as that of the first embodiment, description and figure thereof are omitted.

As shown in FIG. 21, the first outer surface 814A has a male screw portion 814s in addition to the configuration of the first outer surface 814 according to the first embodiment. The male screw portion 814s is provided along the longitudinal direction A on the first outer surface 814A.

As shown in FIG. 22 and FIG. 23, the stopper 300A is provided on the first operation portion main body 811A. The stopper 300A has a substantially hollow cylindrical shape. The stopper 300A is attached to the distal-end side A1 of the first slider 812 provided in the first operation portion main body 811A. The stopper 300A has an insertion hole 307 and an inner circumferential surface 308.

The insertion hole 307 is formed inside the stopper 300A. The stopper 300A is attached to the first operation portion main body 811A by inserting the first operation portion main body 811A through the insertion hole 307.

As shown in FIG. 22 and FIG. 23, the inner circumferential surface 308 is formed inside the stopper 300A. The inner circumferential surface 308 is a surface being opposite to the first operation portion main body 811A inserted through the insertion hole 307. The inner circumferential surface 308 has a female screw portion 308s. The female screw portion 308s is formed by the stopper 300A moving along the longitudinal direction A in the central axis R of the stopper 300A along the longitudinal direction A when the stopper 300A rotates around the central axis R. The female screw portion 308s fits into the male screw portion 814s provided on the first outer surface 814A of the first operation portion main body 811A.

For example, when the stopper 300A is rotated in a first direction R1 of the central axis R, the female screw portion 308s is screwed into the male screw portion 814s such that the stopper 300A is movable to the proximal-end side A2 in the longitudinal direction A. Also, when the stopper 300A is rotated in a second direction R2 of the central axis R, the female screw portion 308s is screwed into the male screw portion 814s such that the stopper 300A is movable to the distal-end side A1 in the longitudinal direction A.

Next, by referring to FIG. 24, the operations and effects of the stopper 300A of the clip device 100A according to the second embodiment will be described. In the present embodiment, the treatment for ligating a wound in body tissue is the same as that in the first embodiment, and thus description thereof is omitted.

As shown in FIG. 24, the stopper 300A is provided on the distal-end side A1 of the first operation portion main body 811A relative to the first slider 812. Also, the female screw portion 308s of the stopper 300A is fitted with the male screw portion 814s of the first operation portion main body 811A inserted through the insertion hole 307. Therefore, when the surgeon rotates the stopper 300A about the central axis R in the first direction R1, the stopper 300A moves to the proximal-end side A2 in the longitudinal direction A. The surgeon moves the stopper 300A to the proximal-end side A2 to abut on the distal-end side A1 of the first slider 812. The stopper 300A abuts on the distal-end side A1 of the first slider 812 and is engaged with the first operation portion main body 811A. Then, the stopper 300A can restrict the sliding of the first slider 812 toward the distal-end side A1. Furthermore, the stopper 300A can maintain the relative position of the first movable arm 31 and the fixed arm 2 at a fixed position. Here, the sliding of the first slider 812 toward the proximal-end side A2 is not restricted. Therefore, the stopper 300A can allow the first slider 812 to slide toward the proximal-end side A2.

Also, when the surgeon rotates the stopper 300A about the central axis R in the second direction R2, the stopper 300A moves to the distal-end side A1 in the longitudinal direction A. Then, the stopper 300A can release the restriction on the sliding of the first slider 812 toward the distal-end side A1. The surgeon can slide the first slider 812 toward the distal-end side A1 again. When the first slider 812 is slid toward the distal-end side A1, the first movable arm 31 rotates toward the upper side B1 in the open-close direction B so as to separate from the fixed arm 2. Then, the surgeon can make the first movable arm to transition to the open state relative to the fixed arm 2. In addition, the first direction R1 and the second direction R2 as the rotation directions are not particularly limited. The first direction R1 and the second direction R2 may be formed with opposite rotation directions.

In the present embodiment, the stopper 300A is provided in the first operation portion main body 811A. Therefore, the surgeon can restrict the sliding of the first slider 812 toward the distal-end side A1 and release the restriction without spending time on attaching the stopper 300A to the first operation portion main body 811A and removing the stopper 300A therefrom during the surgery. Also, the surgeon can reduce the possibility of dropping or losing the stopper 300A.

Also, in the present embodiment, it is unnecessary for the surgeon to attach the stopper 300A to the first operation portion main body 811A of remove the stopper 300A therefrom during the surgery. Therefore, the surgeon can easily restrict the sliding of the first slider 812 toward the distal-end side A1 and release the restriction.

As described above, the second embodiment of the present disclosure has been described in detail with reference to the drawings; however, the specific configuration is not limited to the present embodiment, and design changes and the like are also included within the scope of the present disclosure. Also, the configurational elements shown in the above-described embodiment and modification examples shown below can be combined as appropriate.

Modification Example

A plurality of stoppers 300 may be provided in the clip device 100 according to the first embodiment described above. For example, as shown in FIG. 25, the stopper 300 may be provided in the first operation portion main body 811 of the first operation portion 81 and the second operation portion main body 821 of the second operation portion 82. Also, the stopper 300 may be provided only in the second operation portion main body 821. Similarly, the clip device

100A according to the second embodiment described above may also include a plurality of stoppers 300A. Also, the stopper 300A may be provided in the second operation portion 82 or may be provided on both the first operation portion 81A and the second operation portion 82.

Also, the stopper 300 according to the first embodiment may not be slidable relative to the first slider groove 815 of the first operation portion main body 811. For example, the clip device 100 includes a plurality of first slider grooves 815 along the longitudinal direction A of the first operation portion main body 811 that are aligned with the length of the stopper 300 along the longitudinal direction A. The position where the stopper 300 is attached to the first operation portion main body 811 can be changed depending on the position of the first slider groove 815. Therefore, the surgeon can attach the stopper 300 to the first slider groove 815 near the distal-end side A1 of the first slider 812 provided in the first operation portion main body 811 without sliding the stopper 300, and restrict the sliding of the slider 812 toward the distal-end side A1.

Also, the stopper 300 according to the first embodiment restricts the sliding of the first slider 812 toward the distal-end side A1 by being attached to or removed from the first operation portion main body 811; however, by providing a rotation portion with unevenness, the position of attaching the stopper 300 to the first operation portion main body 811 may be moved by sliding the stopper 300 on the first operation portion main body 811. In this case, the stopper 300 may be configured as a conventional ratchet mechanism including multiple unevenness on the first sliding surface 815a that engage with the rotation portion of the stopper 300 to allow the sliding of the first operation portion main body 811 toward the distal-end side A1 and restrict the sliding thereof toward the proximal-end side A2.

Also, the length of the stopper in the longitudinal direction A according to the present disclosure is not particularly limited. Therefore, by increasing the length of the stopper in the longitudinal direction A, the sliding range of the slider of the operation portion can be adjusted.

Also, the first operation portion 81 and the second operation portion 82 according to the above-described embodiments do not have to be formed in the substantially round rod shapes. The first operation portion 81 and the second operation portion 82 may be formed in, for example, polygonal bar shapes. The shapes of the first operation portion 81 and the second operation portion 82 are not particularly limited.

Also, the stopper 300 according to the first embodiment may be used even when the first operation portion 81 and the second operation portion 82 of the operation portion 8 are not branched. For example, as shown in FIG. 26, the operation portion 8B includes a first operation portion 81B and a second operation portion 82B that are not branched to extend from the distal-end portion 80a toward the proximal-end side A2. Also, the first operation portion 81B and the second operation portion 82B each has the operation portion main body, the slider, and the finger hook portion, as same as in the first embodiment. The first operation portion 81B and the second operation portion 82B are in contact with each other at surfaces adjacent to each other in the longitudinal direction A. Even in this case, the stopper 300 can be attached to the first operation portion 81B or the second operation portion 82B to restrict the sliding of the first slider 812 or the second slider 822 toward the distal-end side A1 and release the restriction.

Also, the clip device according to the present disclosure may also include a stopper 300C as shown in FIG. 27 and FIG. 28. The stopper 300C is provided, for example, in a first slider groove 815C of the first operation portion main body 811C, and the proximal-end portion 300Cb is connected with a fixing pin 300p. The stopper 300C is provided to be rotatable around the fixing pin 300p along the longitudinal direction A. With this configuration, the stopper 300C does not restrict the sliding of the first slider 812 toward the distal-end side A1 when the distal-end portion 300Ca faces the distal-end side A1 as shown in FIG. 27. As shown in FIG. 28, the stopper 300C can restrict the sliding of the first slider 812 toward the distal-end side A1 when the proximal-end portion 300Cb faces the proximal-end side A2. The length of the stopper 300C in the longitudinal direction A can be arbitrarily adjusted according to the groove length of the first slider groove 815C and the range that is restricted by the first slider 812. Also, the stopper 300C may be provided in the second operation portion 82.

In any of the above embodiments, according to the tissue closure method according to the present disclosure, it is possible to grasp the tissues with a large or irregularly shape, and according to the clip device and the operation method of the clip device, operations of the arms that are independently movable become easy while maintaining the state of grasping the tissues, and it is possible to change the positions at which the tissues are grasped.

Third Embodiment

A clip device (endoscopic treatment device) 1100 according to a third embodiment of the present disclosure will be described with reference to FIG. 29 to FIG. 40. FIG. 29 is a view showing the overall configuration of the clip device (endoscopic treatment device) 1100 according to the third embodiment of the present disclosure.

Here, in the embodiments and modification examples described below, the same reference signs are given to mutually corresponding configurations, and descriptions of redundant features may be omitted. Also, in the following description, recitations indicating the relative or absolute arrangements such as "parallel", "orthogonal", "center", "coaxial" or the like do not only express such arrangements strictly, but also express a state of relative displacement at an angle or distance that provides the same function. Furthermore, the recitation of "patient" as used herein includes any organism and includes the recitation "tester". The patient may be a human or an animal.

[Clip Device (Endoscopic Treatment Device) 1100]

FIG. 29 is a view showing the overall configuration of the clip device (endoscopic treatment device) 1100. The clip device 1100 includes a treatment portion (clip) 1001 and an applicator 1200. The applicator 1200 also includes a traction member (connector) 1005 (see FIG. 36), an operation wire (wire) 1006 (see FIG. 36), a sheath 1007, and an operation portion 1008. In the following description, the treatment portion 1001 side in the longitudinal direction A of the clip device 1100 is defined as a tip side (distal-end side) A1 of the clip device 1100, and the operation portion 1008 side of the applicator 1200 of the clip device 1100 is defined as base side (proximal-end side) A2 of the clip device. In the clip device 1100, the treatment portion 1001, the traction member 1005 of the applicator 1200, the operation wire 1006, the sheath 1007 and the operation portion 1008 are arranged in this sequence from the distal-end side A1 to the proximal-end side A2 of the clip device 1100.

The clip device 1100 is used, for example, together with an endoscope (not shown). More specifically, the clip device 1100 is configured such that it is possible to introduce the treatment portion 1001 to the vicinity of the living tissue in the luminal cavity as a treatment object to perform the treatment relative to the living tissue by the surgeon operating the operation portion 1008 of the applicator 1200 to insert the sheath 1007 and the treatment portion 1001 provided at the distal-end side A1 of the sheath 1007 into a treatment device channel formed in the endoscope. In the present embodiment, the endoscope used with the clip device 1100 may be any flexible endoscope.

(Treatment Portion (Clip) 1001)

FIG. 30 is a view showing a state in which the treatment portion 1001 of the clip device 1100 is closed.

The treatment portion (clip) 1001 is used as a useful clip for patient therapeutic procedures such as performing hemostasis of tissues, closing perforations and hemostasis, suture contraction of internal wounds, marking lesions and tractions (mucosal protuberance), and other surgical procedures. The treatment portion 1001 is detached from the applicator 1200 by the operation of the surgeon and indwelled in the luminal cavity. The treatment portion 1001 includes a fixed arm 1002, a movable arm 1003, and a clip holder 1004, as shown in FIG. 30. Here, the movable arm 1003 has a first movable arm 1031 and a second movable arm 1032 that open and close relative to the fixed arm 1002. The first movable arm 1031 and the second movable arm 1032 are provided on both sides of the fixed arm 1002 and are arms that open independently in opposite directions.

A direction in which the movable arm 1003 of the treatment portion 1001 opens and closes relative to the fixed arm 1002 is defined as an open-close direction B or an up-down direction B, and a direction in which the first movable arm 1031 opens to be separated away from the fixed arm 1002 is defined as an upper side B1. Also, a direction in which the second movable arm 1032 opens to be separated away from the fixed arm 1002 is defined as a lower side B2. A direction orthogonal to the longitudinal direction A and the open-close direction B is defined as a thickness direction C or a left-right direction C.

[Fixed Arm 1002]

FIG. 35 is a view showing the fixed arm 1002 of the treatment portion 1001 of the clip device 1100.

The fixed arm 1002 is a rod-shaped member provided between the movable arms 1003 along the longitudinal direction A, as shown in FIG. 30 and FIG. 35. The fixed arm 1002 has a rod portion 1020A formed on the distal-end side A1 and a connection portion 1020B formed on the proximal-end side A2.

The rod portion 1020A is, for example, a substantially round rod-shaped member made of a material having biocompatibility, as shown in FIG. 35. The rod portion 1020A is exposed on its entire outer surface and includes a contact surface 1002c capable of being in contact with the tissue. The rod portion 1020A includes a distal-end portion 1002a and a rod-shaped portion 1002b.

The distal-end portion 1002a is provided at the distal end the rod-shaped portion 1002b. The distal-end portion 1002a is formed in a substantially disc shape having a diameter larger than that of the rod-shaped portion 1002b. Therefore, the fixed arm 1002 can be locked to the living tissue by hooking the distal-end portion 1002a of the fixed arm 1002 to the living tissue.

The rod-shaped portion 1002b is a substantially round rod-shaped member, and has the distal-end portion 1002a at its distal end. The rod-shaped portion 1002b includes a first opposite surface 1025, a second opposite surface 1026, and a plurality of protrusion portions 1027.

The first opposite surface 1025 of the contact surface 1002c is formed on the rod-shaped portion 1002b and faces the first movable arm 1031 provided on the upper side B1 in the open-close direction B.

The second opposite surface 1026 of the contact surface 1002c is formed on the rod-shaped portion 1002b and faces the second movable arm 1032 provided on the lower side B2 in the open-close direction B.

The plurality of protrusion portions 1027 are protrusion portions provided on the fixed arm 1002, as shown in FIG. 30 and FIG. 35. The protrusion portion 1027 includes a first protrusion portion 1027a provided on the first opposite surface 1025 and a second protrusion portion 1027b provided on the second opposite surface 1026. The first protrusion portion 1027a protrudes from the first opposite surface 1025 toward the first movable arm 1031 arranged on the upper side B1 in the open-close direction B. The second protrusion 1027b protrudes from the second opposite surface 1026 toward the second movable arm 1032 arranged on the lower side B2 in the open-close direction B.

The connection portion 1020B is provided on the proximal-end side A2 of the rod portion 1020A. The connection portion 1020B is formed in a plate shape, and the plate thickness direction of the connection portion 1020B substantially coincides with the thickness direction C. Here, in the thickness direction C, one side of the connection portion 1020B is defined as a left side C1. Also, in the thickness direction C, the direction opposite to the left side C1 on one side of the connection portion 1020B is defined as a right side C2. The connection portion 1020B connects the fixed arm 1002 and the movable arm 1003 with the clip holder 1004 and the traction member 1005, which will be described later. The connection portion 1020B includes a through hole 1021, a through hole 1022, an engagement groove 1023, and a tail 1024, as shown in FIG. 35.

The through hole 1021 is a hole penetrating through the connection portion 1020B in the thickness direction C. The through hole 1021 is formed on the distal-end side A1 of the connection portion 1020B. A first rotation pin 1211 is engaged with the through hole 1021 from the left side C1.

The through hole 1022 is a hole penetrating through the connection portion 1020B in the thickness direction C. The through hole 1022 is formed on the distal-end side A1 of the connection portion 1020B. The through hole 1022 is provided at substantially the same position as that of the through hole 1021 in the longitudinal direction A. A second rotation pin 1221 is engaged with the through hole 1022 from the right side C2.

The engagement groove 1023 is a groove extending along the longitudinal direction A formed in the connection portion 1020B. The engagement groove 1023 is a groove penetrating the connection portion 1020B in the thickness direction C.

The tail 1024 is formed on the proximal-end side A2 of the connection portion 1020B of the fixed arm 1002. The tail 1024 is connected to the clip holder 1004 which will be described later.

[Movable Arm 1003]

FIG. 31 is a view showing a state in which the first movable arm 1031 of the treatment portion 1001 of the clip device 1100 is opened when viewed from the left side C1 in the thickness direction C. FIG. 32 is a view showing a state in which the second movable arm 1032 of the treatment portion 1001 of the clip device 1100 is opened when viewed from the right side C2 in the thickness direction C. FIG. 33 is a view showing the first movable arm 1031 of the treatment portion 1001 of the clip device 1100. FIG. 34 is a view showing the second movable arm 1032 of the treatment portion 1001 of the clip device 1100. The movable arm 1003 has the first movable arm 1031 and the second movable arm 1032, as shown in FIG. 30 to FIG. 34. The first movable arm 1031 is arranged on the upper side B1 of the fixed arm 1002 in the open-close direction B. The second movable arm 1032 is arranged on the lower side B2 of the fixed arm 1002 in the open-close direction B. The first movable arm 1031 and the second movable arm 1032 can be opened and closed independently.

As shown in FIG. 30, FIG. 31 and FIG. 33, the first movable arm 1031 is provided so as to be able to open and close toward the upper side B1 in the open-close direction B relative to the distal-end side A1 of the fixed arm 1002. Specifically, the first movable arm 1031 is rotatably attached to the fixed arm 1002 by a first rotation pin 1211 provided in the first through hole 1313. The first movable arm 1031 has a first slide slot 1310, a first engagement portion 1311, a first through hole 1313 and a first arm portion 1312.

The first slide slot 1310 is provided on the proximal-end side A2 of the first movable arm 1031, as shown in FIG. 33. The first slide slot 1310 engages with a first slide pin 1511, which will be described later.

The first engagement portion 1311 is an elastic member having elasticity in the open-close direction B provided on the proximal-end side A2 of the first movable arm 1031. The first engagement portion 1311 is, for example, a leaf spring. The first engagement portion 1311 is accommodated inside the clip holder 1004 when the first movable arm 1031 is closed relative to the fixed arm 1002. Specifically, as shown in FIG. 31, in a state of opening the first movable arm 1031 relative to the fixed arm 1002, the first engagement portion 1311 is positioned outside the clip holder 1004, which will be described later. On the other hand, as shown in FIG. 30, the first engagement portion 1311 is accommodated inside the clip holder 1004 in a state of closing the first movable arm 1031 relative to the fixed arm 1002. In the state in which the first movable arm 1031 is closed relative to the fixed arm 1002, a length L1 of the first engagement portion 1311 in the open-close direction B is substantially equal to or slightly larger than the inner diameter of the clip holder 1004.

In the present embodiment, when the first movable arm 1031 transitions from the closed state to the open state relative to the fixed arm 1002 in the open-close direction B, the first engagement portion 1311 rotates together with the first movable arm 1031, and the most proximal end of the first engagement portion 1311 enters the inside of the clip holder 1004. During the process of the first engagement portion 1311 entering the inside of the clip holder 1004, each portion of the first engagement portion 1311 that contacts the clip holder 1004 may be rounded or processed such as chamfering so as not to damage the inner circumferential surface of the clip holder 1004.

The first through hole 1313 is a hole penetrating through the first movable arm 1031 in the thickness direction C. The first through hole 1313 is arranged on the left side C1 of the through hole 1021 provided in the fixed arm 1002 in the thickness direction C and engages with the first rotation pin 1211. The first rotation pin 1211 connects the first through hole 1313 and the through hole 1021. With this configuration, the first movable arm 1031 can rotate about the first through hole 1313 as a rotation center relative to the fixed arm 1002.

As shown in FIG. 33, the first arm portion 1312 is formed in a substantially cup shape by the resin or metal for example. By rotating the first arm portion 1312 along the open-close direction B relative to the fixed arm 1002, the distal-end portion thereof approaches the distal-end portion 1002a of the fixed arm 1002 and can sandwich the living tissue. For example, the distal-end portion of the first arm portion 1312 may be formed with a distal end in a claw shape for definitely clamping the living tissue. However, the first arm portion 1312 is not limited to the shape according to the present embodiment and may be configured following various conventional shapes. Also, the first arm portion 1312 is parallel to the fixed arm 1002 in the longitudinal direction A in a state of closing the first movable arm 1031 relative to the fixed arm 1002. The first arm portion 1312 has a first grasping surface 1312a, a first outer surface 1312b, an opening portion 1314, and a piercing portion (anchor, first arm spike) 1910.

The first grasping surface 1312a is an inner surface that contacts the tissue in the open-close direction B and faces the fixed arm 1002.

The first outer surface 1312b is a surface provided on the side opposite to the first grasping surface 1312a in the open-close direction B.

In the open-close direction B, the first arm portion 1312 is formed with a recess on the side of the first grasping surface 1312a and a rounded bulge on the side of the first outer surface 1312b. Therefore, when the tissue is grasped by the first movable arm 1031 and the fixed arm 1002, the tissue is accommodated in the recess portion included in the first movable arm 1031.

As shown in FIG. 33, the opening portion 1314 opens on the first grasping surface 1312a of the first arm portion 1312. The opening portion 1314 may be a concave portion with a bottom surface or may be a penetrating hole that penetrates the first arm portion 1312 in the open-close direction B. The opening portion 1314 has a first opening portion 1315 and a second opening portion 1316. The first opening portion 1315 and the second opening portion 1316 are arrayed along the longitudinal direction A. In the present embodiment, as shown in FIG. 33, the first opening portion 1315 and the second opening portion 1316 are formed to extend along the longitudinal direction A and in a substantially rectangular shape; however, the shape of the opening portion 1314 is not particularly limited. For example, the opening portion 1314 may be formed in a polygonal shape and may be formed in a triangle shape or a circular shape. Also, the first opening portion 1315 and the second opening portion 1316 may be formed in different shapes.

The first opening portion 1315 is arranged on the distal-end side A1 relative to the central portion of the first arm portion 1312. The first opening portion 1315 is formed by processing the first arm portion 1312 from the side of the first grasping surface 1312a by stamping processing, drilling processing or the like. The first opening portion 1315 has an edge portion 1315a on the edge of the first grasping surface 1312a side. Also, the edge portion 1315a has a distal-end edge portion 1315b on the distal-end side A1.

The second opening portion 1316 is arranged on the proximal-end side A1 relative to the first opening portion 1315. Similar to the first opening portion 1315, the second opening portion 1316 is formed by processing the first arm portion 1312 from the side of the first grasping surface 1312a by stamping processing, drilling processing or the like. The second opening portion 1316 has an edge portion 1316a on the edge of the first grasping surface 1312a side. Also, the edge portion 1316a has a distal-end edge portion 1316b on the distal-end side A1.

As shown in FIG. 33, the piercing portion (anchor) 1910 is an elastically deformable leaf spring formed on the first arm portion 1312. A plurality of piercing portions 1910 may be provided on the first arm portion 1312. The piercing portion 1910 has a first piercing portion 1911 and a second piercing portion 1912 according to the present embodiment. The first piercing portion 1911 and the second piercing portion 1912 are arrayed along the longitudinal direction A, similar to the opening portion 1314 described above.

The first piercing portion 1911 is arranged at the distal-end side A1 relative to the central portion of the first arm portion 1312. The first piercing portion 1911 has substantial the same shape with the first opening portion 1315. The first piercing portion 1911 faces the proximal-end side A2 in the state in which the first movable arm 1031 is closed relative to the fixed arm 1002. The first piercing portion 1911 has a first connection portion 1911a at the distal-end side A1. The first connection portion 1911a is connected to the distal-end edge portion 1315b of the first opening portion 1315. Also, the first piercing portion 1911 has a first piercing distal-end portion 1911b as the distal end of the first piercing portion 1911 and at the proximal-end side A2 of the first connection portion 1911a. The first piercing distal-end portion 1911b is arranged at the lower side B2 in the open-close direction B relative to the first connection portion 1911a in the state in which the first movable arm 1031 is closed relative to the fixed arm 1002. Accordingly, the first piercing portion 1911 is provided in a state of protruding toward the lower side B2 and being inclined relative to the first grasping surface 1312a.

The second piercing portion 1912 is arranged at the proximal-end side A2 of the first piercing portion 1911. The second piercing portion 1912 has substantially the same shape with the second opening portion 1316. The second piercing portion 1912 faces the proximal-end side A2 in the state in which the first movable arm 1031 is closed relative to the fixed arm 1002. The second piercing portion 1912 has a second connection portion 1912a at the distal-end side A1. The second connection portion 1912a is connected to the distal-end edge portion 1316b of the second opening portion 1316. Also, the second piercing portion 1912 has a second piercing distal-end portion 1912b as the distal end of the second piercing portion 1912 and at the proximal-end side A2 of the second connection portion 1912a. The second piercing distal-end portion 1912b is arranged at the lower side B2 in the open-close direction B relative to the second connection portion 1912a in the state in which the first movable arm 1031 is closed relative to the fixed arm 1002. Accordingly, the second piercing portion 1912 is provided in a state of protruding toward the lower side B2 and being inclined relative to the first grasping surface 1312a.

The first piercing portion 1911 and the second piercing portion 1912 are formed by being bent toward the lower side B2 in the open-close direction B by, for example, punching processing, drilling processing or the like. At this time, the first piercing portion 1911 is a part of the first arm portion 1312, and the first connection portion 1911a is a portion being bent. Also, the second piercing portion 1912 is a part of the first arm portion 1312, and the second connection portion 1912a is a portion being bent. In this embodiment, the piercing portion 1910 having the first piercing portion 1911 and the second piercing portion 1912 is a part of the first arm portion 1312; however, the first arm portion 1312 and the piercing portion 1910 may be individually formed as different members. In this case, the first connection portion 1911a and the second connection portion 1912a may be connected to the distal-end edge portion 1315b of the first opening portion 1315 or the distal-end edge portion 1316b of the second opening portion 1316 by welding, adhesion or the like. Also, the first arm portion 1312 may not have the opening portion 1314, and the first connection portion 1911*a* and the second connection portion 1912*a* may be directly connected to any position of the first arm portion 1312. Furthermore, the piercing portion 1910 does not have to be formed in the shape following the shape of the opening portion 1314.

In this embodiment, the first arm portion 1312 is parallel to the fixed arm 1002 in the longitudinal direction A in the state in which the first movable arm 1031 is closed relative to the fixed arm 1002. Accordingly, as shown in FIG. 30 or FIG. 33, the piercing portion 1910 may be formed to be inclined from the first grasping surface 1312*a* of the first arm portion 1312 toward the lower side B2 in the open-close direction B at an angle greater than 0 degrees and within 90 degrees. By setting this angle, when the tissue is grasped and enters between the fixed arm 1002 and the first movable arm 1031, the piercing portion 1910 protruding from the first grasping surface 1312*a* toward the lower side B2 is pushed to the upper side B1. The piercing portion 1910, which is a leaf spring, pushes back the tissue to the lower side B2 as the opposite direction of the upper side B1 in which the piercing portion 1910 is pushed in the open-close direction B due to the elastic restoring force. Then, the tissue is biased by the piercing portion 1910 to the direction (lower side B2) in which the first movable arm 1031 is closed in addition to the state of being grasped by the fixed arm 1002 and the first movable arm 1031. Accordingly, the fixed arm 1002 and the first movable arm 1031 can firmly grasp the tissue.

As shown in FIG. 30, FIG. 32 and FIG. 34, the second movable arm 1032 is provided so as to be openable and closable toward the lower end side B2 in the open-close direction B relative to the distal-end side A1 of the fixed arm 1002. Specifically, the second movable arm 1032 is provided to be openable and closable to the side opposite to the first movable arm 1031 relative to the fixed arm 1002 by means of a second rotation pin 1221 provided in the second through hole 1323. The second movable arm 1032 has a second slide slot 1320, a second engagement portion 1321, a second through hole 1323 and a second arm portion 1322.

The second slide slot 1320 is provided on the proximal-end side A2 of the second movable arm 1032, as shown in FIG. 34. The second slide slot 1320 engages with the second slide pin 1521, which will be described later.

The second engagement portion 1321 is an elastic member provided on the proximal-end side A2 of the second movable arm 1032 and having elasticity in the open-close direction B. The second engagement portion 1321 is, for example, a leaf spring. The second engagement portion 1321 is accommodated inside the clip holder 1004 when the second movable arm 1032 is closed relative to the fixed arm 1002. Specifically, as shown in FIG. 32, when the second movable arm 1032 is opened relative to the fixed arm 1002, the second engagement portion 1321 is positioned outside the clip holder 1004, which will be described later. On the other hand, as shown in FIG. 30, the second engagement portion 1321 is accommodated inside the clip holder 1004 when the second movable arm 1032 is closed relative to the fixed arm 1002. In the state in which the second movable arm 1032 is closed relative to the fixed arm 1002, the length L2 of the second engagement portion 1321 in the open-close direction B is substantially equal to or substantially larger than the inner diameter of the clip holder 1004.

In the present embodiment, when the second movable arm 1032 transitions from the closed state to the open state relative to the fixed arm 1002 in the open-close direction B, the second engagement portion 1321 rotates together with the second movable arm 1032, and the second engagement portion 1321 enters the inside of the clip holder 1004 from the most proximal end of the second engagement portion 1321. Each portion of the second engagement portion 1321 that contacts the clip holder 1004 may be formed in the rounded shape or processed such as the chamfering so as not to damage the inner circumferential surface of the clip holder 1004 in the process of the second engagement portion 1321 entering the inside of the clip holder 1004.

The second through hole 1323 is a hole penetrating through the second movable arm 1032 in the thickness direction C. The second through hole 1323 is arranged on the right side C2 of the through hole 1021 provided in the fixed arm 1002 in the thickness direction C and engages with the second rotation pin 1221. The second rotation pin 1221 connects the second through hole 1323 and the through hole 1022. This configuration allows the second movable arm 1032 to be rotatable about the second through hole 1323 as a center relative to the fixed arm 1002.

The second arm portion 1322 is formed from the resin or metal in a substantial cup shape. By rotating the second arm portion 1322 following the open-close direction B relative to the fixed arm 1002, the distal-end portion of the second arm portion 1332 approaches the distal-end portion 1002*a* of the fixed arm 1002 so as to clamp the living tissue. Similar to the first arm portion 1312, in the second arm portion 1322, for example, the distal-end thereof may be formed into the claw shape in order to definitely clamp the living tissue. However, the second arm portion 1322 is not limited to the shape according to the present embodiment and may be formed following the various conventional structure. Also, the second arm portion 1322 is parallel to the fixed arm 1002 in the longitudinal direction A in the state of closing the second movable arm 1032 relative to the fixed arm 1002. The second arm portion 1322 has a second grasping surface 1322*a*, a second outer surface 1322*b*, an opening portion 1324 and a piercing portion (anchor, second arm spike) 1920.

The second grasping surface 1322*a* is an inner surface that contacts the tissue in the open-close direction B and faces the fixed arm 1002.

The second outer surface 1322*b* is a surface provided on the side opposite to the second grasping surface 1322*a* in the open-close direction B.

As shown in FIG. 34, in the open-close direction B, the second arm portion 1322 is formed with a recess on the side of the second grasping surface 1322*a* and a rounded bulge on the side of the second outer surface 1322*b*. Therefore, when the tissue is grasped by the second movable arm 1032 and the fixed arm 1002, the tissue is accommodated in the recess portion of the second movable arm 1032.

As shown in FIG. 34, the opening portion 1324 opens on the second grasping surface 1322*a* of the second arm portion 1322. The opening portion 1324 may be a concave portion with a bottom surface or may be a penetrating hole that penetrates the second arm portion 1322 in the open-close direction B. The opening portion 1324 has a first opening portion 1325 and a second opening portion 1326. The first opening portion 1325 and the second opening portion 1326 are arrayed along the longitudinal direction A. In the present embodiment, as shown in FIG. 34, the first opening portion 1325 and the second opening portion 1326 are formed to extend along the longitudinal direction A and in a substantially rectangular shape; however, the shape of the opening portion 1324 is not particularly limited. For example, the opening portion 1324 may be formed in a polygonal shape and may be formed in a triangle shape or a circular shape.

Also, the first opening portion 1325 and the second opening portion 1326 may be formed in different shapes.

The first opening portion 1325 is arranged on the distal-end side A1 relative to the central portion of the first arm portion 1322. The first opening portion 1325 is formed by processing the second arm portion 1322 from the side of the second grasping surface 1322a by stamping processing, drilling processing or the like. The first opening portion 1325 has an edge portion 1325a on the edge of the second grasping surface 1322a side. Also, the edge portion 1325a has a distal-end edge portion 1325b on the distal-end side A1.

The second opening portion 1326 is arranged on the proximal-end side A2 relative to the first opening portion 1325. Similar to the first opening portion 1325, the second opening portion 1326 is formed by processing the second arm portion 1322 from the side of the second grasping surface 1322a by stamping processing, drilling processing or the like. The second opening portion 1326 has an edge portion 1326a on the edge of the second grasping surface 1312a side. Also, the edge portion 1326a has a distal-end edge portion 1326b on the distal-end side A1.

As shown in FIG. 34, the piercing portion (anchor) 1920 is an elastically deformable leaf spring formed on the second arm portion 1322. A plurality of piercing portions 1920 may be provided on the second arm portion 1322. The piercing portion 1920 has a first piercing portion 1921 and a second piercing portion 1922 according to the present embodiment. The first piercing portion 1921 and the second piercing portion 1922 are arrayed along the longitudinal direction A, similar to the opening portion 1324 described above.

The first piercing portion 1921 is arranged at the distal-end side A1 relative to the central portion of the second arm portion 1322. The first piercing portion 1921 has substantial the same shape with the first opening portion 1325. The first piercing portion 1921 faces the proximal-end side A2 in the state in which the second movable arm 1032 is closed relative to the fixed arm 1002. The first piercing portion 1921 has a first connection portion 1921a at the distal-end side A1 of the first piercing portion 1921. The first connection portion 1921a is connected to the distal-end edge portion 1325b of the first opening portion 1325. Also, the first piercing portion 1921 has a first piercing distal-end portion 1921b as the distal end of the first piercing portion 1921 and at the proximal-end side A2 of the first connection portion 1921a. The first piercing distal-end portion 1921b is arranged at the upper side B1 in the open-close direction B relative to the first connection portion 1921a in the state in which the second movable arm 1032 is closed relative to the fixed arm 1002. Accordingly, the first piercing portion 1921 is provided in a state of protruding toward the upper side B1 and being inclined relative to the second grasping surface 1322a.

The second piercing portion 1922 is arranged at the proximal-end side A2 of the first piercing portion 1921. The second piercing portion 1922 has substantially the same shape with the first opening portion 1325. The second piercing portion 1922 faces the proximal-end side A2 in the state in which the second movable arm 1032 is closed relative to the fixed arm 1002. The second piercing portion 1922 has a second connection portion 1922a at the distal-end side A1. The second connection portion 1922a is connected to the distal-end edge portion 1326b of the second opening portion 1326. Also, the second piercing portion 1922 has a second piercing distal-end portion 1922b as the distal end of the second piercing portion 1922 and at the proximal-end side A2 of the second connection portion

1922a. The second piercing distal-end portion 1922b is arranged at the upper side B1 in the open-close direction B relative to the second connection portion 1922a in the state in which the second movable arm 1032 is closed relative to the fixed arm 1002. Accordingly, the second piercing portion 1922 is provided in a state of protruding toward the upper side B1 and being inclined relative to the second grasping surface 1322a.

The first piercing portion 1921 and the second piercing portion 1922 are formed by being bent toward the upper side B1 in the open-close direction B by, for example, punching processing, drilling processing or the like. At this time, the first piercing portion 1921 is a part of the second arm portion 1322, and the first connection portion 1921a is a portion being bent. Also, the second piercing portion 1922 is a part of the second arm portion 1322, and the second connection portion 1922a is a portion being bent. In this embodiment, the piercing portion 1920 having the first piercing portion 1921 and the second piercing portion 1922 is a part of the second arm portion 1322; however, the second arm portion 1322 and the piercing portion 1920 may be individually formed as different members. In this case, the first connection portion 1921a and the second connection portion 1922a may be connected to the distal-end edge portion 1325b of the first opening portion 1325 or the distal-end edge portion 1326b of the second opening portion 1326 by welding, adhesion or the like. Also, the second arm portion 1322 may not have the opening portion 1324, and the first connection portion 1921a and the second connection portion 1922a may be directly connected to any position of the second arm portion 1322. Furthermore, the piercing portion 1920 does not have to be formed in the shape following the shape of the opening portion 1324.

In this embodiment, the second arm portion 1322 is parallel to the fixed arm 1002 in the longitudinal direction A in the state in which the second movable arm 1032 is closed relative to the fixed arm 1002. Accordingly, more specifically, as shown in FIG. 30 or FIG. 34, the piercing portion 1920 may be formed to be inclined from the second grasping surface 1322a of the second arm portion 1322 toward the upper side B1 in the open-close direction B at an angle greater than 0 degrees and within 90 degrees. By setting this angle, when the tissue is grasped and enters between the fixed arm 1002 and the second movable arm 1032, the piercing portion 1920 protruding from the second grasping surface 1322a toward the upper side B1 is pushed to the lower side B2. The piercing portion 1920, which is a leaf spring, pushes back the tissue to the upper side B1 as the opposite direction B of the lower side B2 in which the piercing portion 1920 is pushed in the open-close direction B due to the elastic restoring force. Then, the tissue is biased by the piercing portion 1920 to the direction (upper side B1) in which the second movable arm 1032 is closed in addition to the state of being grasped by the fixed arm 1002 and the second movable arm 1032. Accordingly, the fixed arm 1002 and the second movable arm 1032 can firmly grasp the tissue.

[Clip Holder 1004]

The clip holder 1004 is a pipe formed in a cylindrical shape having a longitudinal axis, as shown in FIG. 30. In the present embodiment, the clip holder 1004 is arranged along the longitudinal direction A. The clip holder 1004 is configured such that at least the proximal-end portions of the movable arm 1003 and the fixed arm 1002 in the closed state can enter therein. Also, the clip holder 1004 rotates together with the first movable arm 1031 and the second movable arm 1032 when the clip device 1100 is rotated in the circumferential direction.

The clip holder 1004 has groove portions 1041. The groove portions 1041 are formed on the distal-end side A1 of the clip holder 1004 and on the upper side B1 and the lower side B2 in the open-close direction B. The groove portions 1041 are, for example, slits formed from the distal end toward the proximal-end side A2, and have dimensions suitable for the first engagement portion 1311 of the first movable arm 1031 and the second engagement portion 1321 of the second movable arm 1032 to enter inside of the clip holder 1004.

The clip holder 1004 may include an engaging hole (not shown) formed at the base end A2 and with which the pair of tails 1024 of the fixed arm 1002 can be engaged, for example. Accordingly, the fixed arm 1002 is thereby attached to the clip holder 1004. The fixed arm 1002 and the clip holder 1004 may be integrally molded.

The clip holder 1004 has an inner diameter equal to or slightly shorter than the length L1 of the first engagement portion 1311 and the length L2 of the second engagement portion 1321. The clip holder 1004 can accommodate the first engagement portion 1311 and the second engagement portion 1321 inside therein. When the first movable arm 1031 rotates toward the lower side B2 in the open-close direction B, the first engagement portion 1311 enters the inside of the clip holder 1004 through the groove portion 1041. Also, when the second movable arm 1032 rotates toward the upper side B1 in the open-close direction B, the second engagement portion 1321 enters the inside of the clip holder 1004 from the groove portion 1041. The first movable arm 1031 can be opened again relative to the fixed arm 1002 until the first engagement portion 1311 is engaged to and locked by the clip holder 1004. Also, the second movable arm 1032 can be opened again relative to the fixed arm 1002 until the second engagement portion 1321 is engaged to and locked by the clip holder 1004.

When the first engagement portion 1311 is further pulled toward the proximal-end side A2 in the state in which the first engagement portion 1311 is accommodated inside the clip holder 1004, the first engagement portion 1311 abuts on the inner circumferential surface of the clip holder 1004 to be elastically deformed so as to be engaged with and locked inside the clip holder 1004. Also, when the second engagement portion 1321 is further pulled toward the proximal-end side A2 in the state in which the second engagement portion 1321 is accommodated inside the clip holder 1004, the second engagement portion 1321 abuts on the inner circumferential surface of the clip holder 1004 to be elastically deformed so as to be engaged with and locked inside the clip holder 1004. Accordingly, the closed state of the first movable arm 1031 and the second movable arm 1032 relative to the fixed arm 1002 is maintained. It is noted that the clip holder 1004 can at first lock either one of the first engagement portion 1311 and the second engagement portion 1321.

[Applicator 1200]

The applicator 1200 is a portion of the clip device 1100 that is not indwelled in the luminal cavity except for the treatment portion 1001. The applicator 1200 includes a traction member (connector) 1005, an operation wire 1006, a sheath 1007, and an operation portion 1008, as shown in FIG. 29 and FIG. 36.

[Traction Member 1005]

FIG. 36 is a view showing the traction member 1005 of the applicator 1200 of the clip device 1100.

As shown in FIG. 36, the traction member 1005 includes a first traction member 1051 and a second traction member 1052. Since the first traction member 1051 and the second traction member 1052 have substantially the same configuration, the figure of the second traction member 1052 is omitted.

The first traction member 1051 is arranged on the left side C1 relative to the connection portion 1020B of the fixed arm 1002. The first traction member 1051 connects the distal-end portion 1051a to the proximal-end side A2 of the first movable arm 1031. Also, the proximal-end side A2 of the first traction member 1051 is connected to the distal-end portion of the first operation wire 1061. The first traction member 1051 includes a first slide pin hole 1510 and a first slide pin 1511 at the distal-end portion thereof.

The first slide pin hole 1510 is a hole provided in the distal-end portion 1051a of the first traction member 1051. The first slide pin 1511 can be engaged with the first slide pin hole 1510. The first slide pin hole 1510 has a notch portion 1512 on the distal-end side A1.

The first slide pin 1511 connects the first slide pin hole 1510, the first slide slot 1310 of the first movable arm 1031 and the engagement groove 1023. The first slide pin 1511 can advance and retract along the first slide slot 1310 and the engagement groove 1023 by sliding the first slider 1812 of the operation portion 1008 along the longitudinal direction A. When the first slide pin 1511 advances along the first slide slot 1310 and the engagement groove 1023 toward the distal-end side A1, the first movable arm 1031 rotates around the first rotation pin 1211 as the center to open in the open-close direction B to enter the open state relative to the fixed arm 1002. When the first slide pin 1511 retracts along the first slide slot 1310 and the engagement groove 1023 toward the proximal-end side A2, the first movable arm 1031 rotates around the first rotation pin 1211 as the center to close in the open-close direction B to enter the closed state relative to the fixed arm 1002. Accordingly, the first movable arm 1031 is able to open and close relative to the fixed arm 1002 in the open-close direction B. Here, the state in which the first movable arm 1031 is closed relative to the fixed arm 1002 includes the state in which a distance between the distal end of the first movable arm 1031 and the distal end of the fixed arm 1002 is substantially zero. In this state, the first movable arm 1031 and the fixed arm 1002 can clamp the living tissues as the treatment target between the first movable arm 1031 and the fixed arm 1002.

The second traction member 1052 is arranged on the right side C2 relative to the connection portion 1020B of the fixed arm 1002. The second traction member 1052 connects the distal-end portion 1052a to the proximal-end side A2 of the second movable arm 1032. Also, the proximal-end side A2 of the second traction member 1052 is connected to the distal-end portion of the second operation wire 1062. The second traction member 1052 has a second slide pin hole 1520 and a second slide pin 1521 in the distal-end portion 1052a.

The second slide pin hole 1520 is provided in the distal-end portion 1052a of the second traction member 1052 and is a hole with which the second slide pin 1521 can be engaged. The second slide pin hole 1520 has a notch portion 1522 on the distal-end side A1.

The second slide pin 1521 connects the second slide pin hole 1520, the second slide slot 1320 of the second movable arm 1032 and the engagement groove 1023. The second slide pin 1521 can advance and retract along the second slide slot 1320 and the engagement groove 1023 by sliding the second slider 1822 of the operation portion 1008 along the longitudinal direction A. When the second slide pin 1521 advances along the second slide slot 1320 and the engagement groove 1023 toward the distal-end side A1, the second movable arm 1032 rotates around the second rotation pin 1221 as the center to open in the open-close direction B to enter the open state relative to the fixed arm 1002. When the second slide pin 1521 retracts along the second slide slot 1320 and the engagement groove 1023 toward the proximal-end side A2, the second movable arm 1032 rotates around the second rotation pin 1221 as the center to close in the open-close direction B to enter the closed state relative to the fixed arm 1002. Accordingly, the second movable arm 1032 is able to open and close relative to the fixed arm 1002 in the open-close direction B. Here, the state in which the second movable arm 1032 is closed relative to the fixed arm 1002 includes the state in which a distance between the distal end of the second movable arm 1032 and the distal end of the fixed arm 1002 is substantially zero. In this state, the distal end of the second movable arm 1032 and the distal end of the fixed arm 1002 can clamp the living tissues as the treatment target.

In the state in which the first movable arm 1031 is closed relative to the fixed arm 1002, and the first engagement portion 1311 is locked inside the clip holder 1004, the first slider 1812 of the operation portion 1008 is slid toward the proximal-end side A2. As a result, the notch portion 1512 is deformed or broken so as to be detached from the first slide pin 1511. The first traction member 1051 is separated from the connected fixed arm 1002 and the first movable arm 1031. Also, with regard to the second slide pin 1521, in the state in which the second movable arm 1032 is closed with the fixed arm 1002 and the second engagement portion 1321 is locked inside the clip holder 1004, the second slider 1822 of the operation portion 1008 is slid toward the proximal-end side A2. As a result, the notch portion 1522 is deformed or broken so as to be detached from the second slide pin 1521. The second traction member 1052 is separated from the connected fixed arm 1002 and the second movable arm 1032. When the first traction member 1051 and the second traction member 1052 are separated from the fixed arm 1002, the first movable arm 1031 and the second movable arm 1032, it is possible for the clip device 1100 to indwell the treatment portion 1001 including the fixed arm 1002, the movable arm 1003, and the clip holder 1004 in the luminal cavity in the state of grasping the tissues.

[Operation Wire 1006]

As shown in FIG. 36, the operation wire 1006 has a first operation wire 1061 and a second operation wire 1062. Since the first operation wire 1061 and the second operation wire 1062 have substantially the same configuration, the figure of the second operation wire 1062 is omitted.

The first operation wire 1061 connects the distal-end portion to the proximal-end portion of the first traction member 1051. The proximal-end portion of the first operation wire 1061 is fixed to the first slider 1812 of the operation portion 1008. The first operation wire 1061 is inserted through the sheath 1007 so as to be advanceable and retractable therein. The first operation wire 1061 may be formed of, for example, a metal single wire or twisted wire. Also, the outer circumferential surface of the first operation wire 1061 may be covered with a non-conductive member or the like. The first operation wire 1061 is fixed to the first traction member 1051 by various known methods such as adhesion, welding and the like. The first operation wire 1061 can advance or retract the first traction member 1051 by sliding the first slider 1812 of the operation portion 1008 attached to the proximal-end portion.

With regard to the second operation wire 1062, the distal-end portion thereof is connected to the proximal-end portion of the second traction member 1052. The proximal-end portion of the second operation wire 1062 is fixed to the second slider 1822 of the operation portion 1008. The second operation wire 1062 is inserted through the sheath 1007 so as to be advanceable and retractable therein. The second operation wire 1062 may be formed of, for example, a metal single wire or twisted wire. Further, the outer circumferential surface of the second operation wire 1062 may be covered with a non-conductive member or the like. The second operation wire 1062 is fixed to the second traction member 1052 by various known methods, such as adhesion, welding and the like. The second operation wire 1062 can advance or retract the second traction member 1052 by sliding the second slider 1822 of the operation portion 1008 attached to the proximal-end portion.

[Sheath 1007]

For example, as shown in FIG. 29, the sheath 1007 is configured to extend along the longitudinal direction A and is an elongated member that can be inserted into the luminal cavity. The sheath 1007 is made of an insulating material such as a fluororesin including PTFE (polytetrafluoroethylene) or a resin material such as HDPE (high density polyethylene). The sheath 1007 has the flexibility and can easily change the shape following the curved shape of the luminal tissue or the like inside the luminal cavity so as to be inserted into and removed from the channel (not shown) of the clip device 1100. A proximal-end portion 1007b of the sheath 1007 is connected to the operation portion 1008, and a distal-end portion 1007a is connected to the proximal-end portion of the clip holder 1004. Also, the first operation wire 1061 and the second operation wire 1062 are inserted through the sheath 1007.

[Operation Portion (Handle) 1008]

The operation portion 1008 includes a distal-end portion 1080a, a first operation portion 1081, and a second operation portion 1082, and extends in the longitudinal direction A, as shown in FIG. 29. The distal-end portion 1080a is connected to the proximal-end portion 1007b of the sheath 1007, as shown in FIG. 29. In the present embodiment, the directions in which the first operation portion 1081 and the second operation portion 1082, which are connected from the distal end portion 1080a to the distal end portion 1080a of the operation portion 1008, branch off from each other substantially coincide with the open-close direction B. The first operation portion 1081 and the second operation portion 1082 extend toward the upper side B1 and the lower side B2 in the up-down direction B from the distal-end portion 1080a toward the proximal-end side A2.

The first operation portion 1081 has a first operation portion main body 1811, a first slider 1812, and a finger hook portion 1813.

The first operation portion main body 1811 operates the first traction member 1051 and the first movable arm 1031 via the first operation wire 1061. The first operation portion main body 1811 of the first operation portion 1081 is formed in a substantially round rod shape extending in the longitudinal direction A.

The first slider 1812 is provided to slide in the longitudinal direction A to be advanceable and retractable in the first operation portion main body 1811. The proximal-end of the first operation wire 1061 is fixed to the first slider 1812. When the first slider 1812 is advanced and retracted along the first operation portion main body 1811 in the longitudinal direction A, the first operation wire 1061 and the first traction member 1051 fixed to the distal-end of the first operation wire 1061 are moved to advance and retract along the longitudinal direction A. Furthermore, when the first traction member 1051 advances and retracts along the longitudinal direction A, the first slide pin 1511 of the first traction member 1051 advances and retracts along the first slide slot 1310. Then, the first movable arm 1031 opens in the open-close direction B with the first rotation pin 1211 as the center. With this configuration, when the first slider advances and retracts along the first operation portion main body 1811 in the longitudinal direction A, it is possible to drive the first movable arm 1031 to perform the open-close operation in the open-close direction B.

The finger hook portion 1813 is a substantially ring-shaped finger hooking portion formed on the proximal-end side A2 of the first operation portion main body 1811.

The second operation portion 1082 has a second operation portion main body 1821, a second slider 1822, and a finger hook portion 1823.

The second operation portion main body 1821 operates the second traction member 1052 and the second movable arm 1032 via the second operation wire 1062. The second operation portion main body 1821 of the second operation portion 1082 is formed in a rod shape extending in the longitudinal direction A.

The second slider 1822 is provided to slide in the longitudinal direction A to be advanceable and retractable in the second operation portion main body 1821. A proximal-end of the second operation wire 1062 is fixed to the second slider 1822. The second slider 1822 is provided to be inserted through the second operation portion main body 1821. When the second slider 1822 advances and retracts along the second operation portion main body 1821 in the longitudinal direction A, the second operation wire 1062 and the second traction member 1052 fixed to the distal-end portion of the second operation wire 1062 are moved to advance and retract along the longitudinal direction A. Furthermore, when the second traction member 1052 advances and retracts along the longitudinal direction A, the second slide pin 1521 provided in the second traction member 1052 advances and retracts along the second slide slot 1320. Then, the second movable arm 1032 opens in the open-close direction B around the second rotation pin 1221 as the center. With this configuration, when the second slider 1822 advances and retracts along the second operation portion main body 1821 in the longitudinal direction A, it is possible to drive the second movable arm 1032 to perform the open-close operation in the open-close direction B.

The finger hook portion 1823 is a substantially ring-shaped finger hooking portion formed on the proximal-end side A2 of the second operation portion main body 1821.
[Operations and Effect of Clip Device 1100]

Next, operations and effect of the clip device 1100 will be described with reference from FIG. 37 to FIG. 40. In the present embodiment, as an example of how to use the clip device 1100, a procedure for ligating a wound in body tissue will be described.

FIG. 37 is a view schematically showing a state in which the first movable arm 1031 of the treatment portion 1001 of the clip device 1100 is opened and the treatment portion 1001 is moved to approach the tissue to be grasped. FIG. 38 is a schematic view showing the state of closing the first movable arm 1031 of the treatment portion 1001 of the clip device 1100 to grasp the tissue. FIG. 39 is a schematic view showing the state of opening the second movable arm and moving the treatment portion 1001 to approach the tissue to be grasped while the first movable arm 1031 of the treatment portion 1001 of the clip device 1100 is grasping the tissue.

FIG. 40 is a schematic view showing a state of indwelling the treatment portion 1001 from the clip device 1100 in the state in which the second movable arm 1032 of the treatment portion 1001 of the clip device 1100 is closed and the treatment portion 1001 is grasping the tissue.
[Preparation]

As a preparation operation, a surgeon (not shown) identifies a wound in body tissue by a known method. Specifically, the surgeon inserts an insertion portion of an endoscope (not shown) into a digestive tract such as the esophagus, stomach, duodenum, or large intestine through a Natural orifice of a luminal cavity (for example, the mouth of a patient), and observes an image obtained by an imaging unit of the endoscope to specify a defect T of the tissue D inside the luminal cavity as the treatment target.
(Insertion Step)

The surgeon inserts the clip device 1100 into the channel of the endoscope, and protrudes the clip device 1100 from the distal-end opening of the channel of the endoscope. The surgeon moves the treatment portion 1001 provided on the distal-end side A1 of the clip device 1100 to the vicinity of the defect T.
(Arrangement Step)

As shown in FIG. 37, the surgeon opens and closes the first movable arm 1031 near the first portion Ta of the defect T as the treatment target. More specifically, when the surgeon slides the first slider 1812 in the longitudinal direction A toward the distal-end side A1, the first traction member 1051 moves toward the distal-end side A1. When the first slide pin 1511 connected to the first traction member 1051 advances, the first movable arm 1031 rotates about the first rotation pin 1211 as the center of rotation. The first movable arm 1031 rotates toward the upper side B1 in the open-close direction B such that the first arm portion 1312 on the distal-end side A1 is separated from the fixed arm 1002. As a result, the first movable arm 1031 enters the open state relative to the fixed arm 1002, and it is possible to grasp the first portion Ta of the defect T as the treatment target.

In this state, the surgeon moves the first movable arm 1031 in the open state and the fixed arm 1002 toward the first portion Ta of the defect T that is intended to be grasped, and locate the first portion Ta between the first movable arm 1031 and the fixed arm 1002.
(Grasping Step)

In FIG. 38, when the surgeon can confirm that the first portion Ta of the defect T is positioned between the first movable arm 1031 and the fixed arm 1002, the surgeon pulls the first slider 1812 of the first operation portion 1081 so as to move the first traction member 1051 toward the proximal-end side A2. Therefore, when the first slide pin 1511 connected to the first traction member 1051 retracts, the first arm portion 1312 of the first movable arm 1031 rotates toward the lower side B2 in the open-close direction B toward the fixed arm 1002. As a result, the first movable arm 1031 enters the closed state relative to the fixed arm 1002 and grasps the first portion Ta of the defect T as the treatment target. At this time, the first portion Ta of the defect T is clamped by the first movable arm 1031 and the fixed arm 1002. Also, the piercing portion 1910 protruding toward the lower side B2 from the first grasping surface 1312a is pushed to the upper side B1. The piercing portion 1910 as the leaf spring pushes back to the lower side B2 as the opposite direction B of the upper side B1 where the piercing portion 1910 is pushed in the open-close direction B by the elastic restoring force. Then, the tissue is biased to the lower side B2 by the piercing portion 1910 in addition to the state of being grasped by the fixed arm 1002 and the first movable arm 1031. Accordingly, it is possible for the fixed arm 1002 and the first movable arm 1031 to firmly grasp the tissue.

During the process when the surgeon pulls the first slider 1812 toward the proximal-end side A2, the first engagement portion 1311 formed on the proximal-end side A2 of the first movable arm 1031 also rotates about the first rotation pin 1211 in the open-close direction B. As a result, the first engagement portion 1311 enters the groove portion 1041 formed in the clip holder 1004 and is accommodated inside the clip holder 1004. Accordingly, the first portion Ta of the defect T is grasped by the first movable arm 1031 and the fixed arm 1002. In this state, the state in which the first slider 1812 is pulled toward the proximal-end side A2 is maintained by the surgeon, and the state in which the first portion Ta of the defect T is grasped by the first movable arm 1031 and the fixed arm 1002 is maintained. However, it is possible for the surgeon to operate the operation portion 1008 again so as to rotate the first movable arm 1031 to transition the first movable arm 1031 to the open state relative to the fixed arm 1002 such that it is possible to re-grasp the first portion Ta of the defect T.

(Traction Step)

In FIG. 39, the surgeon maintains the state of grasping the first portion Ta of the defect T by the first movable arm 1031 and the fixed arm 1002 and moves the whole treatment portion 1001 to the vicinity of the second portion Tb of the defect T as the ligation target with the first portion Ta of the defect T. During this process, the surgeon maintains the closed state of the first movable arm 1031 and the fixed arm 1002.

(Arrangement Step)

When the surgeon confirms that the treatment portion 1001 reaches the vicinity of the second portion Tb of the defect T, the surgeon opens and closes the second movable arm 1032 near the second portion Tb of the defect T as the treatment target. More specifically, when the surgeon slides the second slider 1822 toward the distal-end side A1, the second traction member 1052 moves to the distal-end side A1. When the second slide pin 1521 connected to the second traction member 1052 advances, the second movable arm 1032 rotates about the second rotation pin 1221 as the center of rotation. The second movable arm 1032 rotates toward the lower side B2 in the open-close direction B such that the second arm portion 1322 on the distal-end side A1 is separated from the fixed arm 1002. As a result, the second movable arm 1032 is in the open state relative to the fixed arm 1002, and it is possible to grasp the second portion Tb of the defect T as the treatment target.

In this state, the surgeon moves the second movable arm 1032 and the fixed arm 1002, which are in the open state, toward the second portion Tb of the defect T that is intended to be grasped, and locates the second portion Tb of the defect T between the second movable arm 1032 and the fixed arm 1002.

(Grasping Step)

As shown in FIG. 40, when the surgeon can confirm that the second portion Tb of the defect T is positioned between the second movable arm 1032 and the fixed arm 1002, the surgeon pulls the second slider 1822 of the second operation portion 1082 to move the second traction member 1052 to the proximal-end side A2. Therefore, when the second slide pin 1521 connected to the second traction member 1052 retracts, the second arm portion 1322 of the second movable arm 1032 rotates toward the upper side B1 in the open-close direction B toward the fixed arm 1002. As a result, the second movable arm 1032 enters the closed state relative to the fixed arm 1002 so as to grasp the second portion Tb of the defect T as the treatment target. At this time, the second portion Tb of the defect T is clamped by the second movable arm 1032 and the fixed arm 1002. Also, the piercing portion 1920 protruding toward the upper side B1 from the second grasping surface 1322a is pushed to the lower side B2. The piercing portion 1920 as the leaf spring pushes back to the upper side B1 as the opposite direction B of the lower side B2 where the piercing portion 1910 is pushed in the open-close direction B by the elastic restoring force. Then, the tissue is biased to the upper side B1 by the piercing portion 1920 in addition to the state of being grasped by the fixed arm 1002 and the second movable arm 1032. Accordingly, it is possible for the fixed arm 1002 and the second movable arm 1032 to firmly grasp the tissue.

In the process in which the surgeon pulls the second slider 1822 toward the proximal-end side A2, the second engagement portion 1321 formed on the proximal-end side A2 of the second movable arm 1032 also rotates about the second rotation pin 1221 as the center in the open-close direction B. As a result, the second engagement portion 1321 enters the groove portion 1041 formed in the clip holder 1004 and is accommodated inside the clip holder 1004. Accordingly, the second portion Tb of the defect T is grasped by the second movable arm 1032 and the fixed arm 1002. In this state, the state in which the second slider 1822 is pulled toward the proximal-end side A2 is maintained by the surgeon, and the state in which the second portion Tb of the defect T is grasped by the second movable arm 1032 and the fixed arm 1002 is maintained. However, it is possible for the surgeon to operate the operation portion 1008 again so as to rotate the second movable arm 1032 to transition the second movable arm 1032 to the open state relative to the fixed arm 1002 such that it is possible to re-grasp the second portion Tb of the defect T.

Thereafter, when the first slider 1812 of the operation portion 1008 is further retracted toward the proximal-end side A2 in the longitudinal direction A, the clip holder 1004 makes the first engagement portion 1311 of the first movable arm 1031 to be engaged with the inside of the clip holder 1004 so as to lock the first movable arm 1031 to not to open. Also, when the second slider 1822 of the operation portion 1008 is further retracted toward the proximal-end side A2 in the longitudinal direction A, the clip holder 1004 makes the second engagement portion 1321 of the second movable arm 1032 to be engaged with the inside of the clip holder 1004 so as to lock the second movable arm 1032 to not to open.

(Indwelling Step)

By the above-described treatment, the first portion Ta and the second portion Tb of the defect T as the treatment targets are grasped by the treatment portion 1001, as shown in FIG. 40. In this state, the surgeon further pulls the first slider 1812 of the first operation portion 1081 and the second slider 1822 of the second operation portion 1082 toward the proximal-end side A2 to move the first traction member 1051 and the second traction member 1051 to the proximal-end side A2.

In the present embodiment, the first traction member 1051 and the second traction member 1052 are detachably attached to the first slide pin 1511 and the second slide pin 1521, respectively. For example, by the surgeon pulling the first traction member 1051 toward the proximal-end side A2, the notch portion 1512 of the first traction member 1051 is deformed or broken, and the first slide pin 1511 comes out of the first slide pin hole 1510 so as to release the engagement. Also, by pulling the second traction member 1052 toward the proximal-end side A2, the notch portion 1522 of the second traction member 1052 is deformed or broken, and the second slide pin 1521 comes out of the second slide pin hole 1520 and so as to release the engagement. It is noted that that the specific configuration of the engagement between the first traction member 1051 and the first slide pin 1511, and the engagement between the second traction member 1052 and the second slide pin 1521 are not limited to the present embodiment.

When the amount of the force that the surgeon moves the first traction member 1051 and the second traction member 1052 toward the proximal-end side A2 exceeds a predetermined value, as described above, the engagement between the first traction member 1051 and the first slide pin 1511 and the engagement between the second traction member 1052 and the second slide pin 1521 are released. Accordingly, the treatment portion 1001 of the clip device 1100 is indwelled inside the luminal cavity in the state in which the first movable arm 1031 and the fixed arm 1002 grasp the first portion Ta of the defect T and the second movable arm 1032 and the fixed arm 1002 grasp the second portion Tb of the defect T.

The surgeon then operates the operation portion 1008 of the clip device 1100 to remove the sheath 1007 to the outside of the patient's body to complete the treatment for the treatment target.

In the present embodiment, with the above-described configuration, it is possible for the treatment portion 1001 of the clip device 1100 to close the defect T of the tissue D as the treatment target.

Also, in the present embodiment, the first movable arm 1031 and the second movable arm 1032 have the piercing portion 1910 and the piercing portion 1920 respectively such that it is possible to hook the tissue at the time of grasping the defect T of the tissue. Accordingly, it is possible for the treatment portion 1001 to make the tissue that is grasped by the fixed arm 1002 and the movable arm 1003 to be difficult to slip off.

Also, in the present embodiment, the piercing portion 1910 and the piercing portion 1920 are elastically deformable leaf springs. Accordingly, it is possible to make the tissue that is grasped by the fixed arm 1002 and the movable arm 1003 to be biased to the grasping direction of each movable arm 1003 while grasping the tissue without damaging or tearing the tissue.

Also, in the present embodiment, the piercing portion 1910 and the piercing portion 1920 are formed by punching and bending the movable arm 1003. According to this configuration, it is possible to reduce the number of manufacturing members of the clip device 1100 and make the manufacturing process to be easy. Also, the number of members used during the manufacturing is reduced such that the cost spent on the members can be reduced.

Also, in the present embodiment, the clip device 1100 includes multiple piercing portions 1910 and piercing portions 1920. Accordingly, it is possible for the clip device 1100 to further prevent the tissue from slipping off.

As described above, the third embodiment of the present disclosure has been described in detail with reference to the drawings; however, the specific configuration is not limited to the present embodiment, and design changes and the like are included within the scope of the present disclosure. The clip device described in the present embodiment may be appropriately combined with the configuration according to each embodiment of the present disclosure. Also, the configurational elements shown in the above-described embodiment and each embodiment shown below can be combined as appropriate.

Fourth Embodiment

Next, a fourth embodiment of the present disclosure will be described with reference to FIG. 41 to FIG. 46. In the following description, the same reference signs are given to the same configurations as those already described, and redundant descriptions will be omitted. Each of the following embodiments differs from the third embodiment in the movable arm. Therefore, in the following description, the differences from the third embodiment will be mainly described. FIG. 41 is a view showing a state in which a treatment portion (clip) 1001A of a clip device 1100A according to the fourth embodiment of the present disclosure is closed. FIG. 42 is an enlarged view showing the distal-end side A1 of the treatment portion 1001A of the clip device 1100A. FIG. 43 is a schematic view showing a state of opening a first movable arm 1031A of the treatment portion 1001A of the clip device 1100A to make the treatment portion 1001A to approach the tissue to be grasped. FIG. 44 is a schematic view showing a state of closing the first movable arm 1031A of the treatment portion 1001A of the clip device 1100A and grasping the tissue. FIG. 45 is a schematic view showing a state of opening the second movable arm 1032A and making the treatment portion 1001A to approach the tissue to be grasped while the first movable arm 1031A of the treatment portion 1001A of the clip device 1100A is grasping the tissue. FIG. 46 is a schematic view showing a state of closing the second movable arm 1032A of the treatment portion 1001A of the clip device 1100A to indwell the treatment portion 1001A from the clip device 1100A in a state in which the treatment portion 1001A is grasping the tissue.

The clip device 1100A according to a fourth embodiment of the present disclosure includes the treatment portion (clip) 1001A and the applicator 1200. Here, the applicator 1200 is same with that according to the third embodiment such that the description and drawings are omitted.

As shown in FIG. 41, the treatment portion 1001A includes the fixed arm 1002, the movable arm 1003A, and the clip holder 1004. The fixed arm 1002 and the clip holder 1004 are the same with that according to the third embodiment such that the description and drawings are omitted.

As shown in FIG. 41, the movable arm 1003A includes a first movable arm 1031A that opens and closes in the upper side (first direction) in the open-close direction B relative to the fixed arm 1002 and a second movable arm 1032A that opens and closes in the lower side (second direction) in the open-close direction B relative to the fixed arm 1002. The first movable arm 1031A and the second movable arm 1032A are independently operable to open and close.

The first movable arm 1031A includes the first slide slot 1310, the first engagement portion 1311, the first through hole 1313, and a first arm portion 1312A. The first slide slot 1310, the first engagement portion 1311, and the first through hole 1313, are the same with that according to the third embodiment such that the description is omitted.

As shown in FIG. 41 or FIG. 42, the first arm portion 1312A is formed in a substantial cup shape and formed of the resin or metal. The first arm portion 1312A is able to clamp the living tissue by rotating in the open-close direction B relative to the fixed arm 1002. The first arm portion 1312A includes a first grasping surface 1312aa, the first outer surface 1312b, the first arm-claw portion (first arm-claw) 1317, and a first piercing portion (anchor, first arm-spike) 1910A. The first outer surface 1312b is the same with that according to the third embodiment such that the description is omitted. Also, in the present embodiment, the first grasping surface 1312aa has the same configuration with the first grasping surface 1312a except for that the opening portion 1314 included in the first grasping surface 1312a is not provided when compared with the third embodiment.

As shown in FIG. 41 or FIG. 42, the first arm-claw portion 1317 is provided on the distal-end side A1 of the first arm portion 1312A. The first arm-claw portion 1317 is bent to the lower side B2 in the open-close direction B to be a distal end of the first arm portion 1312A. The first arm-claw portion 1317 is provided on the distal-end side A1 of the distal-end portion 1002a of the fixed arm 1002 in the longitudinal direction A. The first arm-claw portion 1317 includes the opposite surface 1317a being opposite to the distal-end portion 1002a of the fixed arm 1002.

The first piercing portion (anchor) 1910A extends along the longitudinal direction A. The first piercing portion (anchor) 1910A is formed by using the elastically deformable material, for example. The first piercing portion 1910A includes a first connection portion 1910Aa on the distal-end side A1. Also, the first piercing portion 1910A includes a first protruding end portion 1910Ab on the proximal-end side A2 of the first connection portion 1910Aa as the distal end of the first piercing portion 1910A.

The first connection portion 1910Aa is connected to the opposite surface 1317a of the first arm-claw portion 1317. The first piercing portion 1910A faces the proximal-end side A2 of the longitudinal direction A and extends toward the distal-end portion 1002a of the fixed arm 1002. Also, a width of the first protruding end portion 1910Ab in the thickness direction C is smaller than the width of the first connection portion 1910Aa. Accordingly, the first piercing portion 1910A is formed in a substantially conical shape, for example. It is noted that the shape of the first piercing portion 1910A is not particularly limited.

The second movable arm 1032A includes the second slide slot 1320, the second engagement portion 1321, the second through hole 1323, and a second arm portion 1322A. The second slide slot 1320, the second engagement portion 1321, and the second through hole 1323 are the same with that according to the third embodiment such that the description thereof is omitted.

The second arm portion 1322A, as shown in FIG. 41 or FIG. 42, is formed in a substantial cup shape and formed from the resin or metal, for example. The second arm portion 1322A is able to clamp the living tissue by rotating in the open-close direction B relative to the fixed arm 1002. The second arm portion 1322A includes a second grasping surface 1322a, the second outer surface 1322b, the second arm-claw portion (second arm-claw) 1327, and a second piercing portion (anchor, second fixed-arm spike) 1920A. The second outer surface 1322b is the same with that according to the third embodiment such that the description is omitted. Also, in the present embodiment, the second grasping surface 1322a has the same configuration with the second grasping surface 1322a except for that the opening portion 1324 included in the second grasping surface 1322a is not provided when compared with the third embodiment.

As shown in FIG. 41 or FIG. 42, the second arm-claw portion 1327 is provided on the distal-end side A1 of the second arm portion 1322A. The second arm-claw portion 1327 is bent to the upper side B1 in the open-close direction B to be a distal end of the second arm portion 1322A. The second arm-claw portion 1327 is provided on the distal-end side A1 of the distal-end portion 1002a of the fixed arm 1002 in the longitudinal direction A. The second arm-claw portion 1327 includes the opposite surface 1327a being opposite to the distal-end portion 1002a of the fixed arm 1002.

As shown in FIG. 41 or FIG. 42, the second piercing portion (anchor) 1920A extends along the longitudinal direction A. The second piercing portion (anchor) 1920A is formed by using the elastically deformable material, for example. The second piercing portion 1920A includes a second connection portion 1920Aa on the distal-end side A1. Also, the second piercing portion 1920A includes a second protruding end portion 1920Ab on the proximal-end side A2 of the second connection portion 1920Aa as the distal end of the second piercing portion 1920A.

The second connection portion 1920Aa is connected to the opposite surface 1327a of the second arm-claw portion 1327. The second piercing portion 1920A faces the proximal-end side A2 of the longitudinal direction A and extends toward the distal-end portion 1002a of the fixed arm 1002. Also, a width of the second protruding end portion 1920Ab in the thickness direction C is smaller than the width of the second connection portion 1920Aa. Accordingly, the second piercing portion 1920A is formed in a substantially conical shape, for example. It is noted that the shape of the second piercing portion 1920A is not particularly limited.

A spatial portion S1 is formed between the first protruding end portion 1910Ab and the second protruding end portion 1920Ab with the distal-end portion 1002a of the fixed arm 1002.

According to the present embodiment, the operations and effects disclosed from FIG. 43 to FIG. 46 are the same with the operations and effects of the clip device according to the third embodiment that are described using FIG. 37 to FIG. 40 such that the description of the operations and effects is omitted.

Similar to the above-described third embodiment, the first movable arm 1031A and the second movable arm 1032A according to the present embodiment include the first piercing portion 1910A and the second piercing portion 1920A respectively so as to be able to hook on the tissue at the time of grasping the defect T of the tissue. Accordingly, the treatment portion 1001 is able to make the tissue that is grasped by the fixed arm 1002 and the movable arm 1003 to be difficult to slip off.

Also, in the present embodiment, the space S1 is formed between the first protruding end portion 1910Ab, the second protruding end portion 1920Ab and the distal-end portion 1002a of the fixed arm 1002. Accordingly, it is easy for the clip device 1100A to grasp the tissue since the tissue enters the spatial portion S1 at the time of grasping the defect T of the tissue by the fixed arm 1002 and the movable arm 1003.

As described above, the fourth embodiment of the present disclosure has been described in detail with reference to the drawings; however, the specific configuration is not limited to the present embodiment, and design changes and the like are included within the scope of the present disclosure. Also, the configurational elements shown in the above-described embodiment and each embodiment shown below can be combined as appropriate.

Fifth Embodiment

Next, a fifth embodiment of the present disclosure will be described with reference to FIG. 47 and FIG. 48. In the following description, the same reference signs are given to the same configurations as those already described, and redundant descriptions will be omitted. The configuration according to the following embodiment is different in the fixed arm and the movable arm when compared with the fourth embodiment. Accordingly, in the following description, the different points with the fourth embodiment will be focused to be described. FIG. 47 is a view showing a state in which a treatment portion 1001B of a clip device 1100B according to the fifth embodiment of the present disclosure is closed. FIG. 48 is an enlarged view showing the distal-end side A1 of the treatment portion 1001B of the clip device 1100B.

The clip device 1100B according to the fifth embodiment of the present disclosure includes the treatment portion (clip) 1001B and the applicator 1200. Here, the applicator 1200 is the same with that according to the third embodiment and the fourth embodiment such that the description and drawings are omitted.

As shown in FIG. 47, the treatment portion 1001A includes a fixed arm 1002B, a movable arm 1003B, and the clip holder 1004. The clip holder 1004 is the same with that according to the third embodiment and the fourth embodiment such that the description is omitted. Also, when compared with the fourth embodiment, the movable arm 1003B has the same configuration with that according to the fourth embodiment except for that the first piercing portion 1910A of the first movable arm 1031A and the second piercing portion 1920A of the second movable arm 1032A are not provided such that the description of the movable arm 1003B is omitted.

As shown in FIG. 47 and FIG. 48, the fixed arm 1002B includes a piercing portion (spike) 1900B in addition to the configuration of the fixed arm 1002 according to the third embodiment and the fourth embodiment. Also, the fixed arm 1002B includes an opposite surface 1002p in the distal-end portion 1002a when compared with the fixed arm 1002 according to the third embodiment and the fourth embodiment.

The opposite surface 1002p is formed in a substantial disk shape following the distal-end portion 1002a, and a radial dimension thereof is larger than a radial dimension of the rod-shaped portion 1002b. Also, the opposite surface 1002p is opposite to the first arm-claw portion 1317 and the second arm-claw portion 1327.

The piercing portion 1900B is provided on the distal-end side A1 of the fixed arm 1002B. The piercing portion 1900B includes a first fixed-arm piercing portion 1901B and a second fixed-arm piercing portion 1902B. The first fixed-arm piercing portion 1901B and the second fixed-arm piercing portion 1902B are arrayed along the open-close direction in the opposite surface 1002p as shown in FIG. 48.

As shown in FIG. 47 and FIG. 48, the first fixed-arm piercing portion 1901B extends along the longitudinal direction A. The first fixed-arm piercing portion 1901B is formed by using the elastically deformable material, for example. Also, the first fixed-arm piercing portion 1901B includes a first connection portion 1901Ba on the proximal-end side A2. Also, the first fixed-arm piercing portion 1901B includes a first protruding end portion 1901Bb that is on the distal-end side A1 of the first connection portion 1901Ba as the distal end of the first fixed-arm piercing portion 1901B.

The first connection portion 1901Ba is connected to the opposite surface 2p of the fixed arm 1002. The first fixed-arm piercing portion 1901B faces the distal-end side A1 in the longitudinal direction A and extends toward the opposite surface 1317a of the first arm-claw portion 1317. Also, a width of the first protruding end portion 1901Bb in the width direction C is smaller than the width of the first connection portion 1901Ba. Accordingly, the first fixed-arm piercing portion 1901B is formed in a substantially conical shape, for example. It is noted that the shape of the first fixed-arm piercing portion 1901B is not particularly limited.

As shown in FIG. 47 and FIG. 48, the second fixed-arm piercing portion 1902B extends along the longitudinal direction A, and in the open-close direction B, the second fixed-arm piercing portion 1902B is provided at the lower side B2 of the first fixed-arm piercing portion 1901B. The second fixed-arm piercing portion 1902B is formed by using the elastically deformable material, for example. The second fixed-arm piercing portion 1902B includes a second connection portion 1902Ba on the proximal-end side A2. Also, the second fixed-arm piercing portion 1902B includes a second protruding end portion 1902Bb that is on the distal-end side A1 of the second connection portion 1902Ba as the distal end of the second fixed-arm piercing portion 1902B.

The second connection portion 1902Ba is connected to the opposite surface 1002p of the fixed arm 1002. The second fixed-arm piercing portion 1902B faces the distal-end side A1 in the longitudinal direction A and extends toward the opposite surface 1327a of the second arm-claw portion 1327. Also, a width of the second protruding end portion 1902Bb in the width direction C is smaller than the width of the second connection portion 1902Ba. Accordingly, the second fixed-arm piercing portion 1902B is formed in a substantially conical shape, for example. It is noted that the shape of the second fixed-arm piercing portion 1902B is not particularly limited.

A spatial portion S2 is formed between the first protruding end portion 1901Bb, the second protruding end portion 1902Bb and the opposite surface 1317a of the first arm-claw portion 1317, the opposite surface 1327a of the second arm-claw portion 1327.

The operations and effects of the clip device 1100B according to the present embodiment are the same with that according to the third embodiment and the fourth embodiment such that the description of the operations and effects is omitted.

According to the present embodiment, the fixed arm 1002B includes the first fixed-arm piercing portion 1901B and the second fixed-arm piercing portion 1902B so as to be able to hook on the tissue at the time of grasping the defect T of the tissue. Accordingly, the treatment portion 1001B is able to make the tissue that is grasped by the fixed arm 1002B and the movable arm 1003B to be difficult to slip off.

Also, in the present embodiment, the space S2 is formed between the first protruding end portion 1901Bb, the second protruding end portion 1902Bb and the opposite surface 1317a of the first arm-claw portion 1317, the opposite surface 1327a of the second arm-claw portion 1327. Accordingly, it is easy for the clip device 1100B to grasp the tissue since the tissue enters the spatial portion S2 at the time of grasping the defect T of the tissue by the fixed arm 1002B and the movable arm 1003B.

As described above, the fifth embodiment of the present disclosure has been described in detail with reference to the drawings; however, the specific configuration is not limited to the present embodiment, and design changes and the like are included within the scope of the present disclosure. Also, the configurational elements shown in the above-described embodiment and modification example shown below can be combined as appropriate.

(Modification Example)

The clip device 1100 according to the above-described third embodiment includes the piercing portion 1910 and the piercing portion 1920; however, it is not necessary for the clip device 1100 to have both of them. The clip device 1100 may include either of the piercing portion 1910 or the piercing portion 1920. Also, the piercing portion 1910 and the piercing portion 1920 may be included only in the distal ends of the first arm portion 1312 and the second arm portion 1322. In this case, the piercing portion 1910 and the piercing portion 1920 abut on the root portion of the tissue (the portion that is not fragile) such that it is possible to prevent the tissue from being teared from the piercing portion 1910 and the piercing portion 1920 as the beginning points.

Also, the shape of the piercing portion 1910 according to the third embodiment is not particularly limited. For example, as shown in FIG. 49, the piercing portion 1910 may be formed in a tapered shape toward the proximal-end side A2. Also, this configuration may be the piercing portion 1920. In this case, the opening portion 1314 that opens in the first arm portion 1312 may have the same shape; however, it is not particularly limited.

The lengths of the first piercing portion 1911 and the second piercing portion 1912 in the longitudinal direction A included in the piercing portion 1910 according to the third embodiment are not particularly limited. For example, the length of the second piercing portion 1912 in the longitudinal direction A may be longer than that of the first piercing portion 1911. In this case, the second piercing portion 1912 enters the root portion of the tissue (the portion that is not fragile) so as to prevent the tissue from slipping off. Also, in the above-described modification example, the first piercing portion 1911 and the second piercing portion 1912 of the first movable arm 1031 are described; however, the configuration may be applied to the second movable arm 1032.

Also, as shown in FIG. 50 and FIG. 51, the piercing portion 1910 and the piercing portion 1920 may be provided in the edge of the movable arm 1003. For example, the first grasping surface 1312a of the first movable arm 1031 may further include the edge portion 1312c. The piercing portion 1910C may be provided in the edge portion 1312c. Similarly, the second grasping surface 1322a of the second movable arm 1032 may further include the edge portion 1322c. The piercing portion 1920C may be provided in the edge portion 1322c. In this case, for example, the tissue is accommodated in the first arm portion 1312 and the recess portion formed in the first arm portion 1312. The treatment portion 1001 of the clip device 1100 can grasp the tissue while preventing the tissue from slipping off from the first arm portion 1312 and the second arm portion 1322 by the piercing portion 1910 provided in the edge portion 1312c or the piercing portion 1920C provided in the edge portion 1322c. Also, as shown in FIG. 51, the piercing portion 1910C and the piercing portion 1920C may be alternatively provided in the longitudinal direction in the state in which the first movable arm 1031 and the second movable arm 1032 are closed relative to the fixed arm 1002. In this case, the piercing portion 1910C and the second piercing portion 1920C can further enter the tissue deeply and the clip device 1100 can grasp the tissue while preventing the tissue from slipping off from the treatment portion 1001.

As shown in FIG. 52 and FIG. 53, the piercing portion according to the present disclosure may be provided on the contact surface 1002c of the fixed arm 1002 that is contactable with the tissue rather than the first arm portion 1312 and the second arm portion 1322. As shown in FIG. 52, the piercing portion 1900D faces the first movable arm 1031 and the second movable arm 1032 provided on both sides in the open-close direction B relative to the fixed arm 1002. The piercing portion 1900D is formed in the tapered shape as toward the proximal-end side A2. Even in this case, the treatment portion of the clip device can make the tissue that is grasped by the first movable arm 1031, the second movable arm 1032 and the fixed arm 1002 to be difficult to slip off at the time of grasping the defect of the tissue. Also, at least one or more than one piercing portion 900D has to be provided, and the number of the piercing portions is not particularly limited.

Also, as shown in FIG. 53, the plurality of piercing portions provided in the fixed arm 1002 may be formed such that the dimension of the piercing portion 1900D on the distal-end side A1 is larger than the dimension of the piercing portion 1900D on the proximal-end side A2. Even in this case, at the time of grasping the defect of the tissue, the piercing portion 1900D on the distal-end side A1 enters the root portion of the tissue such that it is difficult for the tissue to slip off.

Also, the piercing portion 1910 and the piercing portion 1920 may be applied to the case in which the fixed arm 1002 includes the plate-shaped first fixed arm including the first contact surface being opposite to the first movable arm 1031 and contact with the tissue and the plate-shaped second fixed arm including the second contact surface being opposite to the second movable arm 1032 and contact with the tissue. In this case, the first fixed arm and the second fixed arm are plate-shaped such that it is possible to form the opening portion by processing from the first contact surface side and the second contact surface side by the stamping processing and the drilling processing or the like. Furthermore, the piercing portion 1910 and the piercing portion 1910 may be formed by bending part of the first fixed arm and the second fixed arm from the edge of the opening portion. Accordingly, it is possible to reduce the number of the member during the manufacturing so as to make the manufacturing process easy.

Also, the piercing portion according to the present disclosure may be provided in both of the movable arm 1003 and the fixed arm 1002, or be provided in either of the movable arm 1003 or the fixed arm 1002.

In either of the above-described embodiment, according to the clip and the clip device according to the present disclosure, it is possible to prevent the tissue from slipping off from the arm and definitely grasp the tissue.

Sixth Embodiment

A clip device (endoscopic treatment device) 2100 according to a sixth embodiment of the present disclosure will be described with reference to FIG. 54 to FIG. 65. FIG. 54 is a view showing the overall configuration of the clip device (endoscopic treatment device) 2100 according to the sixth embodiment of the present disclosure.

Here, in the embodiments and modification examples described below, the same reference signs are given to mutually corresponding configurations, and descriptions of redundant features may be omitted. Also, in the following description, recitations indicating the relative or absolute arrangements such as "parallel", "orthogonal", "center", "coaxial" or the like do not only express such arrangements strictly, but also express a state of relative displacement at an angle or distance that provides the same function. Furthermore, the recitation of "patient" as used herein includes any organism and includes the recitation "tester". The patient may be a human or an animal.

[Clip Device (Endoscopic Treatment Device) 100]

FIG. 54 is a view showing the overall configuration of the clip device (endoscopic treatment device) 2100. The clip device 2100 includes a treatment portion (clip) 2001 and an applicator 2200. The applicator 2200 also includes a traction member 2005 (see FIG. 61), an operation wire (wire) 2006 (see FIG. 61), a sheath 2007, and an operation portion 2008. In the following description, the treatment portion 2001 side in the longitudinal direction A of the clip device 2100 is defined as a tip side (distal-end side) A1 of the clip device 2100, and the operation portion 2008 side of the applicator

2200 of the clip device 2100 is defined as base side (proximal-end side) A2 of the clip device 2100. In the clip device 2100, the treatment portion 2001, the traction member 2005 of the applicator 2200, the operation wire 2006, the sheath 2007 and the operation portion 2008 are arranged in this sequence from the distal-end side A1 to the proximal-end side A2 of the clip device 2100.

The clip device 2100 is used, for example, together with an endoscope (not shown). More specifically, the clip device 2100 is configured such that it is possible to introduce the treatment portion 2001 to the vicinity of the living tissue in the luminal cavity as a treatment object to perform the treatment relative to the living tissue by the surgeon operating the operation portion 2008 of the applicator 2200 to insert the sheath 2007 and the treatment portion 2001 provided at the distal-end side A1 of the sheath 2007 into a treatment device channel formed in the endoscope. In the present embodiment, the endoscope used with the clip device 2100 may be any flexible endoscope.

(Treatment Portion (Clip) 1)

FIG. 55 is a view showing a state in which the treatment portion 2001 of the clip device 2100 is closed. The treatment portion (clip) 2001 is used as a useful clip for patient therapeutic procedures such as performing hemostasis of tissues, closing perforations and hemostasis, suture contraction of internal wounds, marking lesions and tractions (mucosal protuberance), and other surgical procedures. The treatment portion 2001 is detached from the applicator 2200 by the operation of the surgeon and indwelled in the luminal cavity. The treatment portion 2001 includes a fixed arm 2002, a movable arm 2003, and a clip holder 2004, as shown in FIG. 55. Here, the movable arm 2003 has a first movable arm 2031 and a second movable arm 2032 that open and close relative to the fixed arm 2002. The first movable arm 2031 and the second movable arm 2032 are provided on both sides of the fixed arm 2002 and are arms that open independently in opposite directions.

A direction in which the movable arm 2003 of the treatment portion 2001 opens and closes relative to the fixed arm 2002 is defined as an open-close direction B or an up-down direction B, and a direction in which the first movable arm 2031 opens to be separated away from the fixed arm 2002 is defined as an upper side B1. Also, a direction in which the second movable arm 2032 opens to be separated away from the fixed arm 2002 is defined as a lower side B2. A direction orthogonal to the longitudinal direction A and the open-close direction B is defined as a thickness direction C or a left-right direction C.

[Fixed Arm 2002]

FIG. 60 is a view showing the fixed arm 2002 of the treatment portion 2001 of the clip device 2100. The fixed arm 2002 is a rod-shaped member provided between the movable arms 2003 along the longitudinal direction A, as shown in FIG. 55 and FIG. 60. The fixed arm 2002 has a rod portion 2020A formed on the distal-end side A1 and a connection portion 2020B formed on the proximal-end side A2.

The rod portion 2020A is, for example, a substantially round rod-shaped member made of a material having biocompatibility, as shown in FIG. 60. The rod portion 2020A is exposed on its entire outer surface and is capable of being in contact with the tissue. The rod portion 2020A includes a distal-end portion 2002a and a rod-shaped portion 2002b.

The distal-end portion 2002a is provided at the distal end the rod-shaped portion 2002b. The distal-end portion 2002a is formed in a substantially disc shape having a diameter larger than that of the rod-shaped portion 2002b. Therefore, the fixed arm 2002 can be locked to the living tissue by hooking the distal-end portion 2002a of the fixed arm 2002 to the living tissue.

The rod-shaped portion 2002b is a substantially round rod-shaped member, and has the distal-end portion 2002a at its distal end. The rod-shaped portion 2002b includes a rod distal-end portion 2002c, a rod central portion 2002d, a rod proximal-end portion 2002e, a first opposite surface 2025, a second opposite surface 2026, and a plurality of protrusion portions 2027.

The rod distal-end portion (second region) 2002c is a part of the rod-shaped portion 2002b and is provided on the distal-end side A1 of the rod-shaped portion 2002b. The rod distal-end portion 2002c is formed using a metal material (second material) having a higher elastic modulus than that of the rod central portion 2002d. The titanium such as 64 titanium alloy (Ti-6AL-4V) and the stainless steel such as SUS301, SUS304-CSP, SUS316 and the like may be used as the metal material of the rod distal-end portion 2002c.

The rod middle portion (first region) 2002d is a part of the rod-shaped portion 2002b, and is provided at the center of the rod-shaped portion 2002b in the longitudinal direction A. The rod central portion 2002d is provided on the proximal-end side A2 of the rod distal-end portion 2002c. The rod central portion 2002d has the elastic modulus lower than that of the rod distal-end portion 2002c to be bent and deformable. The rod central portion 2002d is bent to a direction where the load is applied when the grasped tissue applies the load to the fixed arm 2002, for example. Subsequently, the bending rod central portion 2002d may have the elasticity with a degree to firmly grasp the tissue without tearing or damaging the tissue due to a repulsive force in the direction opposite to the direction in which the load is applied. The rod central portion 2002d may be a leaf spring or the like. The rod central portion 2002d may be formed with the metal material (first material) having the elasticity to be bent and deformable. As the metal material of the bending rod central portion 2002d, for example, a cobalt-chromium alloy (for example, the Spron), a cobalt-chromium-iron alloy (for example, the Elgiloy alloy), the stainless steel such as SUS304-CSP, and the like may be used.

The rod proximal-end portion (second region) 2002e is a part of the rod-shaped portion 2002b and is provided on the proximal-end side A2 of the rod-shaped portion 2002b. The rod proximal-end portion 2002e is provided on the proximal-end side A2 of the rod distal-end portion 2002c and the rod central portion 2002d. The elastic modulus of the rod proximal-end portion 2002e is substantially the same with that of the rod distal-end portion 2002c and higher than the elastic modulus of the rod central portion 2002d. Similar to the rod distal-end portion 2002c, the rod proximal-end portion 2002e may be formed using the titanium such as 64 titanium alloy (Ti-6AL-4V) and the stainless steel such as SUS301, SUS304-CSP, SUS316 and the like as the metal material (second material), for example.

The proximal-end portion of the rod distal-end portion 2002c on the proximal-end side A2 is connected and bonded with the distal-end portion of the rod central portion 2002d on the distal-end side A1. The proximal-end portion of the rod central portion 2002d on the proximal-end side A2 is connected and bonded with the distal-end portion of the rod proximal-end portion 2002e on the distal-end side A1. In the present embodiment, the rod-shaped portion 2002b is formed by integrating respective connection portions of the rod distal-end portion 2002c, the rod central portion 2002d, and the rod proximal-end portion 2002e by the metal bonding. Also, the connection portions of the rod distal-end portion 2002c, the rod central portion 2002d, and the rod proximal-end portion 2002e are stacked in the thickness direction C or the open-close direction R to be further firmly bonded with each other due to the metal bonding. Accordingly, the peeling rarely occurs in the connection portions. The sequence of stacking the connection portions is not particularly limited. Also, the end surfaces of the connection portions of the rod distal-end portion 2002c, the rod central portion 2002d, and the rod proximal-end portion 2002e may be formed in an inclined surface shape. With this configuration, the stress acting on the connection portions is suitably dispersed so as to make the stress difficult to concentrate on a specific portion. Therefore, even if the rod distal-end portion 2002c, the rod central portion 2002d, and the rod proximal-end portion 2002e are made of different metal materials, it is possible for the surgeon to use the clip device 2100 without worrying about the peeling of the connection portion.

Here, the material of the rod distal-end portion 2002c, the rod central portion 2002d, and the rod proximal-end portion 2002e is not particularly limited. The rod distal-end portion 2002c, the rod central portion 2002d, and the rod proximal-end portion 2002e may be formed from the metal material or the like besides the metal. For example, the resin having high rigidity, the thermoplastic or serializable resin with suitable elasticity such as the resin materials include polyphthalamide (PPA), polyamide (PA), polyetheretherketone (PEEK), LCP (liquid crystalline polymer), acrylonitrile butadiene styrene (ABS), polyphenylene sulfide (PPS), and the like may be used. Also, the connection portions of the rod distal-end portion 2002c, the rod central portion 2002d, and the rod proximal-end portion 2002e are not limited to the metal bonding. For example, in a case in which the connection portions of the rod distal-end portion 2002c, the rod central portion 2002d and the rod proximal-end portion 2002e are made of the same kind of material such as the metal, they may be integrally formed by welding of spotting, laser, resistance and the like, brazing, caulking, or the like. In a case in which the connection portions of the rod distal-end portion 2002c, the rod central portion 2002d and the rod proximal-end portion 2002e are made of different materials such as the metal, the resin and the like, they may be integrally formed by welding using heat, ultrasonic waves, laser, high frequency or the like, insert molding, or the like.

The first opposite surface 2025 is formed on the rod-shaped portion 2002b and faces the first movable arm 2031 provided on the upper side B1 in the open-close direction B.

The second opposite surface 2026 is formed on the rod-shaped portion 2002b and faces the second movable arm 2032 provided on the lower side B2 in the open-close direction B.

The plurality of protrusion portions 27 are protrusion portions provided on the fixed arm 2002, as shown in FIG. 60. The protrusion portion 2027 includes a first protrusion portion 2027a provided on the first opposite surface 2025 and a second protrusion portion 2027b provided on the second opposite surface 2026. The first protrusion portion 2027a protrudes from the first opposite surface 2025 toward the first movable arm 2031 arranged on the upper side B1 in the open-close direction B. The second protrusion 2027b protrudes from the second opposite surface 2026 toward the second movable arm 2032 arranged on the lower side B2 in the open-close direction B.

The connection portion 2020B is provided on the proximal-end side A2 of the rod portion 2020A. The connection portion 2020B is formed in a plate shape, and the plate thickness direction of the connection portion 2020B substantially coincides with the thickness direction C. Here, in the thickness direction C, one side of the connection portion 2020B is defined as a left side C1. Also, in the thickness direction C, the direction opposite to the left side C1 on one side of the connection portion 2020B is defined as a right side C2. The connection portion 2020B connects the fixed arm 2002 and the movable arm 2003 with the clip holder 2004 and the traction member 2005, which will be described later. The connection portion 2020B includes a through hole 2021, a through hole 2022, an engagement groove 2023, and a tail 2024, as shown in FIG. 60.

The through hole 2021 is a hole penetrating through the connection portion 2020B in the thickness direction C. The through hole 2021 is formed on the distal-end side A1 of the connection portion 2020B. A first rotation pin 2211 is engaged with the through hole 2021 from the left side C1.

The through hole 2022 is a hole penetrating through the connection portion 2020B in the thickness direction C. The through hole 2022 is formed on the distal-end side A1 of the connection portion 2020B. The through hole 2022 is provided at substantially the same position as that of the through hole 2021 in the longitudinal direction A. A second rotation pin 2221 is engaged with the through hole 2022 from the right side C2.

The engagement groove 2023 is a groove extending along the longitudinal direction A formed in the connection portion 2020B. The engagement groove 2023 is a groove penetrating the connection portion 2020B in the thickness direction C.

The tail 2024 is formed on the proximal-end side A2 of the connection portion 2020B of the fixed arm 2002. The tail 2024 is connected to the clip holder 2004 which will be described later.

[Movable Arm 2003]

FIG. 56 is a view showing a state in which the first movable arm 2031 of the treatment portion 2001 of the clip device 2100 is opened when viewed from the left side C1 in the thickness direction C. FIG. 57 is a view showing a state in which the second movable arm 2032 of the treatment portion 2001 of the clip device 2100 is opened when viewed from the right side C2 in the thickness direction C. FIG. 58 is a view showing the first movable arm 2031 of the treatment portion 2001 of the clip device 2100. FIG. 59 is a view showing the second movable arm 2032 of the treatment portion 2001 of the clip device 2100. The movable arm 2003 has the first movable arm 2031 and the second movable arm 2032, as shown in FIG. 55 to FIG. 59. The first movable arm 2031 is arranged on the upper side B1 of the fixed arm 2002 in the open-close direction B. The second movable arm 2032 is arranged on the lower side B2 of the fixed arm 2002 in the open-close direction B. The first movable arm 2031 and the second movable arm 2032 can be opened and closed independently.

As shown in FIG. 55, FIG. 56 and FIG. 58, the first movable arm 2031 is provided so as to be able to open and close relative the upper side B1 in the open-close direction B relative to the distal-end side A1 of the fixed arm 2002. Specifically, the first movable arm 2031 is rotatably attached to the fixed arm 2002 by a first rotation pin 2211 provided in the first through hole 2313. The first movable arm 2031 has a first slide slot 2310, a first engagement portion 2311, a first through hole 2313 and a first arm portion 2312.

The first slide slot 2310 is provided on the proximal-end side A2 of the first movable arm 2031, as shown in FIG. 58.

The first slide slot 2310 engages with a first slide pin 2511, which will be described later.

The first engagement portion 2311 is an elastic member having elasticity in the open-close direction B provided on the proximal-end side A2 of the first movable arm 2031. The first engagement portion 2311 is, for example, a leaf spring. The first engagement portion 2311 is accommodated inside the clip holder 2004 when the first movable arm 2031 is closed relative to the fixed arm 2002. Specifically, as shown in FIG. 56, in a state of opening the first movable arm 2031 relative to the fixed arm 2002, the first engagement portion 2311 is positioned outside the clip holder 2004, which will be described later. On the other hand, as shown in FIG. 55, the first engagement portion 2311 is accommodated inside the clip holder 2004 in a state of closing the first movable arm 2031 relative to the fixed arm 2002. In the state in which the first movable arm 2031 is closed relative to the fixed arm 2002, a length L1 of the first engagement portion 2311 in the open-close direction B is substantially equal to or slightly larger than the inner diameter of the clip holder 2004.

In the present embodiment, when the first movable arm 2031 transitions from the closed state to the open state relative to the fixed arm 2002 in the open-close direction B, the first engagement portion 2311 rotates together with the first movable arm 2031, and the most proximal end of the first engagement portion 2311 enters the inside of the clip holder 2004. During the process of the first engagement portion 2311 entering the inside of the clip holder 2004, each portion of the first engagement portion 2311 that contacts the clip holder 2004 may be rounded or processed such as chamfering so as not to damage the inner circumferential surface of the clip holder 2004.

The first through hole 2313 is a hole penetrating through the first movable arm 2031 in the thickness direction C. The first through hole 2313 is arranged on the left side C1 of the through hole 2021 provided in the fixed arm 2002 in the thickness direction C and engages with the first rotation pin 2211. The first rotation pin 2211 connects the first through hole 2313 and the through hole 2021. With this configuration, the first movable arm 2031 can rotate about the first through hole 2313 as a rotation center relative to the fixed arm 2002.

As shown in FIG. 58, the first arm portion 2312 is formed in a substantially cup shape by slightly bending a plate-shaped member of the resin or metal for example. Here, the plate thickness direction of the first arm portion 2312 is substantially the same with the open-close direction B. By rotating the first arm portion 2312 along the open-close direction B relative to the fixed arm 2002, the distal-end portion thereof approaches the distal-end portion 2002a of the fixed arm 2002 and can sandwich the living tissue. For example, the distal-end portion of the first arm portion 2312 may be formed with a distal end in a claw shape for definitely clamping the living tissue. However, the first arm portion 2312 is not limited to the shape according to the present embodiment and may be configured following various conventional shapes. The first arm portion 2312 has a first grasping surface 2312a and a first outer surface 2312b.

The first grasping surface 2312a is an inner surface that contacts the tissue in the open-close direction B and faces the fixed arm 2002.

The first outer surface 2312b is a surface provided on the side opposite to the first grasping surface 2312a in the open-close direction B.

In the open-close direction B, the first arm portion 2312 is formed with a recess on the side of the first grasping surface 2312a and a rounded bulge on the side of the first outer surface 2312b. Therefore, when the tissue is grasped by the first movable arm 2031 and the fixed arm 2002, the tissue is accommodated in the recess portion included in the first movable arm 2031.

As shown in FIG. 55, FIG. 57 and FIG. 59, the second movable arm 2032 is provided so as to be openable and closable toward the lower end side B2 in the open-close direction B relative to the distal-end side A1 of the fixed arm 2002. Specifically, the second movable arm 2032 is provided to be openable and closable to the side opposite to the first movable arm 2031 relative to the fixed arm 2002 by means of a second rotation pin 2221 provided in the second through hole 2323. The second movable arm 2032 has a second slide slot 2320, a second engagement portion 2321, a second through hole 2323 and a second arm portion 2322.

The second slide slot 2320 is provided on the proximal-end side A2 of the second movable arm 2032, as shown in FIG. 59. The second slide slot 2320 engages with the second slide pin 2521, which will be described later.

The second engagement portion 2321 is an elastic member provided on the proximal-end side A2 of the second movable arm 2032 and having elasticity in the open-close direction B. The second engagement portion 2321 is, for example, a leaf spring. The second engagement portion 2321 is accommodated inside the clip holder 2004 when the second movable arm 2032 is closed relative to the fixed arm 2002. Specifically, as shown in FIG. 57, when the second movable arm 2032 is opened relative to the fixed arm 2002, the second engagement portion 2321 is positioned outside the clip holder 2004, which will be described later. On the other hand, as shown in FIG. 55, the second engagement portion 2321 is accommodated inside the clip holder 2004 when the second movable arm 2032 is closed relative to the fixed arm 2002. In the state in which the second movable arm 2032 is closed relative to the fixed arm 2002, the length L2 of the second engagement portion 2321 in the open-close direction B is substantially equal to or substantially larger than the inner diameter of the clip holder 2004.

In the present embodiment, when the second movable arm 2032 transitions from the closed state to the open state relative to the fixed arm 2002 in the open-close direction B, the second engagement portion 2321 rotates together with the second movable arm 2032, and the second engagement portion 2321 enters the inside of the clip holder 2004 from the most proximal end of the second engagement portion 2321. Each portion of the second engagement portion 2321 that contacts the clip holder 2004 may be formed in the rounded shape or processed such as the chamfering so as not to damage the inner circumferential surface of the clip holder 2004 in the process of the second engagement portion 2321 entering the inside of the clip holder 2004.

The second through hole 2323 is a hole penetrating through the second movable arm 2032 in the thickness direction C. The second through hole 2323 is arranged on the right side C2 of the through hole 2021 provided in the fixed arm 2002 in the thickness direction C and engages with the second rotation pin 2221. The second rotation pin 2221 connects the second through hole 2323 and the through hole 2022. This configuration allows the second movable arm 2032 to be rotatable about the second through hole 2323 as a center relative to the fixed arm 2002.

The second arm portion 2322 is formed by slightly bending a plate-shaped member of the resin or metal in a substantial cup shape. Here, the plate thickness direction of the first arm portion 2312 is substantially the same with the open-close direction B. By rotating the second arm portion 2322 following the open-close direction B relative to the fixed arm 2002, the distal-end portion of the second arm portion 2322 approaches the distal-end portion 2002a of the fixed arm 2002 so as to clamp the living tissue. Similar to the first arm portion 2312, in the second arm portion 2322, for example, the distal-end thereof may be formed into the claw shape in order to definitely clamp the living tissue. However, the second arm portion 2322 is not limited to the shape according to the present embodiment and may be formed following the various conventional structure. The second arm portion 2322 has a second grasping surface 2322a and a second outer surface 2322b.

The second grasping surface 2322a is an inner surface that contacts the tissue in the open-close direction B and faces the fixed arm 2002.

The second outer surface 2322b is a surface provided on the side opposite to the second grasping surface 2322a in the open-close direction B.

As shown in FIG. 59, in the open-close direction B, the second arm portion 2322 is formed with a recess on the side of the second grasping surface 2322a and a rounded bulge on the side of the second outer surface 2322b. Therefore, when the tissue is grasped by the second movable arm 2032 and the fixed arm 2002, the tissue is accommodated in the recess portion of the second movable arm 2032.

[Clip Holder 2004]

The clip holder 2004 is a pipe formed in a cylindrical shape having a longitudinal axis, as shown in FIG. 55. In the present embodiment, the clip holder 2004 is arranged along the longitudinal direction A. The clip holder 2004 is configured such that at least the proximal-end portions of the movable arm 2003 and the fixed arm 2002 in the closed state can enter therein. Also, the clip holder 2004 rotates together with the first movable arm 2031 and the second movable arm 2032 when the clip device 2100 is rotated in the circumferential direction.

The clip holder 2004 has groove portions 2041. The groove portions 2041 are formed on the distal-end side A1 of the clip holder 2004 and on the upper side B1 and the lower side B2 in the open-close direction B. The groove portions 2041 are, for example, slits formed from the distal end toward the proximal-end side A2, and have dimensions suitable for the first engagement portion 2311 of the first movable arm 2031 and the second engagement portion 2321 of the second movable arm 2032 to enter inside of the clip holder 2004.

The clip holder 2004 may include an engaging hole (not shown) formed at the base end A2 and with which the pair of tails 2024 of the fixed arm 2002 can be engaged, for example. Accordingly, the fixed arm 2002 is thereby attached to the clip holder 2004. The fixed arm 2002 and the clip holder 2004 may be integrally molded.

The clip holder 2004 has an inner diameter equal to or slightly shorter than the length L1 of the first engagement portion 2311 and the length L2 of the second engagement portion 2321. The clip holder 2004 can accommodate the first engagement portion 2311 and the second engagement portion 2321 inside therein. When the first movable arm 2031 rotates toward the lower side B2 in the open-close direction B, the first engagement portion 2311 enters the inside of the clip holder 2004 through the groove portion 2041. Also, when the second movable arm 2032 rotates toward the upper side B1 in the open-close direction B, the second engagement portion 2321 enters the inside of the clip holder 2004 from the groove portion 2041. The first movable arm 2031 can be opened again relative to the fixed arm 2002 until the first engagement portion 2311 is engaged to and locked by the clip holder 2004. Also, the second movable arm 2032 can be opened again relative to the fixed arm 2002 until the second engagement portion 2321 is engaged to and locked by the clip holder 2004.

When the first engagement portion 2311 is further pulled toward the proximal-end side A2 in the state in which the first engagement portion 2311 is accommodated inside the clip holder 2004, the first engagement portion 2311 abuts on the inner circumferential surface of the clip holder 2004 to be elastically deformed so as to be engaged with and locked inside the clip holder 2004. Also, when the second engagement portion 2321 is further pulled toward the proximal-end side A2 in the state in which the second engagement portion 2321 is accommodated inside the clip holder 2004, the second engagement portion 2321 abuts on the inner circumferential surface of the clip holder 2004 to be elastically deformed so as to be engaged with and locked inside the clip holder 2004. Accordingly, the closed state of the first movable arm 2031 and the second movable arm 2032 relative to the fixed arm 2002 is maintained. It is noted that the clip holder 2004 can at first lock either one of the first engagement portion 2311 and the second engagement portion 2321.

[Applicator 2200]

The applicator 2200 is a portion of the clip device 2100 that is not indwelled in the luminal cavity except for the treatment portion 2001. The applicator 2200 includes a traction member (connector) 2005, an operation wire 2006, a sheath 2007, and an operation portion 2008, as shown in FIG. 54 and FIG. 61.

[Traction Member 2005]

FIG. 61 is a view showing the traction member 2005 of the applicator 2200 of the clip device 2100.

As shown in FIG. 61, the traction member 2005 includes a first traction member 2051 and a second traction member 2052. Since the first traction member 2051 and the second traction member 2052 have substantially the same configuration, the figure of the second traction member 2052 is omitted.

The first traction member 2051 is arranged on the left side C1 relative to the connection portion 2020B of the fixed arm 2002. The first traction member 2051 connects the distal-end portion 2051a to the proximal-end side A2 of the first movable arm 2031. Also, the proximal-end side A2 of the first traction member 2051 is connected to the distal-end portion of the first operation wire 2061. The first traction member 2051 includes a first slide pin hole 2510 and a first slide pin 2511 at the distal-end portion thereof.

The first slide pin hole 2510 is a hole provided in the distal-end portion 2051a of the first traction member 2051. The first slide pin 2511 can be engaged with the first slide pin hole 2510. The first slide pin hole 2510 has a notch portion 2512 on the distal-end side A1.

The first slide pin 2511 connects the first slide pin hole 2510, the first slide slot 2310 of the first movable arm 2031 and the engagement groove 2023. The first slide pin 2511 can advance and retract along the first slide slot 2310 and the engagement groove 2023 by sliding the first slider 2812 of the operation portion 2008 along the longitudinal direction A. When the first slide pin 2511 advances along the first slide slot 2310 and the engagement groove 2023 toward the distal-end side A1, the first movable arm 2031 rotates around the first rotation pin 2211 as the center to open in the open-close direction B to enter the open state relative to the fixed arm 2002. When the first slide pin 2511 retracts along the first slide slot 2310 and the engagement groove 2023 toward the proximal-end side A2, the first movable arm 2031 rotates around the first rotation pin 2211 as the center to close in the open-close direction B to enter the closed state relative to the fixed arm 2002. Accordingly, the first movable arm 2031 is able to open and close relative to the fixed arm 2002 in the open-close direction B. Here, the state in which the first movable arm 2031 is closed relative to the fixed arm 2002 includes the state in which a distance between the distal end of the first movable arm 2031 and the distal end of the fixed arm 2002 is substantially zero. In this state, the first movable arm 2031 and the fixed arm 2002 can clamp the living tissues as the treatment target between the first movable arm 2031 and the fixed arm 2002.

The second traction member 2052 is arranged on the right side C2 relative to the connection portion 2020B of the fixed arm 2002. The second traction member 2052 connects the distal-end portion 2052a to the proximal-end side A2 of the second movable arm 2032. Also, the proximal-end side A2 of the second traction member 2052 is connected to the distal-end portion of the second operation wire 2062. The second traction member 2052 has a second slide pin hole 2520 and a second slide pin 2521 in the distal-end portion 2052a.

The second slide pin hole 2520 is provided in the distal-end portion 2052a of the second traction member 2052 and is a hole with which the second slide pin 2521 can be engaged. The second slide pin hole 2520 has a notch portion 2522 on the distal-end side A1.

The second slide pin 2521 connects the second slide pin hole 2520, the second slide slot 2320 of the second movable arm 2032 and the engagement groove 2023. The second slide pin 2521 can advance and retract along the second slide slot 2320 and the engagement groove 2023 by sliding the second slider 2822 of the operation portion 2008 along the longitudinal direction A. When the second slide pin 2521 advances along the second slide slot 2320 and the engagement groove 2023 toward the distal-end side A1, the second movable arm 2032 rotates around the second rotation pin 2221 as the center to open in the open-close direction B to enter the open state relative to the fixed arm 2002. When the second slide pin 2521 retracts along the second slide slot 2320 and the engagement groove 2023 toward the proximal-end side A2, the second movable arm 2032 rotates around the second rotation pin 2221 as the center to close in the open-close direction B to enter the closed state relative to the fixed arm 2002. Accordingly, the second movable arm 2032 is able to open and close relative to the fixed arm 2002 in the open-close direction B. Here, the state in which the second movable arm 2032 is closed relative to the fixed arm 2002 includes the state in which a distance between the distal end of the second movable arm 2032 and the distal end of the fixed arm 2002 is substantially zero. In this state, the distal end of the second movable arm 2032 and the distal end of the fixed arm 2002 can clamp the living tissues as the treatment target.

In the state in which the first movable arm 2031 is closed relative to the fixed arm 2002, and the first engagement portion 2311 is locked inside the clip holder 2004, the first slider 2812 of the operation portion 2008 is slid toward the proximal-end side A2. As a result, the notch portion 2512 is deformed or broken so as to be detached from the first slide pin 2511. The first traction member 2051 is separated from the connected fixed arm 2002 and the first movable arm 2031. Also, with regard to the second slide pin 2521, in the state in which the second movable arm 2032 is closed with the fixed arm 2002 and the second engagement portion 2321 is locked inside the clip holder 2004, the second slider 2822 of the operation portion 2008 is slid toward the proximal-end side A2. As a result, the notch portion 2522 is deformed or broken so as to be detached from the second slide pin 2521. The second traction member 2052 is separated from the connected fixed arm 2002 and the second movable arm 2032. When the first traction member 2051 and the second traction member 2052 are separated from the fixed arm 2002, the first movable arm 2031 and the second movable arm 2032, it is possible for the clip device 2100 to indwell the treatment portion 2001 including the fixed arm 2002, the movable arm 2003, and the clip holder 2004 in the luminal cavity in the state of grasping the tissues.

[Operation Wire 2006]

As shown in FIG. 61, the operation wire 2006 has a first operation wire 2061 and a second operation wire 2062. Since the first operation wire 2061 and the second operation wire 2062 have substantially the same configuration, the figure of the second operation wire 2062 is omitted.

The first operation wire 2061 connects the distal-end portion to the proximal-end portion of the first traction member 2051. The proximal-end portion of the first operation wire 2061 is fixed to the first slider 2812 of the operation portion 2008. The first operation wire 2061 is inserted through the sheath 2007 so as to be advanceable and retractable therein. The first operation wire 2061 may be formed of, for example, a metal single wire or twisted wire. Also, the outer circumferential surface of the first operation wire 2061 may be covered with a non-conductive member or the like. The first operation wire 2061 is fixed to the first traction member 2051 by various known methods such as adhesion, welding and the like. The first operation wire 2061 can advance or retract the first traction member 2051 by sliding the first slider 2812 of the operation portion 2008 attached to the proximal-end portion.

With regard to the second operation wire 2062, the distal-end portion thereof is connected to the proximal-end portion of the second traction member 2052. The proximal-end portion of the second operation wire 2062 is fixed to the second slider 2822 of the operation portion 2008. The second operation wire 2062 is inserted through the sheath 2007 so as to be advanceable and retractable therein. The second operation wire 2062 may be formed of, for example, a metal single wire or twisted wire. Further, the outer circumferential surface of the second operation wire 2062 may be covered with a non-conductive member or the like. The second operation wire 2062 is fixed to the second traction member 2052 by various known methods, such as adhesion, welding and the like. The second operation wire 2062 can advance or retract the second traction member 2052 by sliding the second slider 2822 of the operation portion 2008 attached to the proximal-end portion.

[Sheath 2007]

For example, as shown in FIG. 54, the sheath 2007 is configured to extend along the longitudinal direction A and is an elongated member that can be inserted into the luminal cavity. The sheath 2007 is made of an insulating material such as a fluororesin including PTFE (polytetrafluoroethylene) or a resin material such as HDPE (high density polyethylene). The sheath 2007 has the flexibility and can easily change the shape following the curved shape of the luminal tissue or the like inside the luminal cavity so as to be inserted into and removed from the channel (not shown) of the clip device 2100. A proximal-end portion 2007b of the sheath 2007 is connected to the operation portion 2008, and a distal-end portion 7a is connected to the proximal-end portion of the clip holder 2004. Also, the first operation wire 2061 and the second operation wire 2062 are inserted through the sheath 2007.

[Operation Portion (Handle) 8]

The operation portion 2008 includes a distal-end portion 2080a, a first operation portion 2081, and a second operation portion 2082, and extends in the longitudinal direction A, as shown in FIG. 54. The distal-end portion 2080a is connected to the proximal-end portion 2007b of the sheath 2007, as shown in FIG. 54. In the present embodiment, the directions in which the first operation portion 2081 and the second operation portion 2082, which are connected from the distal-end portion 2080a to the distal-end portion 2080a of the operation portion 2008, branch off from each other substantially coincide with the open-close direction B. The first operation portion 2081 and the second operation portion 2082 extend toward the upper side B1 and the lower side B2 in the up-down direction B from the distal-end portion 2080a toward the proximal-end side A2.

The first operation portion 2081 has a first operation portion main body 2811, a first slider 2812, and a finger hook portion 2813.

The first operation portion main body 2811 operates the first traction member 2051 and the first movable arm 2031 via the first operation wire 2061. The first operation portion main body 2811 of the first operation portion 2081 is formed in a substantially round rod shape extending in the longitudinal direction A.

The first slider 2812 is provided to slide in the longitudinal direction A to be advanceable and retractable in the first operation portion main body 2811. The proximal-end of the first operation wire 2061 is fixed to the first slider 2812. When the first slider 2812 is advanced and retracted along the first operation portion main body 2811 in the longitudinal direction A, the first operation wire 2061 and the first traction member 2051 fixed to the distal-end of the first operation wire 2061 are moved to advance and retract along the longitudinal direction A. Furthermore, when the first traction member 2051 advances and retracts along the longitudinal direction A, the first slide pin 2511 of the first traction member 2051 advances and retracts along the first slide slot 2310. Then, the first movable arm 2031 opens in the open-close direction B with the first rotation pin 2211 as the center. With this configuration, when the first slider advances and retracts along the first operation portion main body 2811 in the longitudinal direction A, it is possible to drive the first movable arm 2031 to perform the open-close operation in the open-close direction B.

The finger hook portion 2813 is a substantially ring-shaped finger hooking portion formed on the proximal-end side A2 of the first operation portion main body 2811.

The second operation portion 2082 has a second operation portion main body 2821, a second slider 2822, and a finger hook portion 2823.

The second operation portion main body 2821 operates the second traction member 2052 and the second movable arm 2032 via the second operation wire 2062. The second operation portion main body 2821 of the second operation portion 2082 is formed in a rod shape extending in the longitudinal direction A.

The second slider 2822 is provided to slide in the longitudinal direction A to be advanceable and retractable in the second operation portion main body 2821. A proximal-end of the second operation wire 2062 is fixed to the second slider 2822. The second slider 2822 is provided to be inserted through the second operation portion main body 2821. When the second slider 2822 advances and retracts along the second operation portion main body 2821 in the longitudinal direction A, the second operation wire 2062 and the second traction member 2052 fixed to the distal-end portion of the second operation wire 2062 are moved to advance and retract along the longitudinal direction A. Furthermore, when the second traction member 2052 advances and retracts along the longitudinal direction A, the second slide pin 2521 provided in the second traction member 2052 advances and retracts along the second slide slot 2320. Then, the second movable arm 2032 opens in the open-close direction B around the second rotation pin 2221 as the center. With this configuration, when the second slider 2822 advances and retracts along the second operation portion main body 2821 in the longitudinal direction A, it is possible to drive the second movable arm 2032 to perform the open-close operation in the open-close direction B.

The finger hook portion 2823 is a substantially ring-shaped finger hooking portion formed on the proximal-end side A2 of the second operation portion main body 2821.

[Operations and Effect of Clip Device 2100]

Next, operations and effect of the clip device 2100 will be described with reference from FIG. 62 to FIG. 65. In the present embodiment, as an example of how to use the clip device 2100, a procedure for ligating a wound in body tissue will be described.

FIG. 62 is a view schematically showing a state in which the first movable arm 2031 of the treatment portion 2001 of the clip device 2100 is opened and the treatment portion 2001 is moved to approach the tissue to be grasped. FIG. 63 is a schematic view showing the state of closing the first movable arm 2031 of the treatment portion 2001 of the clip device 2100 to grasp the tissue. FIG. 64 is a schematic view showing the state of opening the second movable arm 2032 and moving the treatment portion 2001 to approach the tissue to be grasped while the first movable arm 2031 of the treatment portion 2001 of the clip device 2100 is grasping the tissue. FIG. 65 is a schematic view showing a state of indwelling the treatment portion 2001 from the clip device 2100 in the state in which the second movable arm 2032 of the treatment portion 2001 of the clip device 2100 is closed and the treatment portion 2001 is grasping the tissue.

[Preparation]

As a preparation operation, a surgeon (not shown) identifies a wound in body tissue by a known method. Specifically, the surgeon inserts an insertion portion of an endoscope (not shown) into a digestive tract such as the esophagus, stomach, duodenum, or large intestine through a Natural orifice of a luminal cavity (for example, the mouth of a patient), and observes an image obtained by an imaging unit of the endoscope to specify a defect T of the tissue D inside the luminal cavity as the treatment target.

(Insertion Step)

The surgeon inserts the clip device 2100 into the channel of the endoscope, and protrudes the clip device 2100 from the distal-end opening of the channel of the endoscope. The surgeon moves the treatment portion 2001 provided on the distal-end side A1 of the clip device 2100 to the vicinity of the defect T.

(Arrangement Step)

As shown in FIG. 62, the surgeon opens and closes the first movable arm 2031 near the first portion Ta of the defect T as the treatment target. More specifically, when the surgeon slides the first slider 2812 in the longitudinal direction A toward the distal-end side A1, the first traction member 2051 moves toward the distal-end side A1. When the first slide pin 2511 connected to the first traction member 2051 advances, the first movable arm 2031 rotates about the first rotation pin 2211 as the center of rotation. The first movable arm 2031 rotates toward the upper side B1 in the open-close direction B such that the first arm portion 2312 on the distal-end side A1 is separated from the fixed arm 2002. As a result, the first movable arm 2031 enters the open state relative to the fixed arm 2002, and it is possible to grasp the first portion Ta of the defect T as the treatment target. In this state, the surgeon moves the first movable arm 2031 in the open state and the fixed arm 2002 toward the first portion Ta of the defect T that is intended to be grasped, and locate the first portion Ta between the first movable arm 2031 and the fixed arm 2002.

(Grasping Step)

In FIG. 63, when the surgeon can confirm that the first portion Ta of the defect T is positioned between the first movable arm 2031 and the fixed arm 2002, the surgeon pulls the first slider 2812 of the first operation portion 2081 so as to move the first traction member 2051 toward the proximal-end side A2. Therefore, when the first slide pin 2511 connected to the first traction member 2051 retracts, the first arm portion 2312 of the first movable arm 2031 rotates toward the lower side B2 in the open-close direction B toward the fixed arm 2002. As a result, the first movable arm 2031 enters the closed state relative to the fixed arm 2002 and grasps the first portion Ta of the defect T as the treatment target. At this time, the first portion Ta of the defect T is clamped by the first movable arm 2031 and the fixed arm 2002, and the first portion Ta enters to be near the connection portion of the rod central portion 2002d and the rod proximal-end portion 2002e of the fixed arm 2002.

During the process when the surgeon pulls the first slider 2812 toward the proximal-end side A2, the first engagement portion 2311 formed on the proximal-end side A2 of the first movable arm 2031 also rotates about the first rotation pin 2211 in the open-close direction B. As a result, the first engagement portion 2311 enters the groove portion 2041 formed in the clip holder 2004 and is accommodated inside the clip holder 2004. Accordingly, the first portion Ta of the defect T is grasped by the first movable arm 2031 and the fixed arm 2002. In this state, the state in which the first slider 2812 is pulled toward the proximal-end side A2 is maintained by the surgeon, and the state in which the first portion Ta of the defect T is grasped by the first movable arm 2031 and the fixed arm 2002 is maintained. However, it is possible for the surgeon to operate the operation portion 2008 again so as to rotate the first movable arm 2031 to transition the first movable arm 2031 to the open state relative to the fixed arm 2002 such that it is possible to re-grasp the first portion Ta of the defect T.

(Traction Step)

In FIG. 64, the surgeon maintains the state of grasping the first portion Ta of the defect T by the first movable arm 2031 and the fixed arm 2002 and moves the whole treatment portion 2001 to the vicinity of the second portion Tb of the defect T as the ligation target with the first portion Ta of the defect T. During this process, the surgeon maintains the closed state of the first movable arm 2031 and the fixed arm 2002.

(Arrangement Step)

When the surgeon confirms that the treatment portion 2001 reaches the vicinity of the second portion Tb of the defect T, the surgeon opens and closes the second movable arm 2032 near the second portion Tb of the defect T as the treatment target. More specifically, when the surgeon slides the second slider 2822 toward the distal-end side A1, the second traction member 2052 moves to the distal-end side A1. When the second slide pin 2521 connected to the second traction member 2052 advances, the second movable arm 2032 rotates about the second rotation pin 2221 as the center of rotation. The second movable arm 2032 rotates toward the lower side B2 in the open-close direction B such that the second arm portion 2322 on the distal-end side A1 is separated from the fixed arm 2002. As a result, the second movable arm 2032 is in the open state relative to the fixed arm 2002, and it is possible to grasp the second portion Tb of the defect T as the treatment target.

(Arm Deformation Step)

In FIG. 64, the surgeon slightly inclines the distal-end side A1 of the clip 2001 toward the upper side B1 in the open-close direction B so as to position the second portion Tb of the defect T that is intended to be grasped between the second movable arm 2032 and the fixed arm 2002 in the open state. Therefore, the second movable arm 2032 is arranged on the lower side B2 of the second portion Tb of the defect T. At this time, the rod distal-end portion 2002c of the fixed arm 2002 is rotated toward the upper side B1 together with the inclination of the clip 2001 such that the portion near the root of the first portion Ta of the defect T is pressed toward the upper side B1. The first portion Ta of the defect T applies a load relative to the fixed arm 2002 toward the lower side B2 so as to return to the original position. However, the rod central portion 2002d of the rod-shaped portion 2002b of the fixed arm 2002 is flexibly deformable. It is possible to release the load that is applied toward the lower side B2 by the first portion Ta of the defect T by making the rod central portion 2002d of the rod-shaped portion 2002b to be deformed.

(Grasping Step)

As shown in FIG. 65, when the surgeon can confirm that the second portion Tb of the defect T is positioned between the second movable arm 2032 and the fixed arm 2002, the surgeon pulls the second slider 2822 of the second operation portion 2082 to move the second traction member 2052 to the proximal-end side A2. Therefore, when the second slide pin 2521 connected to the second traction member 2052 retracts, the second arm portion 2322 of the second movable arm 2032 rotates toward the upper side B1 in the open-close direction B toward the fixed arm 2002. As a result, the second movable arm 2032 enters the closed state relative to the fixed arm 2002 so as to grasp the second portion Tb of the defect T as the treatment target. At this time, the second portion Tb of the defect T is clamped by the second movable arm 2032 and the fixed arm 2002 and enters the vicinity of the connection portion of the rod central portion 2002d and the rod proximal-end portion 2002e of the rod-shaped portion 2002b of the fixed arm 2002. The first portion Ta and the second portion Tb of the defect T is pressed toward the upper side B1 or the lower side B2 by the grasping force. However, the rod central portion 2002d of the rod-shaped portion 2002b of the fixed arm 2002 is flexibly deformable such that the force in the open-close direction B is adjustable. Accordingly, it is possible for the surgeon to disperse the force applied to the tissue D to maintain the grasping force without adjusting the grasping force relative to the first portion Ta and the second portion Tb of the defect T by pulling the first slider 2812 and the second slider 2822.

In the process in which the surgeon pulls the second slider 2822 toward the proximal-end side A2, the second engagement portion 2321 formed on the proximal-end side A2 of the second movable arm 2032 also rotates about the second rotation pin 2221 as the center in the open-close direction B. As a result, the second engagement portion 2321 enters the groove portion 2041 formed in the clip holder 2004 and is accommodated inside the clip holder 2004. Accordingly, the second portion Tb of the defect T is grasped by the second movable arm 2032 and the fixed arm 2002. In this state, the state in which the second slider 2822 is pulled toward the proximal-end side A2 is maintained by the surgeon, and the state in which the second portion Tb of the defect T is grasped by the second movable arm 2032 and the fixed arm 2002 is maintained. However, it is possible for the surgeon to operate the operation portion 2008 again so as to rotate the second movable arm 2032 to transition the second movable arm 2032 to the open state relative to the fixed arm 2002 such that it is possible to re-grasp the second portion Tb of the defect T.

Thereafter, when the first slider 2812 of the operation portion 2008 is further retracted toward the proximal-end side A2 in the longitudinal direction A, the clip holder 2004 makes the first engagement portion 2311 of the first movable arm 2031 to be engaged with the inside of the clip holder 2004 so as to lock the first movable arm 2031 to not to open. Also, when the second slider 2822 of the operation portion 2008 is further retracted toward the proximal-end side A2 in the longitudinal direction A, the clip holder 2004 makes the second engagement portion 2321 of the second movable arm 2032 to be engaged with the inside of the clip holder 2004 so as to lock the second movable arm 2032 to not to open.

(Indwelling Step)

By the above-described treatment, the first portion Ta and the second portion Tb of the defect T as the treatment targets are grasped by the treatment portion 2001, as shown in FIG. 65. In this state, the surgeon further pulls the first slider 2812 of the first operation portion 2081 and the second slider 2822 of the second operation portion 2082 toward the proximal-end side A2 to move the first traction member 2051 and the second traction member 20051 to the proximal-end side A2.

In the present embodiment, the first traction member 2051 and the second traction member 2052 are detachably attached to the first slide pin 2511 and the second slide pin 2521, respectively. For example, by the surgeon pulling the first traction member 2051 toward the proximal-end side A2, the notch portion 2512 of the first traction member 2051 is deformed or broken, and the first slide pin 2511 comes out of the first slide pin hole 2510 so as to release the engagement. Also, by pulling the second traction member 2052 toward the proximal-end side A2, the notch portion 2522 of the second traction member 2052 is deformed or broken, and the second slide pin 2521 comes out of the second slide pin hole 2520 and so as to release the engagement. It is noted that that the specific configuration of the engagement between the first traction member 2051 and the first slide pin 2511, and the engagement between the second traction member 2052 and the second slide pin 2521 are not limited to the present embodiment.

When the amount of the force that the surgeon moves the first traction member 2051 and the second traction member 2052 toward the proximal-end side A2 exceeds a predetermined value, as described above, the engagement between the first traction member 2051 and the first slide pin 2511 and the engagement between the second traction member 2052 and the second slide pin 2521 are released. Accordingly, the treatment portion 2001 of the clip device 2100 is indwelled inside the luminal cavity in the state in which the first movable arm 2031 and the fixed arm 2002 grasp the first portion Ta of the defect T and the second movable arm 2032 and the fixed arm 2002 grasp the second portion Tb of the defect T.

The surgeon then operates the operation portion 2008 of the clip device 2100 to remove the sheath 2007 to the outside of the patient's body to complete the treatment for the treatment target.

In the present embodiment, with the above-described configuration, it is possible for the treatment portion 2001 of the clip device 2100 to close the defect T of the tissue D as the treatment target.

Also, in the present embodiment, the rod central portion 2002d of the rod-shaped portion 2002b of the fixed arm 2002 is flexibly deformable such that it is possible to decrease the load applied to the fixed arm 2002 and the movable arm 2003. Accordingly, it is possible for the treatment portion 2001 to grasp the tissue without damaging or tearing the tissue without strongly grasping the tissue by the fixed arm 2002 and the movable arm 2003.

Also, in the present embodiment, the bending rod central portion 2002d has the elasticity in a degree to firmly grasp the tissue without damaging or tearing the tissue due to the force that repels in the direction opposite to the direction in which the load is applied. Accordingly, at the time of pulling the tissue toward the hand side, it is possible to suitably make the rod central portion 2002d to be deformed so as to grasp the tissue and prevent the tissue from slipping off.

Also, in the present embodiment, for example, when the surgeon inclines the clip 2001 as described above, the first portion Ta of the defect T that is pressed toward the upper side B1 applies the load relative to the fixed arm 2002 toward the lower side so as to return to the original position. At this time, the rod central portion 2002d of the rod-shaped portion 2002b is flexibly deformable such that it is possible for the fixed arm 2002 to release the load to the lower side B1 by the first portion Ta of the defect T by flexibly deforming the rod central portion 2002d of the rod-shaped portion 2002b. Accordingly, it is possible for the surgeon to perform the treatment relative to the defect IT without slightly adjusting the grasping force of the clip 2001 of the clip device 2100 during the surgery.

Also, the arm deformation step according to the present embodiment may be applied in the grasping step. For example, the defect T of the tissue D that is grasped by the first movable arm 2031 or the second movable arm 2032 and the fixed arm 2002 applies the load relative to the clip 2001 so as to return to the original shape. However, the rod central portion 2002d of the fixed arm 2002 is flexibly deformable such that it is possible for the fixed arm 2002 to release the load applied to the clip 2001 by flexibly deforming the rod central portion 2002d of the fixed arm 2002. Accordingly, it is possible to suitably grasp the tissue without damaging or tearing the tissue.

As described above, the sixth embodiment of the present disclosure has been described in detail with reference to the drawings; however, the specific configuration is not limited to the present embodiment, and design changes and the like are included within the scope of the present disclosure. Also, the configurational elements shown in the above-described embodiment and each embodiment shown below can be combined as appropriate.

Seventh Embodiment

Next, a seventh embodiment of the present disclosure will be described with reference to FIG. 66 to FIG. 70. In the following description, the same reference signs are given to the same configurations as those already described, and redundant descriptions will be omitted. Each of the following embodiments differs from the sixth embodiment in the fixed arm and the movable arm. Therefore, in the following description, the differences from the sixth embodiment will be mainly described. FIG. 66 is a view showing a state in which a treatment portion (clip) 2001A of a clip device 2100A according to the seventh embodiment of the present disclosure is closed. FIG. 67 is a schematic view showing a state of opening a first movable arm 2031A of the treatment portion 2001A of the clip device 2100A to make the treatment portion 2001A to approach the tissue to be grasped. FIG. 68 is a schematic view showing a state of closing the first movable arm 2031A of the treatment portion 2001A of the clip device 2100A and grasping the tissue. FIG. 69 is a schematic view showing a state of opening the second movable arm 2032A and making the treatment portion 2001A to approach the tissue to be grasped while the first movable arm 2031A of the treatment portion 2001A of the clip device 2100A is grasping the tissue. FIG. 70 is a schematic view showing a state of closing the second movable arm 2032A of the treatment portion 2001A of the clip device 2100A to indwell the treatment portion 2001A from the clip device 2100A in a state in which the treatment portion 2001A is grasping the tissue.

The clip device 2100A according to a seventh embodiment of the present disclosure includes the treatment portion (clip) 2001A and the applicator 2200. Here, the applicator 2200 is same with that according to the sixth embodiment such that the description and drawings are omitted.

As shown in FIG. 66, the treatment portion 2001A includes the fixed arm 2002A, the movable arm 2003A, and the clip holder 2004. The fixed arm 2002 and the clip holder 2004 are the same with that according to the sixth embodiment such that the description and drawings are omitted.

As shown in FIG. 66, the fixed arm 2002A includes a rod portion 2020A and a connection portion 2020B. Also, the rod portion 2020A includes the distal-end portion 2002a and a rod-shaped portion 2002Ab. The connection portion 2020B and the distal-end portion 2002a are the same with that according to the sixth embodiment and the description thereof is omitted.

As compared with the sixth embodiment, the rod-shaped portion 2002Ab has the same configuration with that of the rod-shaped portion 2002b except for that the rod distal-end portion 2002c, the rod central portion 2002d, and the rod proximal-end portion 2002e are not provided. The rod-shaped portion 2002Ab is integrally formed of using the metal material (second material) that is same with the rod distal-end portion 2002c and the rod proximal-end portion 2002e according to the sixth embodiment, for example.

As shown in FIG. 66, the movable arm 2003A includes a first movable arm 2031A that opens and closes in the upper side in the open-close direction B relative to the fixed arm 2002 and a second movable arm 2032A that opens and closes in the lower side in the open-close direction B relative to the fixed arm 2002. The first movable arm 2031A and the second movable arm 2032A are independently operable to open and close.

The first movable arm 2031A includes the first slide slot 2310, the first engagement portion 2311, the first through hole 2313, and a first arm portion 2312A. The first slide slot 2310, the first engagement portion 2311, and the first through hole 2313 are the same with that according to the sixth embodiment such that the description is omitted.

As shown in FIG. 66, the first arm portion 2312A is formed in a substantial cup shape by slightly bending a plate-shaped member formed of the resin or metal. Similar to the sixth embodiment, the plate width direction of the first arm portion 2312A is substantially coincided with the open-close direction B. The first arm portion 2312A is able to clamp the living tissue by rotating in the open-close direction B relative to the fixed arm 2002. The first arm portion 2312A includes a first arm distal-end portion 2031c, a first arm central portion 2031d, a first arm proximal-end portion 2031e, the first grasping surface 2312a, and the first outer surface 2312b. The first grasping surface 2312a and the first outer surface 2312b are the same with that according to the sixth embodiment such that the description is omitted.

As shown in FIG. 66, the first arm distal-end portion (second region) 2031c is a part of the first arm portion 2312A and is provided at the distal-end side A1 of the first arm portion 2312A. The first arm distal-end portion 2031c is formed by using the metal material (second material) having the elastic modulus higher than that of the first arm central portion 2031d. The metal material of the first arm distal-end portion 2031c can be suitably adopted as the metal material (second material) described in the sixth embodiment.

As shown in FIG. 66, the first arm central portion (first region) 2031d is a part of the first arm portion 2312A and is provided in the central portion of the first arm portion 2312A. The first arm central portion 2031d is provided at the proximal-end side A2 of the first arm distal-end portion 2031c. The first arm central portion 2031d has the elastic modulus lower than that of the first arm distal-end portion 2031c so as to be flexibly deformable. For example, the first arm central portion 2031d is bent toward the direction where the load is applied when the grasped tissue applies the load toe the movable arm 2003A. Thereafter, the bent first arm central portion 2031d may have the elasticity in the degree of firmly grasping the tissue without damaging or tearing the tissue due to the force that repels in the direction opposite to the direction in which the load is applied. The first arm central portion 2031d may be the leaf spring or the like. As described in the sixth embodiment, the first arm central portion 2031d may be suitably formed by adopting the metal material (first material) having the elasticity to be flexibly deformable.

As shown in FIG. 66, the first arm proximal-end portion (second region) 2031e is a part of the first arm portion 2312A and is provided at the proximal-end side A2 of the first arm portion 2312A. The first arm proximal-end portion 2031e is provided at the proximal-end side A2 of the first arm distal-end portion 2031c and the first arm central portion 2031d. The elastic modulus of the first arm proximal-end portion 2031e is substantially the same with that of the first arm distal-end portion 2031c and higher than that of the first arm central portion 2031d. The first arm proximal-end portion 2031e is suitably formed by using the same material (second material) with that of the first arm distal-end portion 2031c.

The proximal-end portion of the first arm distal-end portion 2031c on the proximal-end side A2 is connected and bonded with the distal-end portion of the first arm central portion 2031d on the distal-end side A1. The proximal-end portion of the first arm central portion 2031d on the proximal-end side A2 is connected and bonded with the distal-end portion of the first arm proximal-end portion 2031e on the distal-end side A1. In the present embodiment, the first arm portion 2312A is formed by integrating respective connection portions of the first arm distal-end portion 2031c, the first arm central portion 2031d, and the first arm proximal-end portion 2031e by the metal bonding. Also, the corresponding connection portions of the first arm distal-end portion 2031c, the first arm central portion 2031d, and the first arm proximal-end portion 2031e are stacked in the thickness direction C or the open-close direction R to be further firmly bonded with each other due to the metal bonding. Accordingly, the peeling rarely occurs in the connection portions. The sequence of stacking the connection portions is not particularly limited. Also, the end surfaces of the connection portions of the first arm distal-end portion 2031*c*, the first arm central portion 2031*d*, and the first arm proximal-end portion 2031*e* may be formed in an inclined surface shape. With this configuration, the stress acting on the connection portions is suitably dispersed so as to make the stress difficult to concentrate on a specific portion. Therefore, even if the first arm portion 2312A is formed by using different metal materials in the first arm distal-end portion 2031*c*, the first arm central portion 2031*d*, and the first arm proximal-end portion 2031*e*, it is possible for the surgeon to use the clip device 2100A without worrying about the peeling of the connection portion.

Here, the material of the first arm distal-end portion 2031*c*, the first arm central portion 2031*d*, and the first arm proximal-end portion 2031*e* is not particularly limited. The first arm distal-end portion 2031*c*, the first arm central portion 2031*d*, and the first arm proximal-end portion 2031*e* may be formed from the metal material respectively, or may be formed from the resin material or the like besides the metal. For example, the resin having high rigidity, the thermoplastic or serializable resin with suitable elasticity such as the resin materials include polyphthalamide (PPA), polyamide (PA), polyetheretherketone (PEEK), LCP (liquid crystalline polymer), acrylonitrile butadiene styrene (ABS), polyphenylene sulfide (PPS), and the like may be used. Also, the connection portions of the first arm distal-end portion 2031*c*, the first arm central portion 2031*d*, and the first arm proximal-end portion 2031*e* are not limited to the metal bonding. For example, in a case in which the connection portions of the first arm distal-end portion 2031*c*, the first arm central portion 2031*d*, and the first arm proximal-end portion 2031*e* are made of the same kind of material such as the metal, they may be integrally formed by welding of spotting, laser, resistance and the like, brazing, caulking, or the like. In a case in which the first arm distal-end portion 2031*c*, the first arm central portion 2031*d*, and the first arm proximal-end portion 2031*e* are made of different materials such as the metal, the resin and the like, they may be integrally formed by welding using heat, ultrasonic waves, laser, high frequency or the like, insert molding, or the like.

The second movable arm 2032A includes the second slide slot 2320, the second engagement portion 2321, the second through hole 2323, and a second arm portion 2322A. The second slide slot 2320, the second engagement portion 2321, and the second through hole 323 are the same with that according to the sixth embodiment such that the description thereof is omitted.

As shown in FIG. 66, the second arm portion 2322A is formed in a substantial cup shape by slightly bending a plate-shaped member formed of the resin or metal. Similar to the sixth embodiment, the plate width direction of the second arm portion 2322A is substantially coincided with the open-close direction B. The second arm portion 2322A is able to clamp the living tissue by rotating in the open-close direction B relative to the fixed arm 2002. The second arm portion 2322A includes a second arm distal-end portion 2032*c*, a second arm central portion 2032*d*, a second arm proximal-end portion 2032*e*, the second grasping surface 2322*a*, and the second outer surface 2322*b*. The second grasping surface 2322*a* and the second outer surface 2322*b* are the same with that according to the sixth embodiment such that the description is omitted.

As shown in FIG. 66, the second arm distal-end portion (second region) 2032*c* is a part of the second arm portion 2322A and is provided at the distal-end side A1 of the second arm portion 2322A. The second arm distal-end portion 2032*c* is formed by using the metal material (second material) having the high elastic modulus similar to the first arm distal-end portion 2031*c*.

As shown in FIG. 66, the second arm central portion (first region) 2032*d* is a part of the second arm portion 2322A and is provided at the proximal-end side A2 of the second arm distal-end portion 2032*c*. The second arm central portion 2032*d* has the elastic modulus lower than that of the second arm distal-end portion 2032*c* so as to be flexibly deformable. For example, the second arm central portion 2032*d* is bent toward the direction where the load is applied when the grasped tissue applies the load toe the movable arm 2003A. Thereafter, the bent second arm central portion 2032*d* may have the elasticity in the degree of firmly grasping the tissue without damaging or tearing the tissue due to the force that repels in the direction opposite to the direction in which the load is applied. The second arm central portion 2032*d* may be the leaf spring or the like. Similar to the first arm central portion 2031*d*, the second arm central portion 2032*d* may be suitably formed by adopting the metal material (first material) having the elasticity to be flexibly deformable.

As shown in FIG. 66, the second arm proximal-end portion (second region) 2032*e* is a part of the second arm portion 2322A and is provided at the proximal-end side A2 of the second arm distal-end portion 2032*c* and the second arm central portion 2032*d*. The elastic modulus of the second arm proximal-end portion 2032*e* is substantially the same with that of the second arm distal-end portion 2032*c*. The second arm proximal-end portion 2032*e* is suitably formed by using the same material (second material) with that of the second arm distal-end portion 2032*c*.

The proximal-end portion of the second arm distal-end portion 2032*c* on the proximal-end side A2 is connected and bonded with the distal-end portion of the second arm central portion 2032*d* on the distal-end side A1. The proximal-end portion of the second arm central portion 2032*d* on the proximal-end side A2 is connected and bonded with the distal-end portion of the second arm proximal-end portion 2032*e* on the distal-end side A1. In the present embodiment, the second arm portion 2322A is formed by integrating respective connection portions of the second arm distal-end portion 2032*c*, the second arm central portion 2032*d*, and the second arm proximal-end portion 2032*e* by the metal bonding. The connection portions and the material thereof included in the second arm portion 2322A is the same with the configuration of the above-described first arm portion 2312A such that the description is omitted.

(Operations and Effect of Clip Device 2100A)

In the present embodiment, the operations shown in FIG. 67 to FIG. 70 are the same with the operations of the clip device as described in FIG. 62 to FIG. 65 according to the sixth embodiment. Accordingly, the description of the operations is omitted, and the effect of the clip device 2100A according to the present embodiment will be described by using FIG. 67 to FIG. 70.

As shown in FIG. 67, similar to the sixth embodiment, the surgeon opens and closes the first movable arm 2031A that is close to the first portion Ta of the defect T as the treatment target and moves the first movable arm 2031A and the fixed arm 2002 toward the first portion Ta of the defect T. Thereafter, the surgeon positions the first portion Ta between the first movable arm 2031A and the fixed arm 2002A.

In FIG. 68, the surgeon pulls the first slider 2812 of the first operation portion 2081 to rotate the first movable arm 2031A toward the lower side B2 in the open-close direction B so as to grasp the first portion Ta of the defect T. At this time, for example, when the surgeon pulls the first slider 2812 too far, the first portion Ta is grasped too strongly by the first movable arm 2031A. The grasped first portion Ta applies the load to the first movable arm 2031A and the fixed arm 2002A to return to the original position. However, the first arm central portion 2031d of the first movable arm 2031A is flexibly deformable. Accordingly, it is possible for the first movable arm 2031A to release the load toward the upper side B1 that is applied by the first portion Ta of the defect T by making the first arm central portion 2031d to be bent and deformed toward the upper side B1.

In FIG. 69, the surgeon moves the entire treatment portion 2001A to the vicinity of the second portion Tb of the defect T while maintaining the state in which the first portion Ta of the defect T is grasped by the first movable arm 2031A and the fixed arm 2002A. At this time, the first portion Ta applies the load relative to the first movable arm 2031A and the fixed arm 2002A so as to return to the original position. However, the bent first arm central portion 2031d of the first movable arm 2031A has the elasticity in the degree of firmly grasping the tissue without damaging or tearing the tissue due to the force that repels in the direction opposite to the direction in which the load is applied. Accordingly, at the time of pulling the tissue to the hand side, the first arm central portion 2031d is suitably bent and deformed so as to grasp the tissue and prevent the tissue from slipping off. The surgeon opens and closes the second movable arm 2032A close to the second portion Tb of the defect T to move the second movable arm 2032A and the fixed arm 2002A in the open state toward the second portion Tb of the defect T. Thereafter, the surgeon positions the second portion Tb between the second movable arm 2032A and the fixed arm 2002A.

In FIG. 70, the surgeon pulls the second slider 2822 of the second operation portion 2082 to rotate the second movable arm 2032A toward the upper side B1 in the open-close direction B so as to grasp the second portion Tb of the defect T. At this time, for example, when the surgeon pulls the second slider 2822 too far, the second portion Tb is grasped too strongly by the second movable arm 2032A. The grasped second portion Tb applies the load to the second movable arm 2032A and the fixed arm 2002A to return to the original position. However, the second arm central portion 2032d of the second movable arm 2032A is flexibly deformable. Accordingly, it is possible for the second movable arm 2032A to release the load toward the lower side B2 that is applied by the second portion Tb of the defect T by making the second arm central portion 2032d to be bent and deformed toward the lower side B2.

In the present embodiment, similar to the above-described sixth embodiment, the first arm central portion 2031d of the first movable arm 2031A and the second arm central portion 2032d of the second movable arm 2032A are flexibly deformable such that it is possible to reduce the load applied to the first movable arm 2031A and the second movable arm 2032 due to the deformation at the time of grasping the defect T of the tissue. Accordingly, it is possible for the treatment portion 2001A to adjust the grasping force applied to the grasped tissue by the fixed arm 2002A and the movable arm 2003A so as to eliminate the possibility of damaging and tearing the tissue while preventing the tissue from slipping off.

As described above, the seventh embodiment of the present disclosure has been described in detail with reference to the drawings; however, the specific configuration is not limited to the present embodiment, and design changes and the like are included within the scope of the present disclosure. Also, the configurational elements shown in the above-described embodiment and modification example shown below can be combined as appropriate.

(Modification Example)

The clip device 2100 according to the above-described sixth embodiment includes the flexibly deformable rod central portion 2002d at the center of the rod-shaped portion 2002b of the fixed arm 2002; however, the present disclosure is not limited to the configuration. For example, as shown in FIG. 71, the rod distal-end portion (first region) 2Bc of the rod-shaped portion 2002b of the fixed arm 2002 may be flexibly deformable. In this case, the rod distal-end portion 2002Bc is suitably formed by using the metal material (first material) having the elasticity to be flexibly deformable. With this configuration, the clip 2001 includes the region being flexibly deformable at the distal-end side A1 of the fixed arm 2002. Accordingly, at the time of grasping the tissue, it is possible for the clip 2001 to firmly grasp the tissue since the proximal-end side A2 thereof is not flexibly deformed while reducing the load applied on the movable arm 2003 and the fixed arm 2002 from the tissue since the rod distal-end portion 2002Bc at the distal-end side A1 of the fixed arm 2002 is flexibly deformed. Also, as shown in FIG. 72, the rod proximal-end portion (first region) 2002Be of the rod-shaped portion 2002b of the fixed arm 2002 may be flexibly deformable. With this configuration, the clip 2001 includes the flexibly deformable region at the proximal-end side A2 of the fixed arm 2002. Accordingly, at the time of grasping the tissue, the rod proximal-end portion 2002Be at the proximal-end side A2 of the fixed arm 2002 is flexibly deformed such that the clip 2001 faces the proximal-end side A2 of the tissue and it is possible to reduce the risk of damaging the tissue even if the distal end of the tissue that is more fragile than the proximal end thereof abuts on the rod proximal-end portion 2002Be. Also, the clip device 2100A according to the above-described seventh embodiment includes the flexibly deformable first arm central portion 2031d at the center of the first arm portion 2312A and the flexibly deformable second arm central portion 2032d at the center of the second arm portion 2322A; however, the present disclosure is not limited to this configuration. Similar to the sixth embodiment, the first arm distal-end portion 2031c, the first arm proximal-end portion 2031e, the second arm distal-end portion 2032c, and the second arm proximal-end portion 2032e may be flexibly deformable.

Also, the first arm central portion (first region) 2031d of the first movable arm 2031A and the second arm central portion (first region) 2032d of the second movable arm 2032A may be formed as thin-wall portions, for example. As shown in FIG. 73, the first arm distal-end portion 2031Cc and the first arm proximal-end portion 2031Ce included in the first arm portion 2312C or the second arm distal-end portion 2032Cc and the second arm proximal-end portion 2032Ce included in the second arm portion 2322C are defined as the second region. As shown in FIG. 73, the second region has a second thickness in the open-close direction B as the plate thickness direction of the first arm portion 2312C and the second arm portion 2322C. Here, the first movable arm 2031C and the second movable arm 2032C have substantially the same configuration such that the figure of the second movable arm 2032C is omitted. The first arm central portion 2031Cd of the first movable arm 2031C and the second arm central portion 2032Cd of the second movable arm 2032C are defined as the first region. The first region is formed as a thin-wall portion having a thin thickness (first thickness) in the open-close direction B than the second thickness of the second region. Accordingly, for example, even if the entire first movable arm 2031C or the second movable arm 2032C are formed in the same material, only the first region is formed as the thin-wall portion such that it is easier for the first region to be flexibly deformed than the second region. Accordingly, the same effect as that according to the above-described embodiment can be achieved. Also, the entire first movable arm 2031C or the entire second movable arm 2032C can be formed of the same material so as to reduce the number of the members in the manufacturing of the clip device. Also, the first movable arm 2031C or the second movable arm 2032C does not have the connection portion such that it is possible for the user to use the clip device without worrying the peeling or the like occurred in the connection portion. Also, the above-described modification example is not limited to the movable arm. Similarly, the first region (for example, the rod central portion 2002d) included in the fixed arm 2002 according to the sixth embodiment may be formed as the thin thin-wall portion (first thickness) that is thinner than the second thickness of the second region (for example, the rod distal-end portion 2002c or the rod proximal-end portion 2002e). Even in this case, it is possible for the clip device to achieve the same effect as that according to the above-described embodiment.

Also, the first movable arm 2031A and the second movable arm 2032A according to the seventh embodiment may include the first region to be flexibly deformed and the second region not to be flexibly deformed by including a region being bent and a region not to be bent. As shown in FIG. 74, the first movable arm 2031D includes a first arm distal-end portion (second region) 2031Dc, a first arm central portion (first region) 2031Dd, and a first arm proximal-end portion (second region) 2031De in a first arm portion 2312D. The first arm distal-end portion 2031Dc and the first arm proximal-end portion 2031De include a bending portion (rigidity strengthen portion) 2031f that is formed by the first movable arm 2031D and the fixed arm 2002A by bending an end in the thickness direction C from the contact surface for contacting the tissue. Here, the contact surface according to the present embodiment is the above-described first grasping surface 2312a according to the sixth embodiment. A distal end of the bending portion 2031f protrudes toward the lower side B2 in the open-close direction B separating from the first grasping surface 2312a. Accordingly, the bending portion 31f strengthens the rigidity in the open-close direction B. On the other hand, the first arm central portion 2031Dd does not include the bending portion 2031f. For example, in the case in which the first movable arm 2031D is formed in the flexibly deformable material (first material), the first arm central portion 2031Dd is flexibly deformed. On the other hand, in the first arm distal-end portion 2031Dc and the first arm proximal-end portion 2031De, the flexible deformation is suppressed due to the bending portion 2031f. Accordingly, it is more difficult for the first arm distal-end portion 2031Dc and the first arm proximal-end portion 2031De to be flexibly deformed as compared with the first arm central portion 2031Dd. Accordingly, the clip device can achieve the same effect as that according to the above-described embodiment. Also, the above-described modification example may be applied to the second movable arm. Also, the contact surface is not limited to the first grasping surface 2312a. Also, the direction where the distal end of the bending portion faces it not particularly limited and may not be directed to the open-close direction. Also, the second region only has to be a configuration that is not flexibly deformed as compared with the first region due to including the bending portion (rigidity strengthen portion). Also, even in the sixth embodiment, the first region to be flexibly deformed and the second region not to be flexibly deformed by including the region being bent and the region not to be bent may be provided. For example, the second region (for example, the rod distal-end portion 2002c and the rod proximal-end portion 2002e) may include the bending portion (rigidity strengthen portion) formed by bending the end in the thickness direction C from the contact surface being contact with the tissue. In this case, the first region (for example, the rod central portion 2002d) may not include the bending portion (rigidity strengthen portion).

Also, the flexibly deformable first region according to the present disclosure may be included in all of the first movable arm, the second movable arm, and the fixed arm, or at least included in either of the configurations. Also, the first region may be the entire region of the movable arm or the fixed arm, or a part thereof as in the above-described embodiments.

In either of the above-described embodiments, according to the clip and the clip device according to the present disclosure, it is possible to prevent the tissue from slipping off from the arms and definitely grasping the tissue.

What is claimed is:

1. A clip operation method, comprising:
   retracting a first slider on a first handle to bring a first arm and a central arm closer, wherein the first slider is slidably attached to the first handle;
   attaching a stopper to the first handle distal to the first slider to fix a position of the first arm relative to the central arm;
   operating a second slider to open a second arm relative to the central arm while attaching the stopper to the first handle distal to the first slider, wherein the second slider is slidably attached to a second handle, and the first handle and the second handle are connected at a distal-end portion; and
   removing the stopper from the first handle.

2. The clip operation method according to claim 1, wherein the placing the stopper includes abutting the stopper to a distal-end side of the first slider to restrict the movement of the first slider distally.

3. The clip operation method according to claim 2, wherein the abutting the stopper includes moving the stopper toward the distal-end side of the first slider.

4. The clip operation method according to claim 1, further comprising:
   drawing a first portion of a tissue toward a second portion of the tissue while restricting a movement of the first slider; and
   sliding the second slider relative to the second handle after grasping the second portion of the tissue, the second slider configured to open and close the second arm.

5. The clip operation method according to claim 4, further comprising:
   after removing the stopper from the first handle:
   grasping a third portion of the tissue between the first arm and the central arm, the third portion of the tissue being different from the first portion of the tissue, and
   reattaching the stopper to the first handle and placing the stopper distal to the first slider to restrict a movement of the first slider.

6. The clip operation tissue according to claim 1, further comprising:
   restricting a movement of the first slider distally by attaching the stopper to the first handle and placing the stopper distal to the first slider, and
   allowing a movement of the first slider proximally.

7. The clip operation method according to claim 6, further comprising:

moving the first slider proximally while restricting a movement of the first arm relative to the central arm.

8. The clip operation method according to claim 6, further comprising:

moving the first slider proximally while restricting a movement of the first slider distally to release a connection between the first arm and an applicator including the first slider.

* * * * *